US008822665B2

(12) United States Patent
Prehaud et al.

(10) Patent No.: US 8,822,665 B2
(45) Date of Patent: Sep. 2, 2014

(54) NEURON GENERATION, REGENERATION AND PROTECTION

(75) Inventors: Christophe Prehaud, Guyancourt (FR); Monique Lafon, Paris (FR); Matthias Johannes Schnell, Harleysville, PA (US)

(73) Assignees: Institut Pasteur, Paris Cedex (FR); Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 13/263,050

(22) PCT Filed: Apr. 2, 2010

(86) PCT No.: PCT/IB2010/000967
§ 371 (c)(1),
(2), (4) Date: Dec. 21, 2011

(87) PCT Pub. No.: WO2010/116258
PCT Pub. Date: Oct. 14, 2010

(65) Prior Publication Data
US 2012/0100116 A1   Apr. 26, 2012

(30) Foreign Application Priority Data
Apr. 7, 2009   (EP) ..................................... 09290257

(51) Int. Cl.
*C12N 15/47* (2006.01)
*C07K 14/145* (2006.01)

(52) U.S. Cl.
USPC .................. 536/23.72; 435/69.1; 435/252.33; 435/320.1

(58) Field of Classification Search
None
See application file for complete search history.

(56) References Cited

U.S. PATENT DOCUMENTS

| 2004/0071675 A1 | 4/2004 | Mazarakis et al. |
| 2004/0076613 A1 | 4/2004 | Mazarakis et al. |
| 2008/0311147 A1 | 12/2008 | Schnell et al. |

FOREIGN PATENT DOCUMENTS

| EP | 0094887 A2 | 11/1983 |
| JP | 2004-517057 A | 6/2004 |
| JP | 2006-502240 A | 1/2006 |
| WO | 83/04052 A1 | 11/1983 |
| WO | 03/048198 | 6/2003 |
| WO | 2004/031390 | 4/2004 |
| WO | 2006/078272 | 7/2006 |
| WO | 2007/121895 | 11/2007 |
| WO | 2008138649 A2 | 11/2008 |

OTHER PUBLICATIONS

Prehaud et al. "Glycoprotein of Nonpathogenic Rabies Viruses is a Key Determinant of Human Cell Apoptosis", Journal of Virology, 2003; vol. 77, No. 19, pp. 10537-10547, XP-002532332.
Prehaud et al. "Rabies Virus Strain CVS Glycoprotein Gene, Complete CDS", Journal of Virol, 2003; vol. 77, No. 19, pp. 1-2, XP-002532334.
Klingen et al. "Double-Labeled Rabies Virus: Live Tracking of Enveloped Virus Transport", Journal of Virology, 2008; vol. 82, No. 1, pp. 237-245, XP-002532333.
Dietzschold et al. "New Approaches to the Development of Live Attenuated Rabies Vaccines", Hybridoma and Hybridomics, 2002; vol. 21. No. 2, pp. 129-134 XP-002323000.
Prehaud et al. "Antigenic Site II of the Rabies Virus Glycoprotein: Structure and Role in Viral Virulence", Journal of Virology, 1988; vol. 62. No. 1, pp. 1-7.
Prehaud et al. "Attenuation of Rabies Virulence: Takeover by the Cytoplasmic Domain of its Envelope Protein", Science Signaling, 2010; vol. 3. Issue 105, pp. 1-11.
Prehaud et al. "Attenuation of Rabies Virulence: Takeover by the Cytoplasmic Domain of its Envelope Protein", Science Signaling, 2010; vol. 3, pp. 1-7.
Lay et al. "Glycoprotein of Nonpathogenic Rabies Viruses is a Major Inducer of Apoptosis in Human Jurkat T Cells", Annals New York Academy of Sciences, 2003; vol. 1010, pp. 577-581.
Gabriella Ugolini "Specificity of Rabies Virus as a Transneuronal Tracer of Motor Networks: Transfer From Hypoglossal Motoneurons to Connected Second-Order and Higher Order Central Nervous System Cell Groups", The Journal of Comparative Neurology, 1995; vol. 356, pp. 457-480.
Sarmento et al. "Glycoprotein-Mediated Induction of Apoptosis Limits the Spread of Attenuated Rabies Viruses in the Central Nervous System of Mice", Journal of NeuroVirology, 2005; vol. 11, pp. 571-581.
G. Ugolini, "Use of Rabies Virus as a Transneuronal Tracer of Neuronal Connections: Implications for the Understanding of Rabies Pathogenesis", Dev Biol. Basel, Karger, 2008; vol. 131, pp. 493-506.
Guigoni et al. "Rabies Virus is not Cytolytic for Rat Spinal Motoneurons in Vitro", Journal of NeuroVirology, 2002; vol. 8, pp. 306-317.
Jackson et al. "Neuronal Apoptosis Does not Play an Important Role in Human Rabies Encephalitis", Journal of NeuroVirology, 2008; vol. 14, pp. 368-375.

(Continued)

*Primary Examiner* — John Ulm
(74) *Attorney, Agent, or Firm* — Miles & Stockbridge, PC

(57) ABSTRACT

The invention demonstrates that, contrary to apoptotic rabies virus G proteins, certain non-apoptotic rabies virus G proteins, such as the G protein of the CVS-NIV strain, have a neurite outgrowth promoting effect. The invention further demonstrates that this neurite outgrowth promoting effect is due to the cytoplasmic tail of said non-apoptotic rabies virus G proteins, more particularly to their PDZ-BS, which shows a single-point mutation compared to the one of apoptotic rabies virus G proteins. The invention provides means for inducing and/or stimulating neurite outgrowth, which are useful in inducing neuron differentiation, for example for the treatment of a neoplasm of the nervous system, as well as in regenerating impaired neurons, for example for the treatment of a neurodegenerative disease, disorder or condition or in the treatment of a microbial infection, or in protecting neurons from neurotoxic agents or oxidative stress.

16 Claims, 33 Drawing Sheets

(56) References Cited

OTHER PUBLICATIONS

Scott et al. "Structural Abnormalities in Neurons are Sufficient to Explain the Clinical Disease and Fatal Outcome of Experimental Rabies in Yellow Fluorescent Protein-Expressing Transgenic Mice", Journal of Virology, 2008; vol. 82. No. 1, pp. 513-521.

Prehaud et al. "Virus Infection Switches TLR-3-Positive Human Neurons to Become Strong Producers of Beta Interferon", Journal of Virology, 2005; vol. 79, No. 20, pp. 12893-12904.

International Search Report of PCT/IB2010/000967 dated Jun. 18, 2010.

European Search Report of EP 09 29 0257 dated Jun. 16, 2009.

International Preliminary Report on Patentability and Written Opinion Based on Application No. PCT/IB2010/000967 Issued October 11, 2011.

International Search Report for PCT/IB2010/00967 Mailed June 18, 2010.

Written Opinion for PCT.IB2010/000967 Completed June 10, 2010.

CVS-NIV
V H P A    H Q
SP  EC  TM  Cyto   G-survival

ERA
I R S V    L E
SP  EC  TM  Cyto   G-death

CVS-cyto death
V H P A    L E
SP  EC  TM  Cyto   G-cyto death

ERA-cyto survival
I R S V    H Q
SP  EC  TM  Cyto   G-cyto survival

FIGURE 2

N.I. undifferentiated    N.I. differentiated    rRABV G-CVS-NIV    rRABV G-ERA

FIGURE 3A

Average Neurite Length in μm

+191%

- N.I. undifferentiated
- N.I. differentiated
- rRABV G-CVS-NIV
- rRABV G-ERA

+db-cAMP

FIGURE 3B

Average Neurite Length in μm

- N.I. differentiated
- rRABV G-CVS-NIV
- rRABV G-CVS-Cyto Death
- rRABV G-ERA
- rRABV G-ERA-Cyto Survival +db-cAMP $p < 0.0001$
ANOVA test

FIGURE 3C

P<0.0001 ANOVA test

- N.I. differentiated
- rRABV G-CVS-NIV
- rRABV G-CVS (LQ)
- rRABV G-CVS (HE)

+db-cAMP

Average Neurite Length in μm

- N.I. -LPA
- N.I. +LPA 10 μM
- N.I. +LPA 30 μM
- N.I. +LPA 50 μM
- rRABV G-CVS-NIV -LPA
- rRABV G-CVS-NIV +LPA 10 μM
- rRABV G-CVS-NIV +LPA 30 μM
- rRABV G-CVS-NIV +LPA 50 μM
- rRABV G-ERA-Cyto Survival -LPA
- rRABV G-ERA-Cyto Survival +LPA10  μM
- rRABV G-ERA-Cyto Survival +LPA30  μM
- rRABV G-ERA-Cyto Survival +LPA50  μM ★ Means are significantly different, ANOVA test    -db-cAMP
▲ Means are not significantly different, ANOVA test

FIGURE 7

▲ Means are not significantly different, Student's *t* test
★ Means are significantly different, Student's *t* test

Nucleotide sequence encoding the protein G of the CVS-NIV strain of Rabies virus (sequence accession number AF 406694, which includes the ATG start codon and the TGA stop codon):

```
   1 atggttcctc aggctctcct gtttgtaccc cttctggttt ttccattgtg ttttgggaaa
  61 ttccctattt acacgatacc agacaagctt ggtccctgga gcccgattga catacatcac
 121 ctcagctgcc caaacaattt ggtagtggag gacgaaggat gcaccaacct gtcagggttc
 181 tcctacatgg aacttaaagt tggatacatc ttagccataa aaatgaacgg gttcacttgc
 241 acaggcgttg tgacggaggc tgaaacctac actaacttcg ttggttatgt cacaaccacg
 301 ttcaaaagaa agcatttccg cccaacacca gatgcatgta gagccgcgta caactggaag
 361 atggccggtg accccagata tgaagagtct ctacacaatc cgtaccctga ctaccactgg
 421 cttcgaactg taaaaaccac caaggagtct ctcgttatca tatctccaag tgtggcagat
 481 ttggacccat atgacagatc ccttcactcg agggtcttcc ctagcgggaa gtgcccagga
 541 gtagcggtgt cttctaccta ctgctccact aaccacgatt acaccatttg gatgcccgag
 601 aatccgagac tagggatgtc ttgtgacatt tttaccaata gtagagggaa gagagcatcc
 661 aaagggagtg agacttgcgg ctttgtagat gaaagaggcc tatataagtc tttaaaagga
 721 gcatgcaaac tcaagttatg tggagttcta ggacttagac ttatggatgg aacatgggtc
 781 gcgatgcaaa catcaaatga aaccaaatgg tgcctcccg atcagttggt gaacctgcac
 841 gactttcgct cagacgaaat tgagcacctt gttgtagagg agttggtcag gaagagagag
 901 gagtgtctgg atgcactaga gtccatcatg acaacaagt cagtgagttt cagacgtctc
 961 agtcatttaa gaaaacttgt ccctgggttt ggaaaagcat ataccatatt caacaagacc
1021 ttgatggaag ccgatgctca ctacaagtca gtcagaactt ggaatgagat cctcccttca
1081 aaagggtgtt taagagttgg ggggaggtgt catcctcatg tgaacggggt gttttcaat
1141 ggtataatat taggacctga cggcaatgtc ttaatcccag agatgcaatc atccctcctc
1201 cagcaacata tggagttgtt ggaatcctcg gttatccccc ttgtgaccc cctggcagac
1261 ccgtctaccg ttttcaagga cggtgacgag gctgaggatt ttgttgaagt tcaccttccc
1321 gatgtgcaca atcaggtctc aggagttgac ttgggtctcc cgaactgggg gaagtatgta
1381 ttactgagtg caggggccct gactgccttg atgttgataa ttttcctgat gacatgttgt
1441 agaagagtca atcgatcaga acctacgcaa cacaatctca gagggacagg gagggaggtg
1501 tcagtcactc cccaaagcgg aagatcata tcttcatggg aatcacacaa gagtgggggt
1561 cagaccagc tgtga                                       SEQ ID NO: 1
```

Sequence of the protein G of the CVS-NIV strain of Rabies virus (virulent strain); 524aa (sequence accession number AF 406694):

```
MVPQALLFVPLLVFPLCFGKFPIYTIPDKLGPWSPIDIHHLSCPNNLVVEDEGCTNLSGFSYMELKVGYILAIKMNGFTCT
GVVTEAETYTNFVGYVTTTFKRKHFRPTPDACRAAYNWKMAGDPRYEESLHNPYPDYHWLRTVKTTKESLVIISPSVADLD
PYDRSLHSRVFPSGKCPGVAVSSTYCSTNHDYTIWMPENPRLGMSCDIFTNSRGKRASKGSETCGFVDERGLYKSLKGACK
LKLCGVLGLRLMDGTWVAMQTSNETKWCPPDQLVNLHDFRSDEIEHLVVEELVRKREECLDALESIMTTKSVSFRRLSHLR
KLVPGFGKAYTIFNKTLMEADAHYKSVRTWNEILPSKGCLRVGGRCHPHVNGVFFNGIILGPDGNVLIPEMQSSLLQQHME
LLESSVIPLVHPLADPSTVFKDGDEAEDFVEVHLPDVHNQVSGVDLGLPNWGKYVLLSAGALTALMLIIFLMTCCRRVNRS
EPTQHNLRGTGREVSVTPQSGKIISSWESHKSGGQTRL                  SEQ ID NO: 2
```

FIGURE 13A

Nucleotide sequence encoding the protein G of the ERA strain of Rabies virus (sequence accession number AF 406693, which includes the ATG start codon and the TGA stop codon):

```
   1 atggttcctc aggctctcct gtttgtaccc cttctggttt ttccattgtg ttttgggaaa
  61 ttccctattt acacgatacc agacaagctt ggtcctgga gcccgattga catacatcac
 121 ctcagctgcc caaacaattt gatagtggag gacgaaggat gcaccaacct gtcagggttc
 181 tcctacatgg aacttaaagt tggatacatc ttagccataa aaatgaacgg gttcacttgc
 241 acaggcgttg tgacggaggc tgaaacctac actaacttcg ttggttatgt cacaaccacg
 301 ttcaaaagaa agcatttccg cccaacacca gatgcatgta gagccgcgta caactggaag
 361 atggccggtg accccagata tgaagagtct ctacacaatc cgtaccctga ctaccgctgg
 421 cttcgaactg taaaaaccac caaggagtct ctcgttatca tatctccaag tgtggcagat
 481 ttggacccat atgacagatc ccttcactcg agggtcttcc ctagcgggaa gtgctcagga
 541 gtagcggtgt cttctaccta ctgctccact aaccacgatt acaccatttg gatgcccgag
 601 aatccgagac tagggatgtc ttgtgacatt tttaccaata gtagagggaa gagagtatcc
 661 aagggagtg agacttgcgg ctttgtagat gaaagaggcc tatataagtc tttaaaagga
 721 gcatgcaaac tcaagttatg tggagttcta ggacttagac ttatggatgg aacatgggtc
 781 gcgatgcaaa catcaaatga aaccaaatgg tgccctcccg atcagttggt gaacctgcac
 841 gactttcgct cagacgaaat tgagcacctt gttgtagagg agttggtcag gaagagagag
 901 gagtgtctgg atgcactaga gtccatcatg acaaccaagt cagtgagttt cagacgtctc
 961 agtcatttaa gaaaacttgt ccctgggttt ggaaaagcat ataccatatt caacaagacc
1021 ttgatggaag ccgatgctca ctacaagtca gtcagaactt ggaatgagat cctcccttca
1081 aaagggtgtt taagagttgg ggggagggtgt catcctcatg tgaacggggt gttttctcaat
1141 ggtataatat taggacctga cggcaatgtc ttaatcccag agatgcaatc atccctcctc
1201 cagcaacata tggagttgtt ggaatcctcg gttatccccc ttgtgcaccc cctggcagac
1261 ccgtctaccg ttttcaagga cggtgacgag gctgaggatt ttgttgaagt tcaccttccc
1321 gatgtgcaca atcaggtctc aggagttgac ttgggtctcc cgaactgggg gaagtatgta
1381 ttactgagtg caggggccct gactgccttg atgttgataa ttttcctgat gacatgttgt
1441 agaagagtca atcgatcaga acctacgcaa ctcaatctca gagggacagg gagggaggtg
1501 tcagtcactc cccaaagcgg gaagatcata tcttcatggg aatcacacaa gagtgggggt
1561 gagaccagac tgtga                                      SEQ ID NO: 3
```

Sequence of the protein G of the ERA strain of Rabies virus (attenuated strain); 524aa (sequence accession number AF 406693):

```
MVPQALLFVPLLVFPLCFGKFPIYTIPDKLGPWSPIDIHHLSCPNNLIVEDEGCTNLSGFSYMELKVGYILAIKMNGFTCT
GVVTEAETYTNFVGYVTTTFKRKHFRPTPDACRAAYNWKMAGDPRYEESLHNPYPDYRWLRTVKTTKESLVIISPSVADLD
PYDRSLHSRVFPSGKCSGVAVSSTYCSTNHDYTIWMPENPRLGMSCDIFTNSRGKRVSKGSETCGFVDERGLYKSLKGACK
LKLCGVLGLRLMDGTWVAMQTSNETKWCPPDQLVNLHDFRSDEIEHLVVEELVRKREECLDALESIMTTKSVSFRRLSHLR
KLVPGFGKAYTIFNKTLMEADAHYKSVRTWNEILPSKGCLRVGGRCHPHVNGVFFNGIILGPDGNVLIPEMQSSLLQQHME
LLESSVIPLVHPLADPSTVFKDGDEAEDFVEVHLPDVHNQVSGVDLGLPNWGKYVLLSAGALTALMLIIFLMTCCRRVNRS
EPTQLNLRGTGREVSVTPQSGKIISSWESHKSGGETRL                             SEQ ID NO: 4
```

FIGURE 13B

```
G-CVS-NIV    1  MVPQALLFVPLLVFPLCFGKFPIYTIPDKLGPWSPIDIHHLSCPNNLVVEDEGCTNLSGF
G-ERA        1  MVPQALLFVPLLVFPLCFGKFPIYTIPDKLGPWSPIDIHHLSCPNNLIVEDEGCTNLSGF
                ************************************************ ***********

G-CVS-NIV   61  SYMELKVGYILAIKMNGFTCTGVVTEAETYTNFVGYVTTTFKRKHFRPTPDACRAAYNWK
G-ERA       61  SYMELKVGYILAIKMNGFTCTGVVTEAETYTNFVGYVTTTFKRKHFRPTPDACRAAYNWK
                ************************************************************

G-CVS-NIV  121  MAGDPRYEESLHNPYPDYHWLRTVKTTKESLVIISPSVADLDPYDRSLHSRVFPSGKCPG
G-ERA      121  MAGDPRYEESLHNPYPDYRWLRTVKTTKESLVIISPSVADLDPYDRSLHSRVFPSGKCSG
                ****************** *************************************** *

G-CVS-NIV  181  VAVSSTYCSTNHDYTIWMPENPRLGMSCDIFTNSRGKRASKGSETCGFVDERGLYKSLKG
G-ERA      181  VAVSSTYCSTNHDYTIWMPENPRLGMSCDIFTNSRGKRVSKGSETCGFVDERGLYKSLKG
                ************************************** *********************

G-CVS-NIV  241  ACKLKLCGVLGLRLMDGTWVAMQTSNETKWCPPDQLVNLHDFRSDEIEHLVVEELVRKRE
G-ERA      241  ACKLKLCGVLGLRLMDGTWVAMQTSNETKWCPPDQLVNLHDFRSDEIEHLVVEELVRKRE
                ************************************************************

G-CVS-NIV  301  ECLDALESIMTTKSVSFRRLSHLRKLVPGFGKAYTIFNKTLMEADAHYKSVRTWNEILPS
G-ERA      301  ECLDALESIMTTKSVSFRRLSHLRKLVPGFGKAYTIFNKTLMEADAHYKSVRTWNEILPS
                ************************************************************

G-CVS-NIV  361  KGCLRVGGRCHPHVNGVFFNGIILGPDGNVLIPEMQSSLLQQHMELLESSVIPLVHPLAD
G-ERA      361  KGCLRVGGRCHPHVNGVFFNGIILGPDGNVLIPEMQSSLLQQHMELLESSVIPLVHPLAD
                ************************************************************

G-CVS-NIV  421  PSTVFKDGDEAEDFVEVHLPDVHNQSGVDLGLPNWGKYVLLSAGALTALMLIIFLMTCC
G-ERA      421  PSTVFKDGDEAEDFVEVHLPDVHNQSGVDLGLPNWGKYVLLSAGALTALMLIIFLMTCC
                ***********************************************************

G-CVS-NIV  481  RRVNRSEPTQHNLRGTGREVSVTPQSGKIISSWESHKSGGQTRL    SEQ ID NO: 2
G-ERA      481  RRVNRSEPTQLNLRGTGREVSVTPQSGKIISSWESHKSGGETRL    SEQ ID NO: 4
                ********** ********************************  *
```

FIGURE 14

Nucleotide sequence encoding the cytoplasmic domain of the G protein of the CVS-NIV strain of Rabies virus (fragment 1441-1572 of the full-length G coding sequence):

```
agaagagtca atcgatcaga acctacgcaa cacaatctca gagggacagg gagggaggtg
tcagtcactc cccaaagcgg gaagatcata tcttcatggg aatcacacaa gagtgggggt
cagaccagac tg                                          SEQ ID NO: 5
```

Sequence of the cytoplasmic domain of the G protein of the CVS-NIV strain of Rabies virus (very last 44 C-terminal aa of the G protein, i.e. fragment 481-524 of the full-length G protein):

RRVNRSEPTQHNLRGTGREVSVTPQSGKIISSWESHKSGGQTRL     SEQ ID NO: 6

Nucleotide sequence encoding the cytoplasmic domain of the G protein of the ERA strain of Rabies virus (fragment 1441-1572 of the full-length G coding sequence):

```
agaagagtca atcgatcaga acctacgcaa ctcaatctca gagggacagg gagggaggtg
tcagtcactc cccaaagcgg gaagatcata tcttcatggg aatcacacaa gagtgggggt
gagaccagac tg                                          SEQ ID NO: 7
```

Sequence of the cytoplasmic domain of the G protein of the ERA strain of Rabies virus (very last 44 C-terminal aa of the G protein, i.e. fragment 481-524 of the full-length G protein):

RRVNRSEPTQLNLRGTGREVSVTPQSGKIISSWESHKSGGETRL     SEQ ID NO: 8

FIGURE 15

Nucleotide sequence encoding the PDZ-BS motif of the protein G of the CVS-NIV strain of Rabies virus (fragment 1561-1572 of the full-length G coding sequence):

cagaccagac tg                        SEQ ID NO: 9

PDZ-BS motif of the protein G of the CVS-NIV strain of Rabies virus (very last 4 C-terminal aa of the G protein, *i.e.*, fragment 521-524 of the full-length G protein):

QTRL                        SEQ ID NO: 10

Nucleotide sequence encoding the PDZ-BS motif of the protein G of the ERA strain of Rabies virus (fragment 1561-1572 of the full-length G coding sequence):

gagaccagac tg                        SEQ ID NO: 11

PDZ-BS motif of the protein G of the ERA strain of Rabies virus (very last 4 C-terminal aa of the G protein, *i.e.*, fragment 521-524 of the full-length G protein):

ETRL                        SEQ ID NO: 12

Generic sequence of the PDZ-BS motif of a rabies virus G protein:
$x_1 - x_2 - x_3 - x_4$, wherein:

$x_1$ is any amino acid, and $x_2$ is T or S or I, and $x_3$ is any amino acid, and $x_4$ is L or V.                   SEQ ID NO: 13

Sequence of the PDZ-BS motif of a non-apoptotic rabies virus G protein:
$x_1 - x_2 - x_3 - x_4$, wherein:

$x_1$ is any amino acid except E ($x_1$ being preferably Q), and $x_2$ is T or S or I (preferably T), and $x_3$ is any amino acid (preferably R), and $x_4$ is L or V (preferably L).          SEQ ID NO: 14

FIGURE 16

88.0% identity in 524 residues overlap; Score: 2509.0; Gap frequency: 0.0%

```
G-NiV      1 MVPQALLFVPLLVFPLCFGKFPIYTIPDKLGPWSPIDIHHLSCPNNLVVEDEGCTNLSGF
G-Gif      1 MVPQVLLFVLLLGFSLCFGKFPIYTIPDKLGPWSPIDIHHLRCPNNLVVEDEGCINLSGF
             **** **** ** * ************************** ************ ****

61 SYMELKVGYILAIKMNGFTCTGVVTEAETYTNFVGYVTTTFKRKHFRPTPDACRAAYNWK
          61 SYMELKVGYISAIKVNGFTCTGVVTEAETYTNFVGYVTTTFKRKHFRPTPDACRAAYNWK
             ********** *** *********************************************

121 MAGDPRYEESLHNPYPDYHWLRTVKTTKESLVIISPSVADLDPYDRSLHSRVFPSGKCPG
         121 MAGDPRYEESLQNPYPDYHWLRTVKTTKESLIIISPSVTDLDPYDKSLHSRVFPGGKCSG
             *********** ******************* ***** ****** ******** *** *

181 VAVSSTYCSTNHDYTIWMPENPRLGMSCDIPTNSRGKRASKGSETCGFVDERGLYKSLKG
         181 ITVSSTYCSTNHDYTIWMPENPRPGTPCDIFTNSRGKRASNGNKTCGFVDERGLYKSLKG
               ******************** *  *** ********* *  **************

241 ACKLKLCGVLGLRLMDGTWVAMQTSNETKWCPPDQLVNLHDFRSDEIEHLVVEELVRKRE
         241 ACRLKLCGVLGLRLMDGTWVAMQTSDETKWCSPDQLVNLHDFRSDEIEHLVVEELVKKRE
             ** ********************* ***** ********************** ** ***

301 ECLDALESIMTTKSVSFRRLSHLRKLVPGFGKAYTIFNKTLMEADAHYKSVRTWNEILPS
         301 ECLDTLESIMTTKSVSFRRLSHLRKLVPGFGKAYTIFNKTLMEADAHYKSVRTWNEIIPS
             **** *********************************************** **

361 KGCLRVGGRCHPHVNGVFFNGIILGPDGNVLIPEMQSSLLQQHMELLESSVIPLVHPLAD
         361 KGCLKVGGRCHPHVNGVFFNGIILGPDDRVLIPEMQSSLLRQHMELLESSVIPLMHPLAD
             **** ********************** ********** ************ *****

421 PSTVFKDGDEAEDFVEVHLPDVHNQVSGVDLGLPNWGKYVLLSAGALTALMLIIPLMTCC
         421 PSTVFKEGDEAEDFVEVHLPDVYKQISGVDLGLPNWGKYVLMTAGAMIGLVLIFSLMTWC
             ****** *************** * *************** ***   * * *** *

481 RRVNRSEPTQHNLRGTGREVSVTPQSGKIISSWESHKSGGQIRL  SEQ ID NO: 2
         481 REANRPESKQRSFGGTGGNVSVTSQSGKVIPSWESYKSGGEIRL  SEQ ID NO: 15
             * ** * *  *

```
CLUSTAL 2.0.10 multiple sequence alignment

G_ACA57830_      MVPQVLLPVPLLGFSLCFGKFPIYTIPDELGPWSPIDIHHLSCPNNLVVEDEGCTNLSEF   60
G_AAC34683_      MVPQVLLPVPLLGFSLCFGKFPIYTIPDKLGPWSPIDIHHLSCPNNLVVEDEGCTNLSEF   60
G_ABV24348_      MVPQVLLPVLLLGFSLCFGKFPIYTIPDKLGPWSPIDIHHLRCPNNLVVEDEGCTNLSEF   60
G-NIV            MVPQALLFVPLLVFPLCFGKFPIYTIPDKLGPWSPIDIHHLSCPNNLVVEDEGCTNLSEF   60
                 ****.***.** .* ************:************ ******************

G_ACA57830_      SYMELKVGYISAIKVNGFTCTGVVTEAETYTNFVGYVTTTFKRKHFRPTPDACRAAYNWK  120
G_AAC34683_      SYMELKVGYISAIKVNGFTCTGVVTEAETYTNFVGYVTTTFKRKHFRPTPDACRAAYNWK  120
G_ABV24348_      SYMELKVGYISAIKVNGFTCTGVVTEAETYTNFVGYVTTTFKRKHFRPTPDACRAAYNWK  120
G-NIV            SYMELKVGYILAIKVNGFTCTGVVTEAETYTNFVGYVTTTFKRKHFRPTPDACRAAYNWK  120
                 **********  ***.************************************

G_ACA57830_      MAGDPRYEESLHNPYPDYHWLRTVRTTKESLIIISPSVTDLDPYDKSLHSRVFPGGKCSG  180
G_AAC34683_      MAGDPRYEESLHNPYPDYHWLRTVRTTKESLIIISPSVTDLDPYDKSLHSRVFPGGKCSG  180
G_ABV24348_      MAGDPRYEESLQNPYPDYHWLRTVRTTKESLIIISPSVTDLDPYDKSLHSRVFPGGKCSG  180
G-NIV            MAGDPRYEESLHNPYPDYHWLRTVKTTKESLVIISPSVADLDPYDRSLHSRVFPSGKCPG  180
                 ***********:***********:******::*******:*****:*******.**.*

G_ACA57830_      ITVSSTYCSTNHDYTIWMPEDPRPRTPCNIFTNSRGKFASKGNKTCGFVDERGLYKSLKG  240
G_AAC34683_      ITVSSTYCSTNHDYTIWMPENPRPRTPCDIFTNSRGKFASKGNKTCGFVDERGLYKSLKG  240
G_ABV24348_      ITVS-TYCSTNHDYTIWMPEDPRPGTPCDIFTNSRGKFASNGNKTCGFVDERGLYKSLKG  239
G-NIV            VAVSSTYCSTNHDYTIWMPSNPRLGMSCDIFTNSRGKFASKGSETCGFVDERGLYKSLKG  240
                 :.**.***************.:**  ..*:********.*.:.****************

G_ACA57830_      ACRLKLCGVLGLRLMDGTWVAMQTSDETKWCPPDQLVNLHDPHSDEIEHLVVEELVKKRE  300
G_AAC34683_      ACRLKLCGVLGLRLMDGTWVAMQTSDETKWCPPDQLVNLHDPRSDEIEHLVVEELVKKRE  300
G_ABV24348_      ACRLKLCGVLGLRLMDGTWVAMQTSDETKWCSPDQLVNLHDPRSNEIEHLVVEDLVKKRE  299
G-NIV            ACRLKLCGVLGLRLMDGTWVAMQTSNETKWCPPDQLVNLEDPRSDEIEHLVVEELVRKRE  300
                 **.***********************.:*** *******:**:*:***** ****:****

G_ACA57830_      ECLDALESIMTTKSVSPRRLSHLRKLVPGFGKAYTIFNKTLMEADAHYKSVRTWNEIIPS  360
G_AAC34683_      ECLDALESIMTTKSVSPRRLSHLRKLVPGFGKAYTIFNKTLMEADAHYKSVRTWNEIIPS  360
G_ABV24348_      ECLDTLESIMTTKSVSPRRLSHLRKLVPGFGKAYTIFNKTLMEADVHYKSVRTWNEIIPS  359
G-NIV            ECLDALESIMTTKSVSPRELSHLRKLVPGFGKAYTIFNKTLMEADAHYKSVRTWNEILPS  360
                 ****:*************:**************************:*********:**

G_ACA57830_      KGCLKVGGRCHPHVNGVFFNGIILGPDGHVLIPEMQSSLLQQHMELLKSSVIPLMHPLAD  420
G_AAC34683_      KGCLKVGGRCHPHVNGVFFNGIILGPDGHVLIPEMQSSLLQQHMELLKSSVIPLMHPLAD  420
G_ABV24348_      KGCLKVGGRCHPHVNGVFFNGIILGPDDRVLIPEMQSSLLRQHMELLESSVIPLMHPLAD  419
G-NIV            KGCLRVGGRCHPHVNGVFFNGIILGPDGNVLIPEMQSSLLQQHMELLESSVIPLVHPLAD  420
                 ****:*********************  ***********.******:******:*****

G_ACA57830_      PSTVFKEGDEAEDFVEVHLPDVYKRISGVDLGLPNWGKYVLMTAGAMIGLVLIFSLMTWC  480
G_AAC34683_      PSTVFKEGDEAEDFVEVHLPDVYKQISGVDLGLPNWGKYVLMTAGAMIGLVLIFSLMTWC  480
G_ABV24348_      PSTVFKEGDEAEDFVEVHLPDVYKKISGVDLGLPNWGKYVLMTAGAMIGLVLIFSLMTWC  479
G-NIV            PSTVFKDGDEAEDFVEVHLPDVHNQVSGVDLGLPNWGKYVLLSAGALTALMLIIFLMTCC  480
                 ******:***************::::***************::***:  :*:**:**:**

G_ACA57830_      RRANRPESKQRSFGGTGRNVSVTSQSGKVIPSWESYKSGGEIRL   524  SEQ ID NO : 16
G_AAC34683_      RRANRPESKQRSFGGTGRNVSVTSQSGKVIPSWESYKSGGEIRL   524  SEQ ID NO : 17
G_ABV24348_      RRANRPESKQRSFGGTGQNVSVTSQSGKVIPSWESYKSGGEIRL   523  SEQ ID NO : 18
G-NIV            RRVNRSEPTQHDLRGTGREVSVTPQSGKIISSWESHKSGGQTRL   524  SEQ ID NO : 2
                 **.**.*. *: : *** :***.****::.****:***: **
```

FIGURE 18

Cytoplasmic fragment of the G protein of the rabies virus
CVS-NIV strain (SEQ ID NO: 6):

RRVNRSEPTQHNLRGTGREVSVTPQSGKIISSWESHKSGGQTRL

Cytoplasmic fragment of the G protein of the rabies virus
CVS-NIV LQ strain (SEQ ID NO: 19):

RRVNRSEPTQLNLRGTGREVSVTPQSGKIISSWESHKSGGQTRL

Cytoplasmic fragment of the G protein of the rabies virus
CVS-NIV strain HE (SEQ ID NO: 20):

RRVNRSEPTQHNLRGTGREVSVTPQSGKIISSWESHKSGGETRL

FIGURE 19

G-CVS domains

G full length:
MVPQALLFVPLLVFPLCFGKFPIYTIPDKLGPWSPIDIHHLSCPNNLVVEDEGCTNLSGFSYMELKVGYILAIKMNGFTCT
GVVTEAETYTNFVGYVTTTFKRKHFRPTPDACRAAYNWKMAGDPRYEESLHNPYPDYHWLRTVKTTKESLVIISPSVADLD
PYDRSLHSRVFPSGKCPGVAVSSTYCSTNHDYTIWMPENPRLGMSCDIFTNSRGKRASKGSETCGFVDERGLYKSLKGACK
LKLCGVLGLRLMDGTWVAMQTSNETKWCPPDQLVNLHDFRSDEIEHLVVEELVRKREECLDALESIMTTKSVSFRRLSHLR
KLVPGFGKAYTIFNKTLMEADAHYKSVRTWNEILPSKGCLRVGGRCHPHVNGVFFNGIILGPDGNVLIPEMQSSLLQQHME
LLESSVIPLVHPLADPSTVFKDGDEAEDFVEVHLPDVHNQVSGVDLGLPNWGKYVLLSAGALTALMLIIFLMTCCRRVNRS
EPTQHNLRGTGREVSVTPQSGKIISSWESHKSGGQTRL (SEQ ID NO: 2)

Signal peptide (SP):
MVPQALLFVPLLVFPLCFG (SEQ ID NO: 21)

Ectodomain (EC):
KFPIYTIPDKLGPWSPIDIHHLSCPNNLVVEDEGCTNLSGFSYMELKVGYILAIKMNGFTCTGVVTEAETYTNFVGYVTTT
FKRKHFRPTPDACRAAYNWKMAGDPRYEESLHNPYPDYHWLRTVKTTKESLVIISPSVADLDPYDRSLHSRVFPSGKCPGV
AVSSTYCSTNHDYTIWMPENPRLGMSCDIFTNSRGKRASKGSETCGFVDERGLYKSLKGACKLKLCGVLGLRLMDGTWVAM
QTSNETKWCPPDQLVNLHDFRSDEIEHLVVEELVRKREECLDALESIMTTKSVSFRRLSHLRKLVPGFGKAYTIFNKTLME
ADAHYKSVRTWNEILPSKGCLRVGGRCHPHVNGVFFNGIILGPDGNVLIPEMQSSLLQQHMELLESSVIPLVHPLADPSTV
FKDGDEAEDFVEVHLPDVHNQVSGVDLGLPNWGK (SEQ ID NO: 22)

Transmembrane domain (TM):
YVLLSAGALTALMLIIFLMTCC (SEQ ID NO: 23)

Cytoplasmic domain (Cyto):
RRVNRSEPTQHNLRGTGREVSVTPQSGKIISSWESHKSGGQTRL (SEQ ID NO: 6)

Amino acids coded by construct inserts:

Amino acid M + SEQ ID NO: 6 =
MRRVNRSEPTQHNLRGTGREVSVTPQSGKIISSWESHKSGGQTRL (SEQ ID NO: 24)

Transmembrane domain of SEQ ID NO: 23 + cytoplasmic domain of SEQ ID NO: 6 =
YVLLSAGALTALMLIIFLMTCCRRVNRSEPTQHNLRGTGREVSVTPQSGKIISSWESHKSGGQTRL (SEQ ID NO: 25)

Two amino acids from the C-terminal end of the ectodomain of G-CVS-NIV (amino acids GK) + transmembrane domain of SEQ ID NO: 23 + cytoplasmic domain of SEQ ID NO: 6 =
GKYVLLSAGALTALMLIIFLMTCCRRVNRSEPTQHNLRGTGREVSVTPQSGKIISSWESHKSGGQTRL (SEQ ID NO: 26)

Signal peptide of SEQ ID NO: 21 + two amino acids from the C-terminal end of the ectodomain of G-CVS-NIV (amino acids GK) + transmembrane domain of SEQ ID NO: 23 + cytoplasmic domain of SEQ ID NO: 6 =
MVPQALLFVPLLVFPLCFGGKYVLLSAGALTALMLIIFLMTCCRRVNRSEPTQHNLRGTGREVSVTPQSGKIISSWESHKS
GGQTRL (SEQ ID NO: 27)

FIGURE 22

CLUSTAL 2.0.12 multiple sequence alignment

```
Gfull           MVPQALLFVPLLVPPLCFGKFPIYTIPDKLGPWSPIDIHHLSCPNNLVVEDEGCTNLSGF 60
GSP2aaTMCyto    MVPQALLFVPLLVPPLCFG----------------------------------------- 19
GCyto           ------------------------------------------------------------

Gfull           SYMELKVGYILAIEMNGFTCTGVVTEAETYTNFVGYVTTTFKFPHFPPTPDACKAAYNWK 120
GSP2aaTMCyto    ------------------------------------------------------------
GCyto           ------------------------------------------------------------

Gfull           MAGDPKYEESLHNPYPDYHWLRTVFTTKESLVIISPSVADLDPYDPSLHSRVPPSGKCPG 180
GSP2aaTMCyto    ------------------------------------------------------------
GCyto           ------------------------------------------------------------

Gfull           VAVSSTYCSTNHDYTIWMPENPRLGMSCDIFTNSKGKKASKGSETCGFVDERGLYFSLKG 240
GSP2aaTMCyto    ------------------------------------------------------------
GCyto           ------------------------------------------------------------

Gfull           ACHLKLCGVLGLRLMDGTWVAMQTSNETKWCPPDQLVNLHDFRSDEIEHLVVEELVRKKE 300
GSP2aaTMCyto    ------------------------------------------------------------
GCyto           ------------------------------------------------------------

Gfull           ECLDALESIMTTKSVSFRRLSHLRKLVPGPGKAYTIFNKTLMEADAHYKSVKTWNEILPS 360
GSP2aaTMCyto    ------------------------------------------------------------
GCyto           ------------------------------------------------------------

Gfull           KGCLRVGGRCHPHVNGVFPNGIILGPDGNVLIPEMQSSLLQQHMELLESSVIPLVHPLAD 420
GSP2aaTMCyto    ------------------------------------------------------------
GCyto           ------------------------------------------------------------

Gfull           PSTVFKDGDEAEDFVEVHLPDVHNQVSGVDLGLPNWGKYVLLSAGALTALMLIIFLMTCC 480
GSP2aaTMCyto    ------------------------------------GKYVLLSAGALTALMLIIFLMTCC 43
GCyto           -----------------------------------------------------------M 1

Gfull           RPVNRSEPTQHNLRGTGKEVSVTPQSGKIISSWESHKSGGQTRL 524   SEQ ID NO: 2
GSP2aaTMCyto    RPVNRSEPTQHNLRGTGKEVSVTPQSGKIISSWESHKSGGQTRL 87    SEQ ID NO: 27
GCyto           RPVNRSEPTQHNLRGTGKEVSVTPQSGKIISSWESHKSGGQTRL 45    SEQ ID NO: 24
                *******************************************
```

FIGURE 23

(SP Signal peptide, EC Extracellular domain, TM Transmembrane domain, Cyto Cytoplasmic domain)

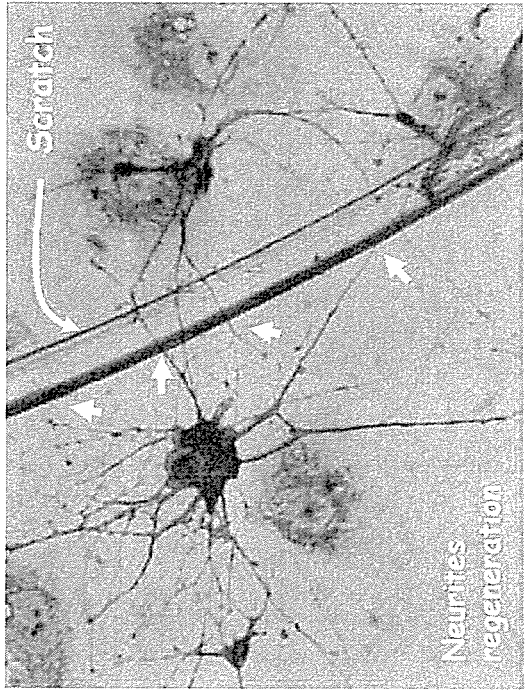
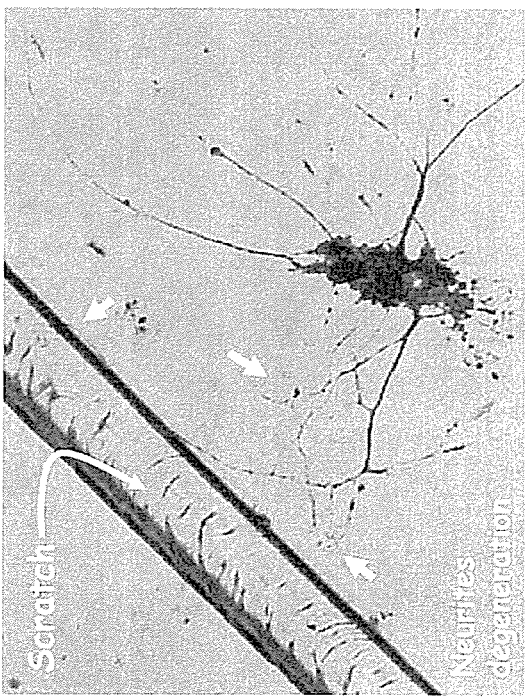
FIGURE 32

NEURON GENERATION, REGENERATION AND PROTECTION

CROSS REFERENCE TO RELATED APPLICATIONS

This application is a §371 National Stage Application of PCT/IB2010/000967, filed Apr. 2, 2010, which claims priority to European Application No. 09290257.6, filed Apr. 7, 2009.

FIELD OF THE INVENTION

The invention relates to neuron generation, regeneration and protection, more particularly to neurite outgrowth.

The invention provides means to induce and/or stimulate neuritogenic effects, which are useful in the medical field, more particularly in the treatment and/or palliation and/or prevention of disorders of the nervous system. More particularly, the invention provides means for inducing and/or stimulating neurite outgrowth, which are useful for inducing neuron differentiation, for example for the treatment of a neoplasm of the nervous system, as well as in regenerating impaired neurons, for example for the treatment of a neurodegenerative disease, disorder or condition or in the treatment of a microbial infection, or in protecting neurons from neurotoxic agents or oxidative stress.

The means of the invention are based on certain non-apoptotic rabies virus G proteins, more particularly on the cytoplasmic tail thereof.

BACKGROUND OF THE INVENTION

During development of the nervous system, neurons extend axons over considerable distances in order to innervate their targets in an appropriate manner. This involves the stimulation in the cells of specific signaling pathways which can stimulate the activity of the growth cone.

While the developing nervous system, more particularly the developing central nervous system, is highly plastic, the adult nervous system, more particularly the adult brain, has more limited repair potential. Therefore, neurite-axon outgrowth and protection against degeneration are important factors to be considered to improve the outcome of a neurodegenerative disease, disorder or condition, such as an acute injury of the nervous system or a chronic neurodegenerative disorder. Products, which would be capable of inducing neurite outgrowth from such neuronal cells, would bring a very useful therapeutic and/or preventive and/or palliative solution to such diseases, disorders or conditions.

At the other side of the neuron developmental process, the proliferation of neuronal progenitors, which do not differentiate into matured neuronal structures, leads to nervous system neoplasm. Products, which would be capable of inducing neurite outgrowth from such progenic cells, would bring a therapeutic and/or preventive and/or palliative solution to such neoplasms.

The general idea on the infection of neuronal cells by a neurotropic virus is that it has no positive impact on neuron morphology, more particularly on neurite outgrowth.

Indeed, there are numerous examples showing that neurotropic viruses cause neuronal cell death by apoptosis. This concerns both DNA viruses, such as herpes viruses, and RNA viruses, either enveloped such as alphaviruses, bunyaviruses and paramyxoviruses, or unenveloped such as picornaviruses and reoviruses.

Rabies virus, more particularly attenuated rabies virus strains, has also been described as inducing neuronal apoptosis.

For example, WO 03/048198 relates to rabies virus G proteins and fragments thereof of at least 100 amino acids, which induce the disruption of the neuronal cell integrity and the formation of apoptotic bodies. These apoptotic bodies are capable of stimulating a humoral immune response, preferably a B-dependent humoral immune response.

WO 03/048198 shows that:
attenuated rabies virus strain (such as the attenuated ERA strain) induces the apoptotic rupture of the cells it infects,
the apoptotic bodies thereby produced stimulate a humoral immune response, more particularly a B-dependent humoral immune response;
induction of apoptosis by a rabies virus strain is determined by the nature of its G-protein;
a rabies virus containing the G protein from an attenuated rabies virus strain (such as the attenuated ERA strain) is able to trigger apoptosis of human cells, whereas expression of the G protein from a pathogenic rabies virus (such as a Challenge Virus Standard—CVS—strain) is not (cf. more particularly example 5 and FIGS. 19 and 20 of WO 03/048198).

Please see also Lay et al. 2003 and Préhaud et al. 2003.

Thus, the G proteins of apoptotic rabies virus strains, such as the G protein of the attenuated ERA strain, are known to be useful in stimulating a humoral response, more particularly a B-dependent humoral immune response.

Since these particular G proteins induce the apoptosis of the cells they infect, they have also been proposed as candidate agents to eliminate undesirable cells by apoptotic rupture of the target cells.

It has also been described that the pathogenicity of a rabies virus strain is inversely correlated with its ability to induce apoptosis (cf. WO 03/048198; Ugolini 1995; Sarmento et al. 2005; Ugolini 2008; Jackson et al. 2008).

Therefore, the more virulent a rabies virus strain is, the less apoptotic.

The findings that virulent rabies virus strains, such as CVS strains, do not induce neuron apoptosis and thereby escape humoral detection explain why virulent rabies virus strains can propagate so extensively within the CNS before the appearance of signs and symptoms of the disease.

Further studies have been conducted to analyze the changes in gene expression pattern that are induced upon infection by a neurotropic virus, such as a rabies virus or herpes simplex type 1 (HSV-1).

These studies have brought the demonstration that postmitotic human neurons, in the absence of glia, have the intrinsic machinery to sense virus infection, and that neurotropic viruses, such pathogenic rabies virus or HSV-1, induce the release of cytokines from post-mitotic human neurons (Préhaud et al. 2005). This cytokine release is believed to further contribute to the escape of neurons from apoptosis and in the consequent spreading of such neurotropic viruses.

Therefore, neuronal cell death mechanisms, as well as the capacity of neurons to raise an immune response upon viral infection, have been thoroughly investigated.

However, less is known about the processes involved in neurogeneration, neuroregeneration and neuroprotection, more particularly in neurite outgrowth from pre-mitotic neurons, such as neuronal progenitors or neoplastic neurons, or from degenerative neurons.

If one focuses on rabies virus, a schematic summary of the current knowledge would be that attenuated rabies virus strains are known to have medical applications due to the apoptosis they induce, and that virulent rabies virus strains are known to not induce apoptosis, but, to the contrary, to preserve the neuronal network, which favors their spreading.

While virulent rabies virus strains have been described as preserving the integrity of the neuronal network, they have also been reported as having a negative impact, or at the very least no positive impact, on neuronal morphology, more particularly on neurite outgrowth.

For example, the publication Guigoni and Coulon 2002 describes that the virulent rabies virus strain CVS-Gif-sur-Yvette do not induce neurite outgrowth from rat motoneurons (cf. for example, FIGS. 5A and 5B of this publication).

Negative impact on neurite outgrowth has also been reported. For example, the publication Scott et al., 2008 has reported that the pathogenic CVS-11 rabies virus strain induces beading of the dendrites and axons, i.e., the formation of vacuoles that are characteristic of a negative stress impact.

The invention provides means for the generation, regeneration and protection of neurons, which derive from certain pathogenic rabies virus strains, and which show surprising and unexpected properties.

SUMMARY OF THE INVENTION

The invention demonstrates that some pathogenic (and non-apoptotic) rabies virus G proteins have a neurite outgrowth promoting effect, i.e., that some non-apoptotic rabies virus G proteins induce and/or stimulate neuritogenesis. This effect is not shown by apoptotic rabies virus G proteins. Neither is it shown by all non-apoptotic rabies virus G proteins.

The inventors identified a sub-group of non-apoptotic (and virulent) rabies virus strains, the G protein of which has a significantly positive effect on neurite outgrowth. As described and illustrated below, a representative strain of this sub-group is the CVS-NIV strain. The G protein of this non-apoptotic (and virulent) strain differs by only 6 amino acid from the G protein of the apoptotic (and attenuated) ERA strain (CNCM I-2760).

The invention further demonstrates that this neurite outgrowth promoting effect is due to the cytoplasmic tail of said non-apoptotic rabies virus G proteins, more particularly to their PDZ binding site (PDZ-BS) and/or to an amino acid which, in the sequence of the G protein of the CVS-NIV strain, is at position 491, more particularly to their PDZ-BS.

The invention relates to polypeptides, which are or derive from certain non-apoptotic rabies virus G proteins, more particularly from their cytoplasmic tail, as well as to nucleic acids, vectors, cells and pharmaceutical compositions or drugs.

The means of the invention are notably useful as neurite outgrowth stimulating and/or inducing agents. They can notably be used for inducing neuron differentiation, for example in the treatment of a neoplasm of the nervous system, as well as for regenerating impaired neurons, for example in the treatment of a neurodegenerative disease, disorder or condition or in the treatment of a microbial infection, or for protecting neurons from neurotoxic agents or oxidative stress.

BRIEF DESCRIPTION OF THE FIGURES

Some of the figures, to which the present application refers, are in color. The application as filed contains the color printout of the figures, which can therefore be accessed by inspection of the file of the application at the patent office.

FIG. 2: schematic structure of the recombinant rabies virus (rRABV) produced by the inventors and used in the examples below.

The G protein of the CVS-NIV strain (non-apoptotic strain) differs by only 6 aa from the G protein of the ERA strain (apoptotic strain).

G-survival=G protein of the CVS-NIV strain
G-death=G protein of the ERA strain
G-cyto death=cytoplasmic tail of G-death in a CVS-NIV G gene background
G-cyto survival=cytoplasmic tail of G-survival in an ERA G gene background
SP=signal peptide
EC: extracellular domain
TM: transmembrane domain
Cyto: cytoplasmic domain FIGS. 3A, 3B, 3C, 3D: the cytoplasmic tail of the G protein of the CVS-NIV strain (non-apoptotic strain) contains a molecular signature promoting neurite outgrowth.

FIG. 3A: neurite outgrowth assay with rRABV G-CVS-NIV and rRABV G-ERA

FIG. 3B: results of the neurite outgrowth assay with db-cAMP with rRABV G-CVS-NIV and rRABV G-ERA FIG. 3C: results of the neurite outgrowth assay without db-cAMP with rRABV G-CVS-NIV, rRABV G-CVS-Cyto Death, rRABV G-ERA and rRABV G-ERA-Cyto Survival FIG. 3D: results of the neurite outgrowth assay with rRABV-G-CVS-NIV, rRABV G-CVS (LQ) and rRABV G-CVS (HE)

Figure 4A:
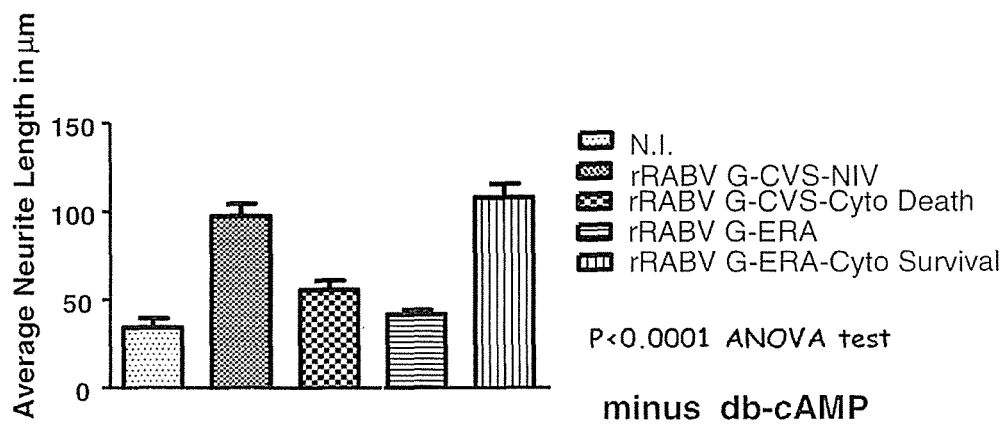
Figure 4B:
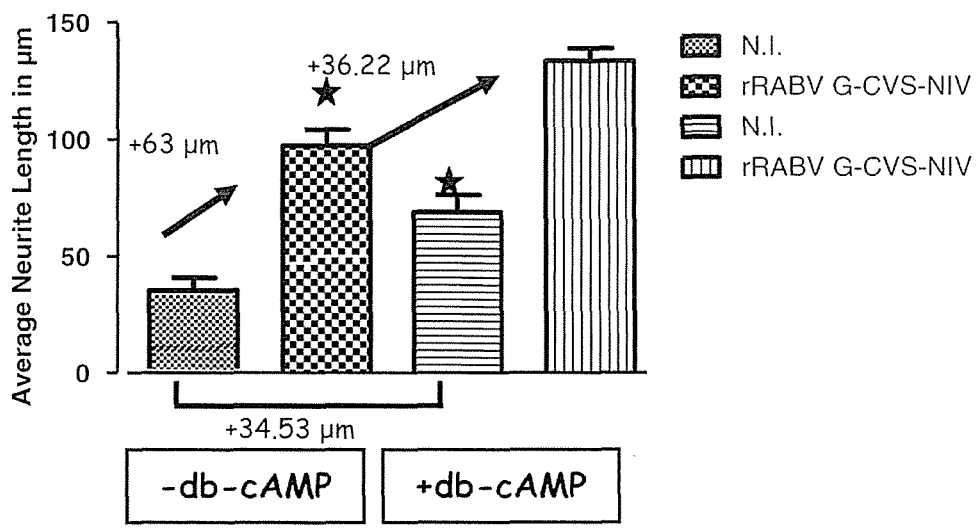

N.I.=non infected
rRABV=recombinant rabies virus
G-CVS or G-CVS-NIV=protein G of the CVS-NIV strain
G-CVS-Cyto Death=cytoplasmic tail of the G protein of the ERA strain in a CVS-NIV G gene background
G-ERA=protein G of the ERA strain
G-ERA-Cyto Survival=cytoplasmic tail of the G protein of the CVS-NIV strain in an ERA G gene background
rRABV G-CVS (LQ)=recombinant rabies virus G protein of the CVS-NIV strain, wherein the amino acid H, which is at position 491 in the full length G protein of the CVS-NIV strain, has been replaced by the amino acid L
rRABV G-CVS (HE)=recombinant rabies virus G protein of the CVS-NIV strain, wherein the amino acid Q, which is at position 521 in the full length G protein of the CVS-NIV strain, has been replaced by the amino acid E FIGS. 4A, 4B: the cytoplasmic tail of the G protein of the CVS-NIV strain (non-apoptotic strain) is an intrinsic effector promoting neuritogenesis, which works synergistically with cAMP*

Figure 6A:
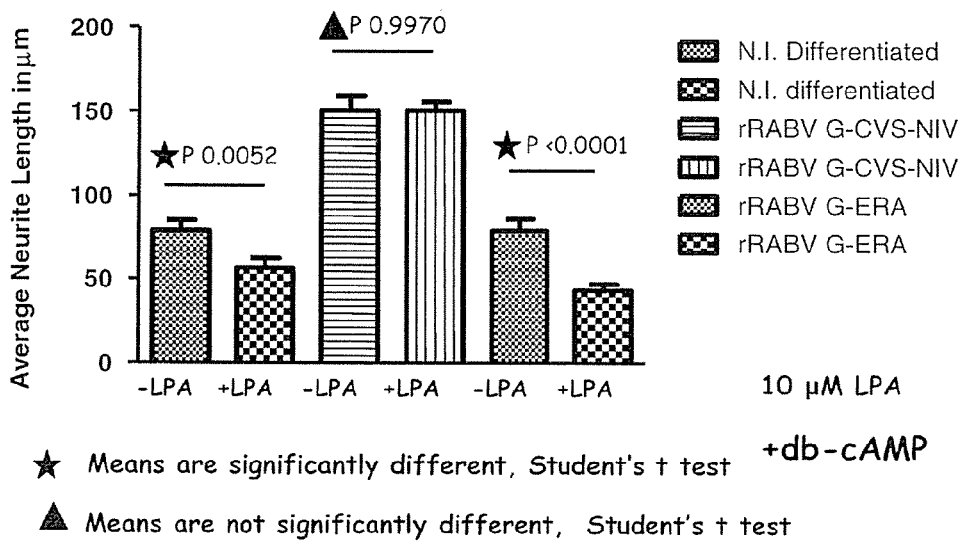
Figure 6B:
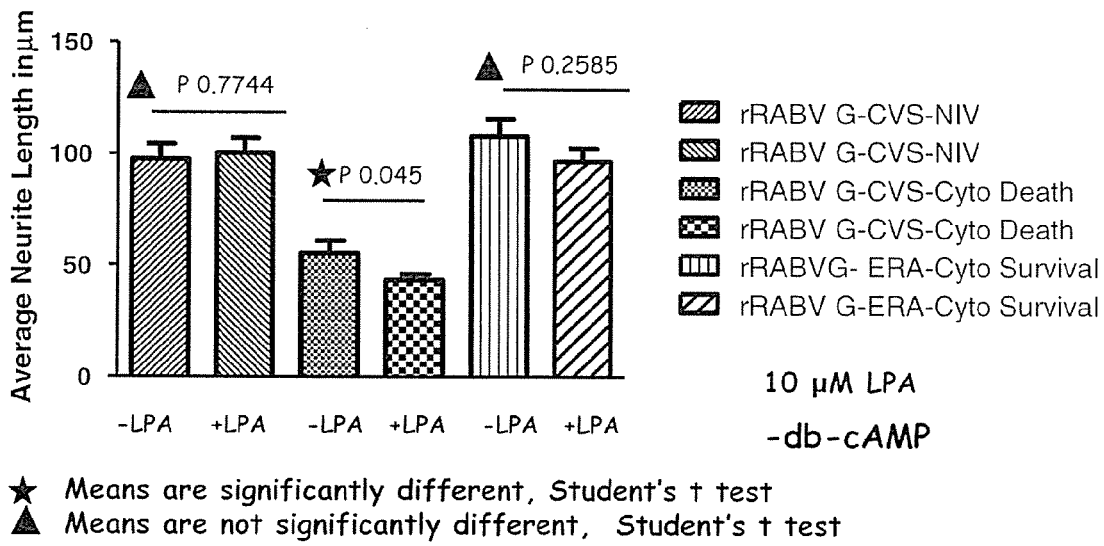
Figure 8:
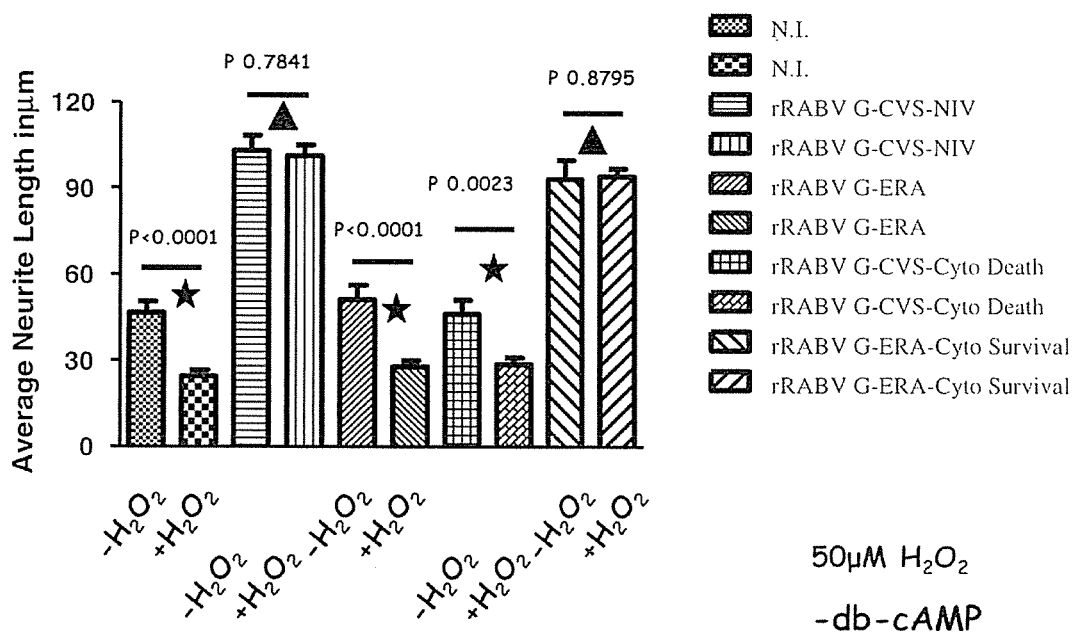
Figure 10A:
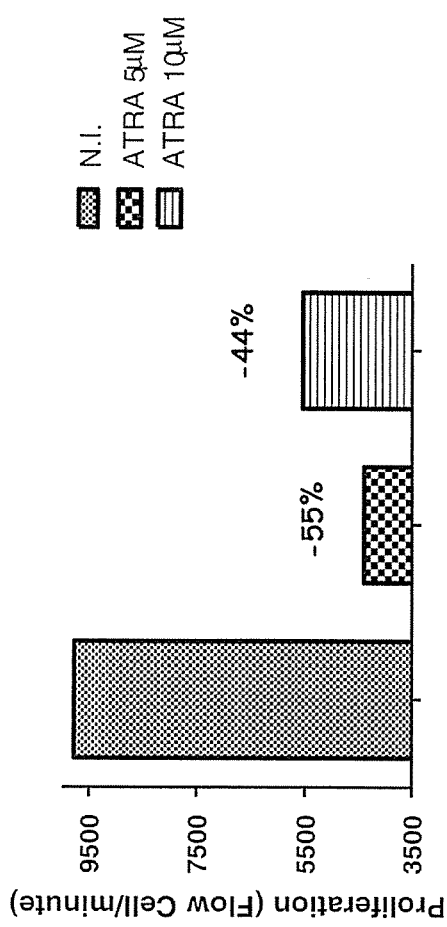
Figure 10B:
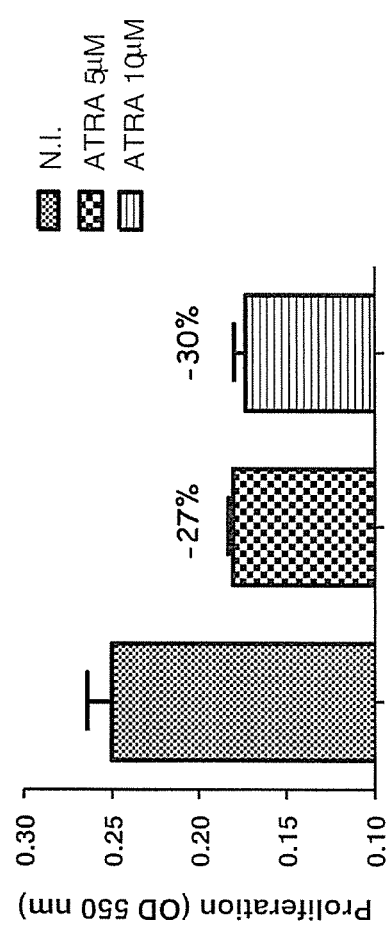

FIG. 4A: without db-cAMP
FIG. 4B: without db-cAMP (first two histograms) and with cAMP (last two histograms)
★ means significantly different (Student's t test with p=0.0067)
N.I.=non infected
rRABV=recombinant rabies virus
G-CVS or G-CVS-NIV=protein G of the CVS-NIV strain
G-CVS-Cyto Death=cytoplasmic tail of the G protein of the ERA strain in a CVS-NIV G gene background
G-ERA=protein G of the ERA strain
G-ERA-Cyto Survival=cytoplasmic tail of the G protein of the CVS-NIV strain in an ERA G gene background FIG. 5: the neuritogenesis effect of the cytoplasmic tail of the G protein of the CVS-NIV strain (non-apoptotic strain) is dependent on the molecular signature and not on the amount of expressed G protein.
  rRABV=recombinant rabies virus
  G-CVS or G-CVS-NIV=protein G of the CVS-NIV strain
  G-CVS-Cyto Death=cytoplasmic tail of the G protein of the ERA strain in a CVS-NIV G gene background
  G-ERA=protein G of the ERA strain
  G-ERA-Cyto Survival=cytoplasmic tail of the G protein of the CVS-NIV strain in an ERA G gene background FIGS. 6A, 6B: the cytoplasmic tail of the G protein of the CVS-NIV strain (non-apoptotic strain) confers neuroprotection against growth cone collapsing drug (LPA)
  FIG. 6A: with db-cAMP
  FIG. 6B: without db-cAMP
  N.I.=non infected
  rRABV=recombinant rabies virus
  G-CVS or G-CVS-NIV=protein G of the CVS-NIV strain
  G-CVS-Cyto Death=cytoplasmic tail of the G protein of the ERA strain in a CVS G gene background
  G-ERA=protein G of the ERA strain
  G-ERA-Cyto Survival=cytoplasmic tail of the G protein of the CVS-NIV strain in an ERA G gene background FIG. 7: the neuroprotection against the growth cone collapsing drug LPA that is induced by the cytoplasmic tail of the G protein of the CVS-NIV strain (non-apoptotic strain) is a robust one.
  ★ means significantly different (ANOVA test)
  ▲ means not significantly different (ANOVA test)
  N.I.=non infected
  rRABV=recombinant rabies virus
  G-CVS-NIV=protein G of the CVS-NIV strain
  G-CVS-Cyto Death=cytoplasmic tail of the G protein of the ERA strain in a CVS-NIV G gene background
  G-ERA=protein G of the ERA strain
  G-ERA-Cyto Survival=cytoplasmic tail of the G protein of the CVS-NIV strain in an ERA G gene background
  LPA=lysophosphatidic acid FIG. 8: the cytoplasmic tail of the G protein of the CVS-NIV strain (non-apoptotic strain) confers neuroprotection against oxidative stress ($H_2O_2$). These experiments were performed without db-cAMP.
  ★ means significantly different (Student's t test)
  ▲ means not significantly different (Student's t test)
  N.I.=non infected
  rRABV=recombinant rabies virus
  G-CVS or G-CVS-NIV=protein G of the CVS-NIV strain
  G-CVS-Cyto Death=cytoplasmic tail of the G protein of the ERA strain in a CVS-NIV G gene background
  G-ERA=protein G of the ERA strain
  G-ERA-Cyto Survival=cytoplasmic tail of the G protein of the CVS-NIV strain in an ERA G gene background FIGS. 9A, 9B, 9C: the cytoplasmic tail of the G protein of the CVS-NIV strain (non-apoptotic strain) confers protection against Herpes Virus Simplex type 1 (HSV-1) cytopathic effect.
  N.I.=non infected
  rRABV=recombinant rabies virus
  G-CVS or G-CVS-NIV=protein G of the CVS-NIV strain
  G-CVS-Cyto Death=cytoplasmic tail of the G protein of the ERA strain in a CVS-NIV G gene background
  G-ERA=protein G of the ERA strain
  G-ERA-Cyto Survival=cytoplasmic tail of the G protein of the CVS-NIV strain in an ERA G gene background FIGS. 10A, 10B: cell proliferation of human neuroblastoma cells treated with the all-trans-retinoic acid (ATRA) pro-differentiative drug (FIG. 10A: flow cytometry; FIG. 10B: MTT assay).
  N.I.=non infected FIGS. 11A, 11B: the cytoplasmic tail of the G protein of the CVS-NIV strain (non-apoptotic strain) confers anti-proliferative properties: cell proliferation (FIG. 11A) and neurite length (FIG. 11B) of human neuroblastoma cells treated with rRABV G-CVS-NIV or rRABV G-ERA
  N.I.=non infected
  rRABV=recombinant rabies virus
  G-CVS-NIV=protein G of the CVS-NIV strain
  G-ERA=protein G of the ERA strain FIGS. 12A, 12B: the cytoplasmic tail of the G protein of the CVS-NIV strain (non-apoptotic strain) confers anti-proliferative properties: cell proliferation of human neuroblastoma cells treated with rRABV G-CVS, rRABV G-ERA, rRABV G-CVS-Cyto death or rRABV G-ERA-Cyto survival (FIG. 12A: flow cytometry; FIG. 12B: MTT assay) (N.I.=non infected)
  N.I.=non infected
  rRABV=recombinant rabies virus
  G-CVS or G-CVS-NIV=protein G of the CVS-NIV strain
  G-CVS-Cyto Death=cytoplasmic tail of the G protein of the ERA strain in a CVS-NIV G gene background
  G-ERA=protein G of the ERA strain
  G-ERA-Cyto Survival=cytoplasmic tail of the G protein of the CVS-NIV strain in an ERA G gene background FIGS. 13A, 13B: nucleic acid and protein sequences of the G protein of the CVS-NIV strain (FIG. 13A) and of the ERA strain (FIG. 13B). In FIG. 13A, the PDZ-BS motif of the G protein of the CVS-NIV strain is underlined (QTRL).
  aa=amino acid FIG. 14: sequence alignment of the G proteins of the CVS-NIV and ERA strains; the G proteins differ by only 6 amino acids (shown in bold in FIG. 14):

TABLE 1

| Position of the amino acid in the sequence of the full length G protein | G protein of the CVS-NIV strain (non-apoptotic strain) | G protein of the ERA strain (apoptotic strain) |
| --- | --- | --- |
| 48 | V | I |
| 139 | H | R |
| 179 | P | S |
| 219 | A | V |
| 491 | H | L |
| 521 | Q | E |

The alignment shown in FIG. 14 has been performed using the following parameters:
Comparison matrix: BLOSUM62
Number of alignments computed: 20
Gap open penalty: 12
Gap extension penalty: 4
The result of this alignment is:
98.9% identity in 524 residues overlap;
Score: 2787.0;
Gap frequency: 0.0%.

FIG. 15: nucleic acid and protein sequences of the cytoplasmic domain of the G protein of the CVS-NIV strain and of the ERA strain. In FIG. 15, the PDZ-BS motif of the G protein of the CVS-NIV strain is underlined (QTRL).
  aa=amino acid FIG. 16: nucleic acid and protein sequences of the PDZ-BS of the G protein of the CVS-NIV strain and of the ERA strain.
  aa=amino acid FIG. 17: alignment of the G protein of the CVS-NIV strain (SEQ ID NO: 2) and of the G protein of the CVS-Gif-sur-Yvette strain (SEQ ID NO: 15).

FIG. 18: alignment of the G protein of the CVS-NIV strain (SEQ ID NO: 2) and of the G proteins of three CVS-11 strains (SEQ ID NO: 16; SEQ ID NO: 17; SEQ ID NO: 18).

FIG. 19: sequence of the cytoplasmic fragment of the G protein of the CVS-NIV strain (SEQ ID NO: 6) and of two conservative variants deriving therefrom (variant sequence A of SEQ ID NO: 19; variant sequence B of SEQ ID NO: 20).

Figure 20:
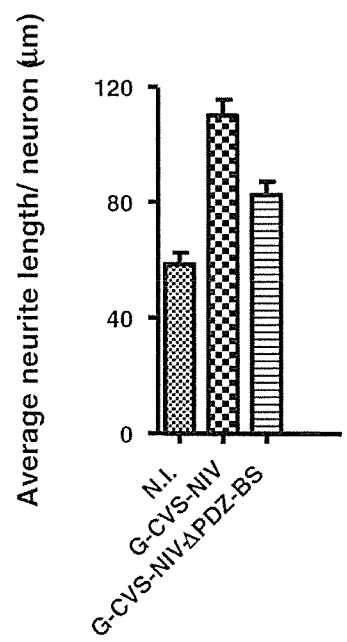

FIG. 20: the deletion of the PDZ-BS affects the neurite outgrowth phenotype (average neurite length in μm at 8 h post-infection, in the presence of db-cAMP).

N.I.=non infected;
G-CVS-NIV=protein G of the CVS-NIV strain;
G-CVS-NIV-DeltaPDZ-BS=protein G of the CVS-NIV strain from which the PDZ-BS has been deleted.

Figure 21:
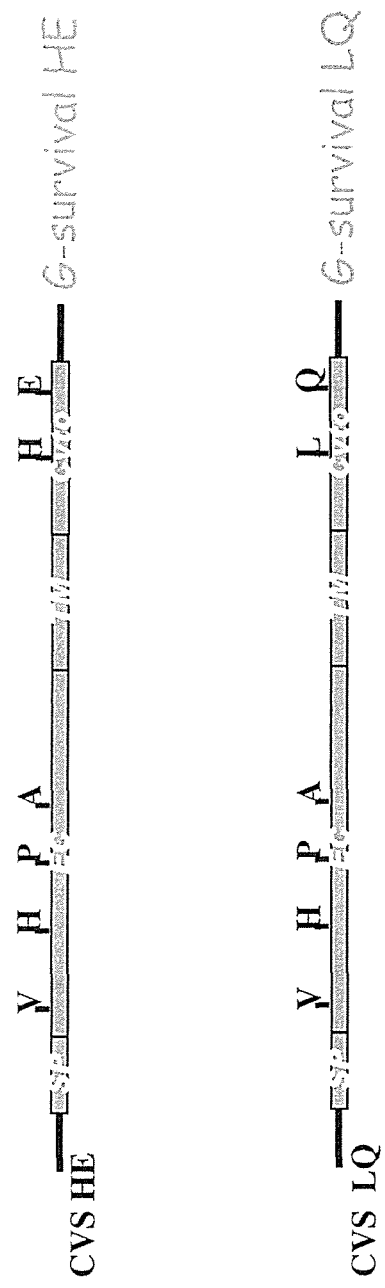

FIG. 21: schematic structure of single-point mutants of the invention (variants B and A). Mutant viruses CVS HE (I-4143) and CVS LQ (I-4142) of the invention differ from CVS-NIV (I-4140) by their G proteins, in which a single-point mutation has been introduced.

CVS HE (variant B)=single-point mutation of the first PDZ-BS amino acid of the G protein CVS-NIV strain, which is E in CVS HE (position 521) instead of Q.

CVS LQ (variant A)=single-point mutation of the amino acid at position 491, which is E instead of Q.
SP: signal peptide
EC: extracellular domain
TM: transmembrane domain
Cyto: cytoplasmic domain FIG. 22: amino acid sequences of domains of the G protein of a non-apoptotic virus strain and of construct inserts
  Sequences of G-CVS domains:
    G full length (SEQ ID NO: 2): full-length G protein of an apoptotic rabies virus strain (CVS-NIV);
    Signal peptide (SP; SEQ ID NO: 21): signal peptide of an apoptotic rabies virus strain (CVS-NIV);
    Ectodomain (EC; SEQ ID NO: 22): ectodomain of an apoptotic rabies virus strain (CVS-NIV);
    Transmembrane domain (TM. SEQ ID NO: 23): transmembrane domain of an apoptotic rabies virus strain (CVS-NIV);
    Cytoplasmic domain (Cyto; SEQ ID NO: 6): cytoplasmic domain of an apoptotic rabies virus strain (CVS-NIV).
  Amino acid sequences coded by construct inserts:
    Amino acid M+SEQ ID NO: 6=SEQ ID NO: 24 (construct G-Cyto);
    Transmembrane domain of SEQ ID NO: 23+cytoplasmic domain of SEQ ID NO: 6=SEQ ID NO: 25;
    Two amino acids from the C-terminal end of the ectodomain of G-CVS-NIV (amino acids GK)+transmembrane domain of SEQ ID NO: 23+cytoplasmic domain of SEQ ID NO: 6=SEQ ID NO: 26;
    Signal peptide of SEQ ID NO: 21+two amino acids from the C-terminal end of the ectodomain of G-CVS-NIV (amino acids GK)+transmembrane domain of SEQ ID NO: 23+cytoplasmic domain of SEQ ID NO: 6=SEQ ID NO: 27 (construct G-(SP-[2a]-TM-Cyto).

FIG. 23: alignment of the amino acid sequences coded by the inserts of three constructs (SEQ ID NO: 2 coded by the G-full construct; SEQ ID NO: 27 coded by the G-(SP)-[2a]-TM-Cyto (=GSP2aaTMCyto) construct; SEQ ID NO: 24 coded by the G-Cyto construct).

Figure 24:
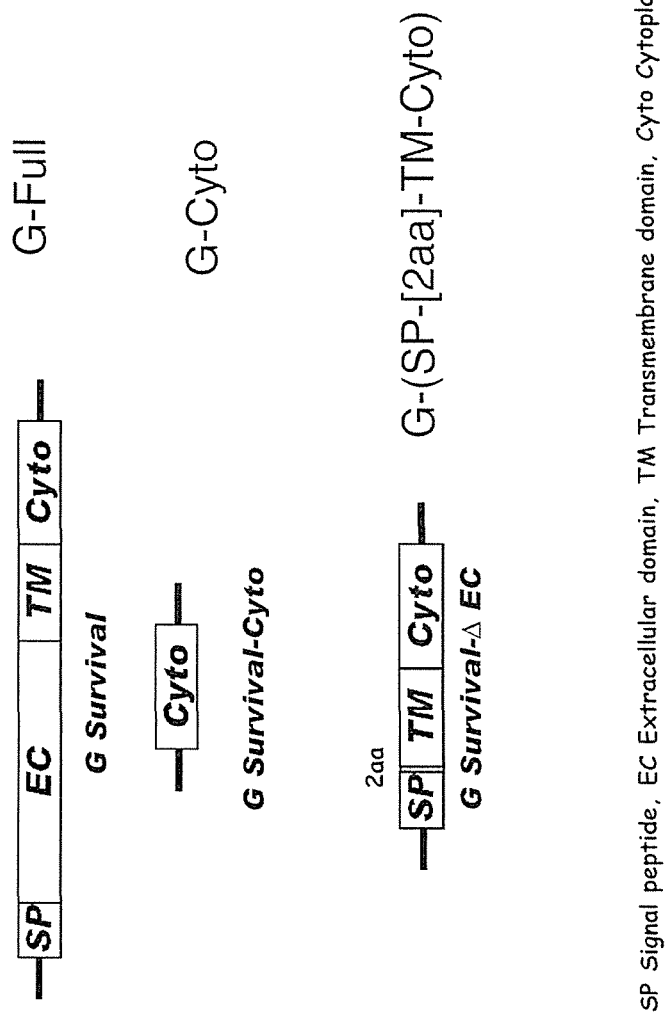

FIG. 24: schematic representation of three RABV G gene constructs (G-full of SEQ ID NO: 2 (=G survival); G-Cyto of SEQ ID NO: 24 (=G survival-Cyto); G-(SP)-[2a]-TM-Cyto of SEQ ID NO: 27 (=G Survival-ΔEC).

Figure 25:
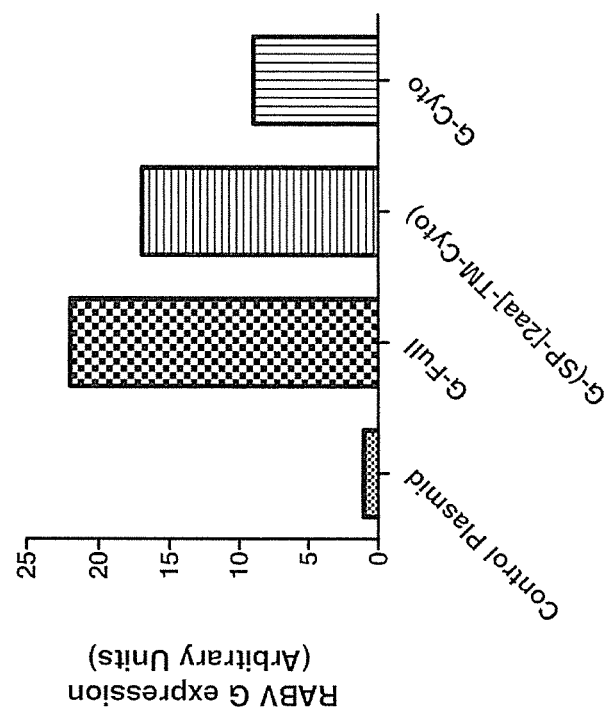

FIG. 25: RABV G expression (arbitrary units) for control plasmid, G-Full construct (SEQ ID NO: 2), G-(SP-[2a]-TM-Cyto) construct (SEQ ID NO: 27), and G-Cyto construct (SEQ ID NO: 24) in the SH-SY5Y cell line (human neuroblastoma cell line).

Figure 27:
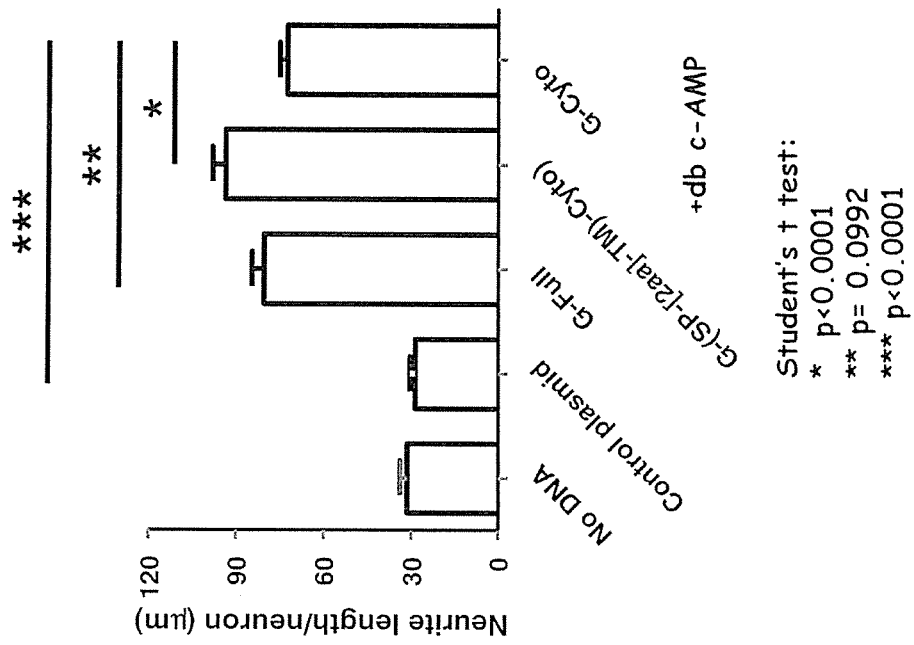
Figure 26:
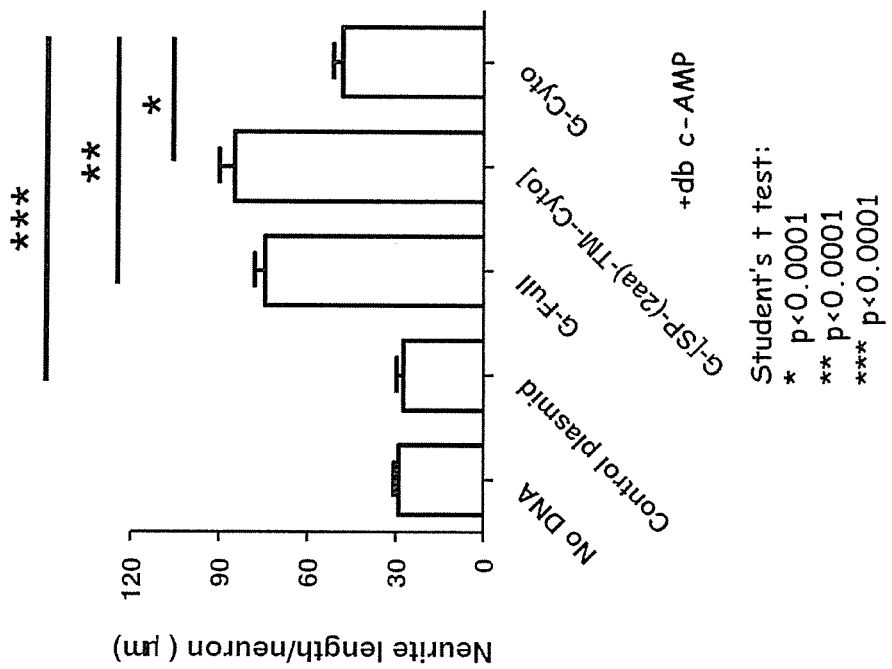

FIGS. 26 and 27: effect on neurite outgrowth of the expression:
  of the full length G protein of a non-apoptotic rabies virus strain (SEQ ID NO: 2; G-Full contruct),
  of the transmembrane and cytoplasmic domains of a non-apoptotic rabies virus strain (SEQ ID NO: 27; G-(SP-[2a]-TM-Cyto) construct), or
  of the cytoplasmic domain of a non-apoptotic rabies virus strain (SEQ ID NO: 24; G-Cyto construct),
  in human neuroblastoma cells (SH-SY5Y cell line in the presence of db c-AMP), compared to control (no DNA) and to the control plasmid.

FIG. 26: transient expression.
FIG. 27: stable expression.

Figure 28:
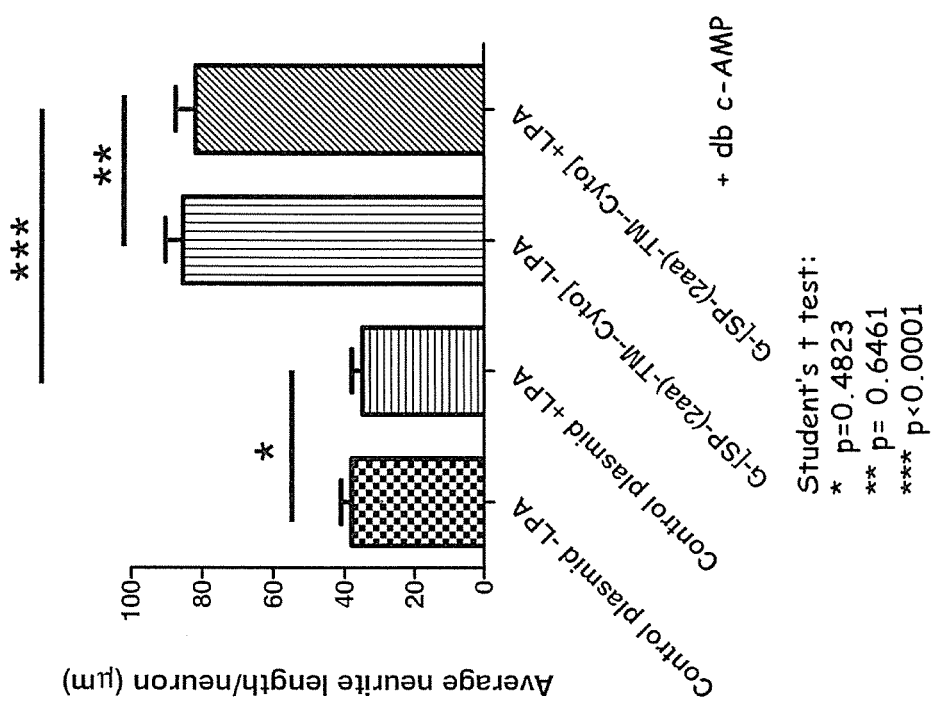

FIG. 28: the expression of the transmembrane and cytoplasmic domains of a non-apoptotic rabies virus strain (SEQ ID NO: 27; construct G-(SP-[2a]-TM-Cyto) induces neurite outgrowth from human neuroblastoma cells (SH-SY5Y cell line in the presence of db c-AMP), and confers protection against the growth cone collapsing drug LPA to the neurites that have grown.

Figure 30:
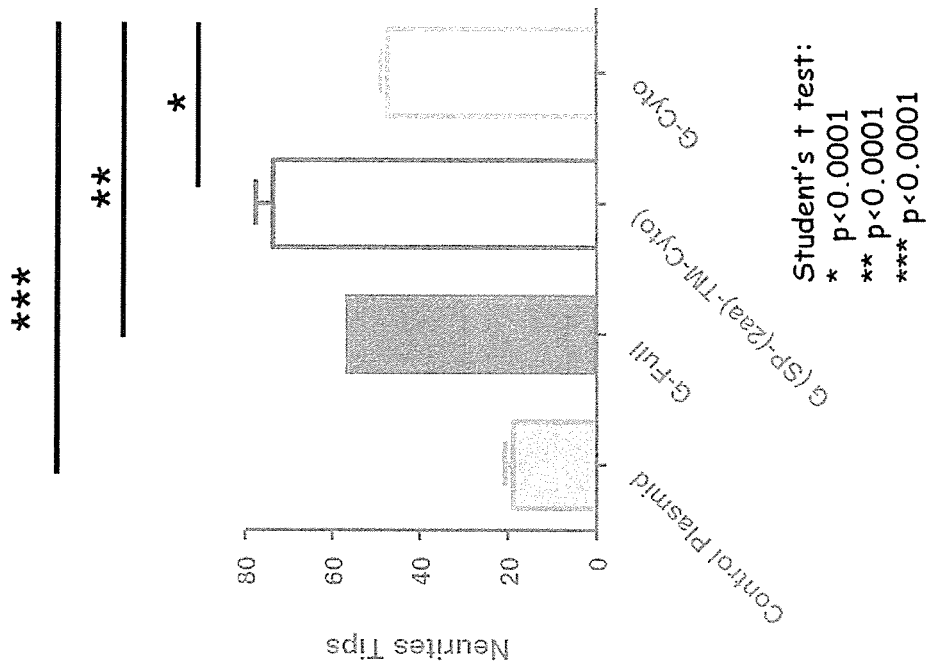
Figure 29:
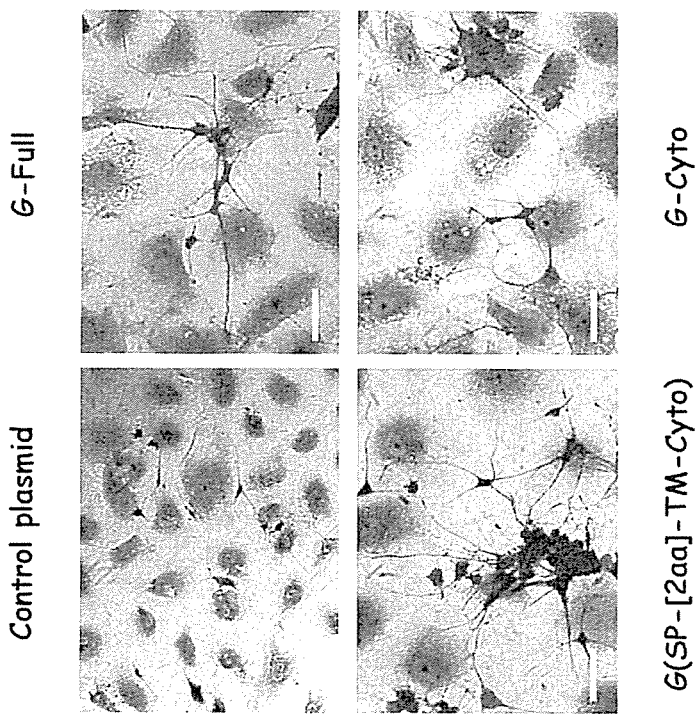

FIGS. 29 and 30: the (stable) expression of the cytoplasmic domain of a non-apoptotic rabies virus strain induces and/or stimulates the differentiation of an embryonic carcinoma cell line (NTera 2cl.-D1; ATCC CRL-1973) into mature post-mitotic human neurons (5 days post differentiation procedure: effect of the G-Full construct—insert of SEQ ID NO: 2—, of the G-(SP-[2a]-TM-Cyto) construct—insert of SEQ ID NO: 27—, or of the G-Cyto construct—insert of SEQ ID NO: 24—, compared to control plasmid).

FIG. 29: colorized images.
FIG. 30: neurite tips.

Figure 31:
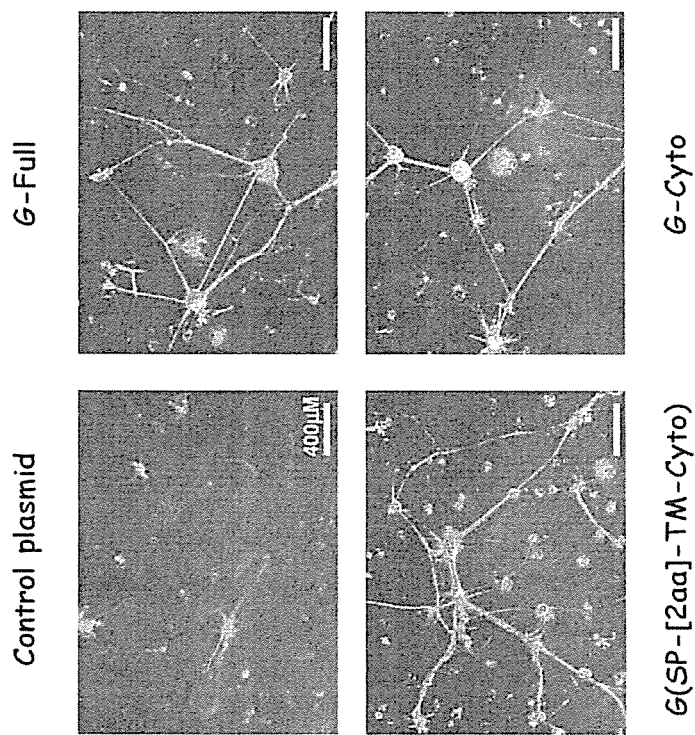

FIG. 31: the (stable) expression of the cytoplasmic domain of a non-apoptotic rabies virus strain induces and/or stimulates the differentiation of an embryonic carcinoma cell line (NTera 2cl.-D1; ATCC CRL-1973) into mature post-mitotic human neurons, and induces and/or stimulates the organisation of a neuronal network with long axons (colorized images of live neurons, 50 days post differentiation procedure: effect of the G-Full construct—insert of SEQ ID NO: 2—, of the G-(SP-[2a]-TM-Cyto) construct—insert of SEQ ID NO: 27—, or of the G-Cyto construct—insert of SEQ ID NO: 24—, compared to control plasmid).

Figure 33:
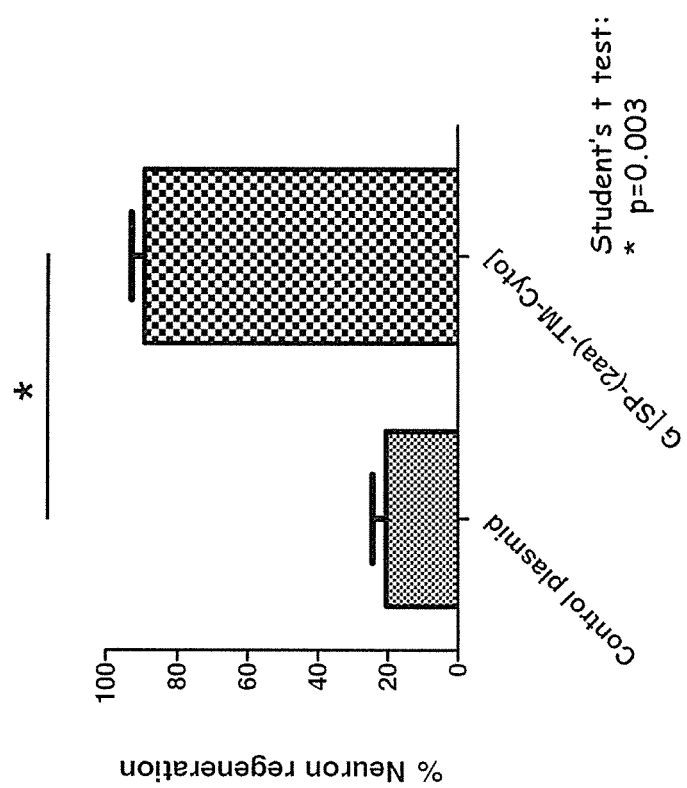

FIGS. 32 and 33: expression of the transmembrane and cytoplasmic domains of a non-apoptotic rabies virus strain induces and/or stimulates the regeneration of wounded mature post-mitotic human neurons (neurons seeded on PDL-laminin plastic ware, 3 days post scratching with injection needle (26GX½", 12-4.5); effect of the polypeptide of SEQ ID NO: 27 (construct G-(SP-[2a]-TM-Cyto)—neurite regeneration—, compared to control plasmid—neurite degeneration—).

FIG. 32: colorized images
FIG. 33: percentage of neurite regeneration

DETAILED DESCRIPTION OF THE INVENTION

The present application relates to the subject-matter as defined in the claims as filed and as herein described and illustrated.

Pathogenicity of rabies virus, a neurotropic virus causing fatal encephalitis in most mammalian species, correlates with the ability of the infected neurons to survive. Attenuation of laboratory strains obtained in search of candidate live vaccine is always linked to the ability of those vaccine strains to trigger cell death.

Subversion of an infected cell by a given virus implies the perturbation of specific signaling pathways.

Rabies virus is an enveloped, bullet-shaped virus belonging to the Rhabdoviridae family and the *Lyssavirus* genus. The viral particle consists of a membrane composed of host lipids and two viral proteins, the G and M proteins, surrounding a helical nucleocapsid (NC). The NC is composed of a viral negative-strand RNA molecule protected by the N protein, the P protein, and the RNA-dependent RNA polymerase, the L protein. The rabies virus proteins are not synthesized in equal amounts in infected cells and are not present at the same ratios in viral particles. Indeed, the N, G and M proteins are, in this order, the most prominent species in virions.

The strategic decision between preservation of the neuronal network integrity (favoring rabies virus spreading) and neuronal cell death (favoring immunogenicity) necessarily involves a choice between at least two signaling networks.

The invention brings the demonstration that the cytoplasmic tail of the G protein of rabies virus strain has a crucial role in the command of the pro-survival (i.e., preservation of the neuronal network integrity, which favors rabies virus spreading) versus pro-apoptotic (i.e., cell death, which favors immunogenicity) decision process.

The invention further uncovers unexpected effects of the pro-survival strategy.

Indeed, the invention shows that the G proteins of some non-apoptotic (and virulent) rabies virus strains, more particularly of the CVS-NIV strain, have a neurite outgrowth promoting effect, i.e., that these non-apoptotic rabies virus G proteins induce and/or stimulate neuritogenesis.

This effect is not shown by apoptotic rabies virus G proteins, such as the G proteins of the ERA and other attenuated rabies virus strains.

Furthermore, this effect is not shown by all apoptotic and/or virulent rabies virus G proteins. More particularly, it is not shown by the G protein of the CVS-Gif-sur-Yvette strain (Préhaud et al. 1988), although this G protein has a high identity score with the G protein of the CVS-NIV strain (cf. FIG. 17). Said effect is not shown by the G proteins of the CVS-11 strains (e.g., ACA57830, AAC34683, ABV24348), although these G proteins also have a high identity score with the G protein of the CVS-NIV strain (cf. FIG. 18). Neither is it shown by the G proteins of the N2C or CVS-24 strains.

Therefore, not all virulent rabies virus strains have a G protein, which shows a significantly positive effect on neurite outgrowth.

Hence, the inventors identified a sub-group of non-apoptotic (and virulent) rabies virus strains, the G protein of which has a significantly positive effect on neurite outgrowth. A representative strain of this sub-group is the CVS-NIV strain. These G proteins may herein be referred to as G proteins of the CVS-NIV type.

The CVS-NIV strain has been deposited at the CNCM on the 1$^{st}$ of Apr. 2009 under deposit number I-4140.

A plasmid expressing the G protein of the CVS-NIV strain has been deposited at the CNCM on the 30$^{th}$ of Nov., 2001 under deposit number I-2578.

The G protein of the CVS-NIV strain has been described in Préhaud et al. 2003.

The sequence of the G protein of the CVS-NIV strain is available under accession number AF 406694.

A sequence of the G protein of the CVS-NIV strain is the sequence of SEQ ID NO: 2 shown in FIG. 13A.

A rabies virus G protein is a type I transmembrane glycoprotein that forms the trimeric spikes of the viral envelope and that is found at the membrane of infected cells. The rabies virus G protein is a 524 amino acid long protein, which consists of an ectodomain, a transmembrane segment and a 44 amino acid long cytoplasmic domain.

The very last 4 amino acids of this C-terminal domain form a PDZ binding site (PDZ-BS).

PDZ (PSD-95, Discs Large, ZO-1) domains form globular structures of 80-100 aa organized into six beta-strands and two alpha helices creating a socket where the C terminal sequence of a partner protein could be inserted.

A PDZ binding site (PDZ-BS) is a 4 amino acid sequence; the PDZ-BS sequence is the sequence of SEQ ID NO: 13:

$x_1$-$x_2$-$x_3$-$x_4$, wherein:

$x_1$ is any amino acid, and
$x_2$ is T or S or I, and
$x_3$ is any amino acid, and
$x_4$ is L or V.

The invention notably demonstrates that it is the cytoplasmic tail of said non-apoptotic rabies virus G proteins of the CVS-NIV type, which is responsible for this neurite outgrowth effect.

The invention further demonstrates that this is notably due to the PDZ-BS that is contained in the cytoplasmic tail of said non-apoptotic rabies virus G proteins of the CVS-NIV type.

The PDZ-BS motif of said non-apoptotic rabies virus G proteins of the CVS-NIV type shows a single-point mutation compared to the one of apoptotic rabies virus G proteins. This single-point mutation concerns the first PDZ-BS amino acid, which is not an E in non-apoptotic rabies virus G proteins.

The invention further demonstrates that the amino acid, which, in the full length non-apoptotic rabies virus G protein sequence of the CVS-NIV strain, is at position 491, also contributes to this neurite outgrowth effect. This amino acid is H in the G protein of the CVS-NIV strain (cf. SEQ ID NO: 2). Position 491 in the full length G protein corresponds to position 11 in the cytoplasmic fragment of this protein (SEQ ID NO: 6 in FIG. 15).

The inventors demonstrate that the amino acids, which, in the full length non-apoptotic rabies virus G protein sequence of the CVS-NIV strain (SEQ ID NO: 2), are at positions 491 and 521, are both important for the neurite outgrowth effect of the invention. More particularly, they show that H (but not L) at position 491 and Q (but not E) at position 521, both favors the neurite outgrowth effect of the invention.

Mutant virus, which differ from the CVS-NIV strain in that their G proteins are H491L single-point mutated or Q521E single point mutated, have been constructed and produced by the inventors (CNCM I-4142 and I-4143).

The H491L mutant G protein still has Q at position 521.
The Q521E mutant G protein still has H at position 491.
Both mutant proteins induce a significantly positive neurite outgrowth effect, although at a lesser extent than the CVS-NIV G protein, which has both H at position 491 and Q at position 521.

The cytoplasmic fragments of these mutant G proteins are shown in FIG. 19 (SEQ ID NO: 19 and SEQ ID NO: 20).

Definition of a Polypeptide of the Invention

The invention relates to a polypeptide, which is:
a polypeptide, which comprises:
the parent sequence selected from the sequence of SEQ ID NO: 6, the cytoplasmic fragment of the G protein of the strain I-4140, the cytoplasmic fragment of the G protein produced by the plasmid I-2578, the cytoplasmic fragment of the G protein of sequence AF406694, the cytoplasmic fragment of the G protein of SEQ ID NO: 2, or a conservative variant sequence of said parent sequence, or a conservative fragment of said parent sequence or of said conservative variant sequence.

Said parent sequences, conservative variant sequences and conservative fragments sequences advantageously have the function of inducing and/or stimulating neurite outgrowth, for example as below illustrated, more particularly neurite outgrowth from human pre-mitotic neurons, e.g., from the human neuroblastoma cell line SH-SY5Y (ATCC CRL-2266; please see example 1 below for illustrative experimental conditions and materials).

The invention more particularly relates to said polypeptide, for use in stimulating and/or inducing neurite outgrowth, more particularly for use in the treatment and/or palliation and/or prevention of a disease, disorder or condition involving an insufficient or impaired neurite outgrowth, more particularly an insufficient or impaired neuritogenesis.

Preferably, the amino acid length of said polypeptide is of less than 100 amino acids, more preferably of less than 90 amino acids.

The sequence of the above-mentioned variant proteins can be a sequence, which does not correspond to any known or identifiable rabies virus G protein.

Indeed, one of average skill in the art will recognize that starting from the sequence of a given rabies virus G protein, one or several amino acid substitution(s) and/or addition(s) and/or deletion(s) can be made, while still retaining the capacity of inducing and/or stimulating neurite outgrowth. Such conservative amino acid substitution(s) and/or addition(s) and/or deletion(s) are herein encompassed.

Without being bound by theory, each of the following eight groups are usually considered as containing amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

Therefore, the above-mentioned variant proteins notably encompass proteins, which have been engineered by man, and which differ from said rabies virus G protein by one or several amino acid substitution(s) and/or addition(s) and/or deletion(s), provided that the resulting variant protein still has the capacity of inducing and/or stimulating neurite outgrowth, more particularly neurite outgrowth from human pre-mitotic neurons, e.g., from the human neuroblastoma cell line SH-SY5Y (ATCC CRL-2266; please see example 1 below for illustrative experimental conditions and materials).

Preferably, said conservative variant sequence is:
a variant sequence of said parent sequence, which:
is of 34 to 54 amino acids,
is at least 94% identical to said parent sequence over the entire length of the shortest of the parent and variant sequences,
comprises a PDZ-BS sequence (preferably the last four C-terminal amino acids), wherein said PDZ-BS sequence is $x_1$-$x_2$-$x_3$-$x_4$, wherein:
$x_1$ is any amino acid except E (preferably Q), and
$x_2$ is T or S or I (preferably not I, more preferably T), and
$x_3$ is any amino acid (preferably R), and
$x_4$ is L or V (preferably L)
(SEQ ID NO: 14),
said variant sequence being referred to as variant sequence A, or a variant sequence of said parent sequence, which:
is of 44 amino acids,
is at least 94% identical to said parent sequence,
comprises a PDZ-BS sequence (preferably the last four C-terminal amino acids), wherein said PDZ-BS sequence is $x_1$-$x_2$-$x_3$-$x_4$, wherein:
$x_1$ is E, and
$x_2$ is T or S or I (preferably not I, more preferably T), and
$x_3$ is any amino acid (preferably R), and
$x_4$ is L or V (preferably L)
(SEQ ID NO: 13 with $x_1$=E),
and
does not comprise the amino acid L at position 11 (preferably comprises the amino acid H at this position),
said variant sequence being referred to as variant sequence B.

Preferably, said sequence identity is of at least 95% (preferably at least 96%, more preferably at least 97%, still more preferably at least 97.5%, even still more preferably at least 98%, most preferably at least 98.5%, still most preferably at least 99%).

More preferably, said conservative variant sequence is a variant sequence A.

Preferably, said conservative fragment is a fragment of at least 34 amino acids, which has retained the PDZ-BS sequence of said parent sequence or of said variant sequence A or of said variant sequence B, respectively For the sake of conciseness, the term "polypeptide" is herein intended as encompassing proteins, and conversely.

This term also encompasses polypeptides (or proteins), which have been modified by post-transcriptional modification and/or by synthetic chemistry, e.g., by adjunction of a non-peptidic chemical group and/or by modification of the tertiary structure of the polypeptide, e.g., by acetylation, acylation, hydroxylation, cyclisation, racemisation, phosphorylation, etc., as long as the resulting modified polypeptide has retained the capacity of inducing and/or stimulating neurite outgrowth, more particularly neurite outgrowth from human pre-mitotic neurons, e.g., from the human neuroblastoma cell line SH-SY5Y (ATCC CRL-2266; please see example 1 below for illustrative experimental conditions and materials).

The polypeptide of the invention advantageously is, on and of its own, neurotropic.

If required or desired, the polypeptide of the invention can nevertheless be coupled to, or fused with an agent that improves its neurotropicity, more particularly its tropicity for brain neurons, such as RVG-9R as described by Kumar et al. 2007.

Amino acid sequences and nucleotide sequences are herein given in accordance with the standard orientation, i.e., from N-terminal end to C-terminal end for amino acid sequences and from 5'-terminal end to 3'-terminal end for nucleotide sequences.

According to an embodiment of the invention, the PDZ-BS sequence of said variant sequence A is QTRL (SEQ ID NO: 10).

According to an embodiment of the invention, said variant sequence A is of 44 amino acids and has the amino acid H or L, preferably H, at position 11.

An illustrative variant sequence A, which is of 44 amino acids and which has the amino acid L at position 11 is the sequence of SEQ ID NO: 19 (cf. FIG. 19).

According to an embodiment of the invention, the PDZ-BS sequence of said variant sequence B is ETRL (SEQ ID NO: 12).

According to an embodiment of the invention, said variant sequence B has the amino acid H at position 11.

An illustrative variant sequence B, which is of 44 amino acids and which has the amino acid H at position 11 is the sequence of SEQ ID NO: 20 (cf. FIG. 19).

According to an embodiment of the invention, said fragment is the fragment 11-44 from the sequence of SEQ ID NO: 6.

A polypeptide of the invention may comprise, or consist of said pro-neurite outgrowth sequence and of the transmembranar part of a G rabies virus protein or any other anchoring means that the person of average skill in the art may find appropriate to anchor the polypeptide on or in the membrane of a cell, such as a cell as below-defined.

A polypeptide of the invention can be inserted into the structure of an engineered antibody, for example a single chain antibody.

According to an embodiment of the invention, said polypeptide is the G protein of a rabies virus strain, or a cytoplasmic fragment thereof (e.g., SEQ ID NO: 6), or a sub-fragment of such a cytoplasmic fragment (e.g., fragment 11-54 of SEQ ID NO: 6). Said rabies virus G protein more preferably is a non-apoptotic rabies virus G protein. For example, said rabies virus strain is the strain deposited at the CNCM under I-4140.

According to an embodiment of the invention, said polypeptide comprises, or consists of, a variant sequence A or B (as above-defined) of such a cytoplasmic fragment or sub-fragment. For example, said polypeptide comprises, or consist of, the cytoplasmic fragment of the G protein of the rabies virus strain deposited at the CNCM under I-4142 or I-4143 (cf. FIG. 21), whose G proteins are single-point mutant proteins of the G protein of the I-4140 strain (cytoplasmic fragments of SEQ ID NO: 19 and 20, respectively; cf. FIG. 19).

CNCM is the Collection Nationale de Cultures de Microorganismes; Institut Pasteur; 28, rue du Docteur Roux; F-75724 Paris Cedex 15; France. Said deposits have been made under the terms of the Budapest Treaty.

Variant Sequence A

A variant sequence A of the invention comprises the sequence of SEQ ID NO: 14, i.e., the sequence $x_1$-$x_2$-$x_3$-$x_4$, wherein:

$x_1$ is any amino acid except E, and
$x_2$ is T or S or I, and
$x_3$ is any amino acid, and
$x_4$ is L or V.

This sequence is a particular PDZ-BS motif. It usually is located at the C-terminal end of the polypeptide, most usually this sequence is the sequence of the very last four C-terminal amino acids of the polypeptide.

Preferably, said amino acid $x_1$ is Q.
Preferably, said amino acid $x_2$ is not I. Preferably it is T.
Preferably, said amino acid $x_3$ is R.
Preferably, said amino acid $x_3$ is L.
Preferably, the sequence of said PDZ-BS motif is the sequence of SEQ ID NO: 14, wherein:
$x_1$ is Q, and
$x_2$ is T or S or I, and
$x_3$ is R, and
$x_4$ is L or V.

Most preferably, the sequence of said PDZ-BS motif is the sequence of SEQ ID NO: 14, wherein:
$x_1$ is Q, and
$x_2$ is T, and
$x_3$ is R, and
$x_4$ is L or V.

Most preferably, the sequence of said PDZ-BS motif is the sequence of SEQ ID NO: 14, wherein:
$x_1$ is Q, and
$x_2$ is T or S or I, and
$x_3$ is R, and
$x_4$ is L.

More preferably, the sequence of said PDZ-BS motif is the sequence of SEQ ID NO: 14, wherein:
$x_1$ is Q, and
$x_2$ is T, and
$x_3$ is R, and
$x_4$ is L,
i.e., it is the sequence of SEQ ID NO: 10 (cf. FIG. 16).

This QTRL sequence is the sequence of the PDZ-BS motif of the G protein of the CVS-NIV strain, said strain being available from the CNCM under deposit number I-4140, and/or of the protein coded by the plasmid available from the CNCM under deposit number I-2758 (recombinant E. coli containing said plasmid), and/or of the protein of SEQ ID NO: 2 (cf. FIG. 13A).

Appropriate conditions for the cultivation of the recombinant E. coli strain containing the plasmid CNCM I-2758 coding for the G protein of CVS-NIV comprise the incubation of said recombinant E. coli strain at 37° C. on a standard LB-TYM growth medium (in the presence of ampicillin); cf. WO 03/048198.

Appropriate conditions for the propagation of the virus I-4140 (recombinant rabies virus) comprise the incubation of said virus at 37° C. under 5% $CO_2$ with BHK-21 cells (subclone BSR) on a DMEM growth medium containing glucose (e.g., 4.5 g/L), sodium pyruvate and glutamax (Invitrogen 31966047) and 5% FBS; cf. example 1 below.

Preferably, a variant sequence A of the invention is of 44 amino acids and has the amino acid H or L, preferably H, at position 11 of its 44aa-sequence.

Illustrative variant A polypeptides notably comprise the G protein of the recombinant rabies virus strain deposited on the $1^{st}$ of Apr., 2009 at the CNCM under deposit number I-4142 (whose G protein is a single-point mutant protein of the G protein of I-4140; cf. FIG. 21), the cytoplasmic fragment thereof and the conservative cytoplasmic sub-fragments thereof.

The I-4142 strain differs from the CVS-NIV strain (CNCM I-4140) in that its G protein has amino acid L at position 491 (position computed with respect to the full length G protein), instead of H (cf. table 2 below and FIG. 3D).

Appropriate conditions for the propagation of the virus I-4142 (recombinant rabies virus) comprise the incubation of said virus at 37° C. under 5% $CO_2$ with BHK-21 cells (subclone BSR) on a DMEM growth medium containing glucose (e.g., 4.5 g/L), sodium pyruvate and glutamax (Invitrogen 31966047) and 5% FBS; cf. example 1 below.

Illustrative variant A polypeptides notably comprise polypeptides comprising the cytoplasmic fragment of SEQ ID NO: 19 or at least one conservative sub-fragment thereof. The sequence of SEQ ID NO: 19 is an illustrative conservative variant of the sequence of SEQ ID NO: 6 (cf. FIG. 19). It stills has a positive neurite outgrowth effect, although at a lesser level than the sequence of SEQ ID NO: 6 (cf. FIG. 3D and associated comments in the examples section).

Variant Sequence B

A variant sequence B of the invention is of 44 amino acids. It comprises the sequence of SEQ ID NO: 13 with $x_1$=E, i.e., the sequence $x_1$-$x_2$-$x_3$-$x_4$, wherein:
 $x_1$ is E, and
 $x_2$ is T or S or I (preferably not I, more preferably T), and
 $x_3$ is any amino acid (preferably R), and
 $x_4$ is L or V (preferably L).

This sequence is a particular PDZ-BS motif. It usually is located at the C-terminal end of the polypeptide, most usually this sequence is the sequence of the very last four C-terminal amino acids of the polypeptide.

Preferably, said sequence of SEQ ID NO: 13 is ETRL (SEQ ID NO: 12).

In a variant sequence B of the invention, the amino acid, which is at position 11, is not L. It is most preferably H.

Illustrative variant B polypeptides notably comprise the G protein of the recombinant rabies virus strain deposited on the 1$^{st}$ of Apr., 2009 at the CNCM under deposit number I-4143 (whose G protein is a single-point mutant protein of the G protein of I-4140; cf. FIG. 21), the cytoplasmic fragment thereof and the conservative cytoplasmic sub-fragments thereof.

The I-4143 strain differs from the CVS-NIV strain (CNCM I-4140) in that its G protein has amino acid E at position 521 (position computed with respect to the full length G protein), instead of Q (cf. table 2 below and FIG. 3D).

Appropriate conditions for the propagation of the virus I-4143 (recombinant rabies virus) comprise the incubation of said virus at 37° C. under 5% $CO_2$ with BHK-21 cells (subclone BSR) on a DMEM growth medium containing glucose (e.g., 4.5 g/L), sodium pyruvate and glutamax (Invitrogen 31966047) and 5% FBS; cf. example 1 below.

Illustrative variant B polypeptides notably comprise polypeptides comprising the cytoplasmic fragment of SEQ ID NO: 20 or at least one conservative sub-fragment thereof. The sequence of SEQ ID NO: 20 is an illustrative conservative variant of the sequence of SEQ ID NO: 6 (cf. FIG. 19). It stills has a positive neurite outgrowth effect, although at a lesser level than the sequence of SEQ ID NO: 6 (cf. FIG. 3D and associated comments in the examples section).

The G proteins of the I-4142 and the I-4143 strains induce a significantly positive neurite outgrowth effect, although this effect is significantly lower than the one of the G protein of the CVS-NIV strain (I-4140); cf. example 1 and FIG. 3D.

Therefore, each of the two amino acid positions contributes to the neurite outgrowth effect, i.e.:
 the amino acid position, which, in the G protein of the CVS-NIV strain, is position 491 (i.e., H in the G protein of the CVS-NIV strain), and
 the amino acid position, which, in the G protein of the CVS-NIV strain, is the first amino acid of the PDZ-BS of the G protein, i.e., position 521 in the G protein of the CVS-NIV strain (i.e., amino acid Q in the G protein of the CVS-NIV strain).

Alternative or Complementary Definition of a Polypeptide of the Invention

A polypeptide of the invention is a pro-neurite outgrowth polypeptide.

A polypeptide of the invention comprises a parent sequence and/or a conservative variant sequence (variant sequence A or B) and/or a conservative fragment sequence as above-defined.

Alternatively or complementarily, a polypeptide of the invention can be defined as being the G protein of a rabies virus strain, or a variant sequence thereof which derives therefrom by one or several amino acid substitution(s) and/or addition(s) and/or deletion(s), or a fragment sequence of such a G protein or variant G protein, more particularly a cytoplasmic fragment or sub-fragment thereof, provided that said polypeptide has the function of inducing and/or stimulating neurite outgrowth, for example as below illustrated, more particularly neurite outgrowth from human pre-mitotic neurons, e.g., from the human neuroblastoma cell line SH-SY5Y (ATCC CRL-2266; please see example 1 below for illustrative experimental conditions and materials).

More particularly, a polypeptide of the invention can alternatively or complementarily be defined as being the G protein of a non-apoptotic rabies virus strain, or a variant sequence thereof which derives therefrom by one or several amino acid substitution(s) and/or addition(s) and/or deletion(s), or a fragment sequence of such a G protein or variant protein, more particularly a cytoplasmic fragment or sub-fragment thereof, provided that said variant sequence or said fragment has retained the function of inducing and/or stimulating neurite outgrowth, for example as below illustrated, more particularly neurite outgrowth from human pre-mitotic neurons, e.g., from the human neuroblastoma cell line SH-SY5Y (ATCC CRL-2266; please see example 1 below for illustrative experimental conditions and materials).

Illustrative pro-neurite outgrowth proteins, which are not the G protein of the CVS-NIV strain and/or which are other than the protein coded by the plasmid available from the CNCM under deposit number I-2758, and/or which are other than the protein of SEQ ID NO: 2, but which still are suitable pro-neurite outgrowth polypeptides notably comprise the G proteins of the recombinant rabies virus strains deposited on the 1$^{st}$ of Apr., 2009 at the CNCM under deposit numbers I-4142 and I-4143.

The I-4142 strain differs from the CVS-NIV strain (CNCM I-4140) in that its G protein has amino acid L at position 491 (position computed with respect to the full length G protein), instead of H (cf. table 2 below and FIG. 3D).

The I-4143 strain differs from the CVS-NIV strain (CNCM I-4140) in that its G protein has amino acid E at position 521 (position computed with respect to the full length G protein), instead of Q (cf. table 2 below and FIG. 3D).

The G proteins of the I-4142 and the I-4143 strains induce a significantly positive neurite outgrowth effect, although this effect is significantly lower than the one of the G protein of the CVS-NIV strain (I-4140).

Therefore, each of the two amino acid positions contributes to the neurite outgrowth effect, i.e.:
 the amino acid position, which, in the G protein of the CVS-NIV strain, is position 491 (i.e., H in the G protein of the CVS-NIV strain), and
 the amino acid position, which, in the G protein of the CVS-NIV strain, is the first amino acid of the PDZ-BS of the G protein, i.e., position 521 in the G protein of the CVS-NIV strain (i.e., amino acid Q in the G protein of the CVS-NIV strain).

Hence, illustrative pro-neurite outgrowth polypeptides comprise the G protein of the I-4142 strain and the G protein of the I-4143 strain, as well as the fragments of these proteins, more particularly the cytoplasmic fragments thereof (SEQ ID NO: 19 and SEQ ID NO: 20 in FIG. 19) and the cytoplasmic sub-fragments thereof, provided that these sub-fragments have retained the function of inducing and/or stimulating neurite outgrowth, for example as below illustrated, more particularly neurite outgrowth from human pre-mitotic neurons, e.g., from the human neuroblastoma cell line SH-SY5Y (ATCC CRL-2266; please see example 1 below for illustrative experimental conditions and materials).

The invention more particularly relates to said polypeptide, for use in stimulating and/or inducing neurite outgrowth, more particularly for use in the treatment and/or palliation and/or prevention of a disease, disorder or condition involving an insufficient or impaired neurite outgrowth, more particularly an insufficient or impaired neuritogenesis.

Preferably, the amino acid length of said polypeptide is of less than 100 amino acids, more preferably of less than 90 amino acids.

The expression "non-apoptotic rabies virus G protein" is herein intended according to its ordinary meaning in the field.

The PDZ-BS of a non-apoptotic rabies virus G protein is of SEQ ID NO: 14.

A non-apoptotic rabies virus G protein can be additionally or alternatively characterized by the fact that its sequence is the sequence of a G protein of a rabies virus strain, and that it does not trigger the apoptosis of human neurons.

Illustrative means to check that a candidate rabies virus G protein is a non-apoptogenic one are known to the person of ordinary skill in the art.

One of the means comprises checking that the rabies virus strain, which comprises this G protein, is a non-apoptotic strain when it infects neurons, more particularly human neurons, such as SK-N-SH neuroblastoma cell line (ATCC HTB11) or the SH-SY5Y neuroblastoma cell line (ATCC CRL-2266), preferably the SK-N-SH neuroblastoma cell line (ATCC HTB11). Such means are notably useful when a naturally-occurring rabies virus strain comprising the candidate G protein is available for analysis.

Other means comprises genetically engineering cells to make them express the candidate G protein, infecting neuron cells with said expressed candidate G protein, and determining that apoptosis is not induced by said infection.

An illustration of such means is described in Préhaud et al. 2003.

Illustrative genetically engineering cells comprise the transgenic Jurkat cell line that is described in Préhaud et al. 2003, more particularly at page 10538 (cf. § "inducible transgenic cell lines").

Illustrative neuron cells comprise the SK-N-SH neuroblastoma cell line (ATCC HTB11) or the SH-SY5Y neuroblastoma cell line (ATCC CRL-2266), preferably the SK-N-SH neuroblastoma cell line (ATCC HTB11).

Illustrative experimental conditions to make the genetically engineering cells infect the neuron cells comprise those described in Préhaud et al. 2003, more particularly at page 10538 (cf. § "inducible transgenic cell lines").

Detection that the rabies virus strain or the genetically engineered cell does not induce the apoptosis of the neurons cells is within the ambit of the person of average skill in the art.

Illustrative means comprise those described in Préhaud et al. 2003 and Préhaud et al. 2005. Illustrative means comprise detecting that no significant DNA fragmentation is induced, e.g., by Hoechst staining (cf. Préhaud et al. 2003, more particularly at page 10538, § "Detection of nuclear fragmentation by Hoechst staining"), and/or by the TUNEL method (cf. Préhaud et al. 2003, more particularly at page 10538 (cf. § "Detection of nuclear fragmentation by the TUNEL method"), and/or by DNA electrophoresis (cf. Préhaud et al. 2005).

Additional or alternate illustrative means to detect that no significant DNA fragmentation is induced comprise the detection that caspase 8 is not activated, e.g., following the procedure described in Préhaud et al. 2003, more particularly at page 10538, § "Detection of caspase activation"), with the proviso that that the neuron cells used should then contain caspase 8, which is the case of the SK-N-SH cell line.

Illustrative values of non significant apoptosis are shown in FIG. 5D of Préhaud et al. 2003: cf. penultimate column with the heading "JrtTA-G-CVS":
only 19% of apoptotic cells as measured by Hoechst staining;
only 4.7% of apoptotic cells as measured by assessment of the activation of caspase 8.

The rabies virus strains which are attenuated strains (i.e., non pathogenic, e.g., non pathogenic when injected intramuscularly in immunocompetent mice), such as the attenuated ERA strain, the RV194-2 strain, the AVO-1 strain, the SN10 strain, the SN-10-SAD strain, the SAG2 strain, are apoptogenic strains.

Those rabies virus strains, which are pathogenic, i.e., in vivo neurovirulent (such as the CVS-NIV strain) are non-apoptotic.

Therefore, a non-apoptogenic rabies virus strain is a pathogenic (neurovirulent) strain (e.g., pathogenic when injected intramuscularly in immunocompetent mice).

The current knowledge is that:
when a non-apoptogenic rabies virus strain infect a human neuron cell, the G protein it encodes accumulates in the cytoplasm of said neuron cell under the form of perinuclear globular structures, and is not diffusively distributed in the cytoplasm of said neuron cell;
and that, to the contrary, when an apoptogenic rabies virus infect a human neuron cell, the G protein it encodes does not accumulate in the cytoplasm of said neuron cell under the form of perinuclear globular structures, but is diffusively distributed in the cytoplasm of said neuron cell.

As above-mentioned and below illustrated, a polypeptide of the invention can be the G protein of a rabies virus strain.

Preferably, said rabies virus G protein is:
i. the G protein of the CVS-NIV strain, said strain being available from the CNCM under deposit number I-4140 (the deposit date being the 1$^{st}$ of Apr., 2009), and/or the protein coded by the plasmid available from the CNCM under deposit number I-2758, (the deposit date being the 30$^{th}$ of Nov., 2001) and/or the protein of SEQ ID NO: 2; or
ii. a variant protein of said rabies virus G protein of i., wherein said variant protein still is a rabies virus G protein, and wherein the sequence of the PDZ-BS motif of said variant rabies virus G protein still is the sequence of SEQ ID NO: 14.

Preferably, said rabies virus G protein is:
i. the G protein of the CVS-NIV strain which is available from the CNCM under deposit number I-4140, and/or the protein coded by the plasmid available from the CNCM under deposit number I-2758, and/or the protein of SEQ ID NO: 2; or
ii. a variant protein of said rabies virus G protein of i., wherein:
said variant protein consists of a sequence which is at least 95% identical (preferably at least 96%, more preferably at least 97%, still more preferably at least 97.5%, even still more preferably at least 98%, most preferably at least 98.5%, still most preferably at least 99%) to the sequence of said rabies virus G protein of i. over the entire length of the sequence of said rabies virus G protein of i., and
the sequence of the PDZ-BS motif of said variant rabies virus G protein is the sequence of SEQ ID NO: 14.

Preferably, said rabies virus G protein is:
i. the G protein of the CVS-NIV strain which is available from the CNCM under deposit number I-4140, and/or the protein coded by the plasmid available from the CNCM under deposit number I-2758, and/or the protein of SEQ ID NO: 2; or
ii. a variant protein of said rabies virus G protein of i., wherein said variant protein still is a rabies virus G protein, and wherein:
said variant protein consists of a sequence which is at least 95% identical (preferably at least 96%, more preferably at least 97%, still more preferably at least 97.5%, even still more preferably at least 98%, most preferably at least 98.5%, still most preferably at least 99%) to the sequence of said rabies virus G protein of i. over the entire length of the sequence of said rabies virus G protein of i., and
the sequence of the PDZ-BS motif of said variant rabies virus G protein is the sequence of SEQ ID NO: 14.

Preferably, said rabies virus G protein is:
i. the G protein of the CVS-NIV strain which is available from the CNCM under deposit number I-4140, and/or the protein coded by the plasmid available from the CNCM under deposit number I-2758, and/or the protein of SEQ ID NO: 2; or
ii. a variant protein of said rabies virus G protein of i., wherein said variant protein still is a rabies virus G protein, and wherein said variant protein consists of a sequence which:
is at least 95% identical (preferably at least 96%, more preferably at least 97%, still more preferably at least 97.5%, even still more preferably at least 98%, most preferably at least 98.5%, still most preferably at least 99%) to the sequence of said rabies virus G protein of i. over the entire length of the sequence of said rabies virus G protein of i., and
has retained the PDZ-BS motif of SEQ ID NO: 14 of said rabies virus G protein of i. and/or contains a PDZ-BS motif, the sequence of which is QTRL (SEQ ID NO: 14 with $x_1=Q$; $x_2=T$; $x_3=R$; $x_4=L$).

Preferably, the amino acid length of said variant rabies virus G protein of ii. does not exceed the length of said rabies virus G protein of i. of more than 50 amino acids.

Preferably, the amino acid length of said variant rabies virus G protein of ii. is no more than 50 amino acid lower than the length of said rabies virus G protein of i., for example of the same length as the sequence of said rabies virus G protein of i.

More preferably, the amino acid length of said variant rabies virus G protein of ii. is comprised is at least the length of said rabies virus G protein of i minus 50 amino acids, and of at most the length of said rabies virus G protein of i. plus 50 amino acids, for example of the same length as the sequence of said rabies virus G protein of i.

Illustrative pro-neurite outgrowth rabies virus G proteins, which are not the G protein of the CVS-NIV strain (I-4140) and/or which are other than the protein coded by the plasmid available from the CNCM under deposit number I-2758, and/or which are other the protein of SEQ ID NO: 2, but which still are suitable pro-neurite outgrowth rabies virus G proteins notably comprise the G proteins of the recombinant rabies virus strain deposited on the 1$^{st}$ of Apr., 2009 at the CNCM under deposit number I-4142.

The I-4142 strain differs from the CVS-NIV strain (CNCM I-4140) in that its G protein has amino acid L at position 491 (position computed with respect to the full length G protein), instead of H (cf. table 2 below and FIG. 3D).

An illustrative fragment of the sequence of SEQ ID NO: 19 (cf. FIG. 19).

Other Sequences that may Additionally be Present

As above-mentioned and below illustrated, a polypeptide of the invention comprises an amino acid sequence, which has an effect of pro-neurite outgrowth (and/or of neurite spouting and/or of axon growth and/or of dendritic tree extension).

As above-mentioned and below illustrated, said pro-neurite outgrowth sequence can be defined as a parent sequence and/or a conservative variant sequence (variant sequence A or B) and/or a conservative fragment sequence as above-defined.

As above-mentioned and below illustrated, said pro-neurite outgrowth sequence can, alternatively or complementarily, be defined as being the sequence of the G protein of a (non-apoptotic) rabies virus strain (e.g., the G protein of CNCM I-4140, I-4142 or I-4143), or a variant sequence thereof, which derives therefrom by one or several amino acid substitution(s) and/or addition(s) and/or deletion(s), or a fragment sequence of such a G protein or variant G protein, more particularly a cytoplasmic fragment or sub-fragment thereof.

Illustrative examples of such fragments of G protein or variant G protein notably comprise those fragments, which have retained the cytoplasmic domain and the transmembrane domain of said G protein or variant G protein.

Such a transmembrane domain notably has the advantage of anchoring the cytoplasmic fragment in intracellular compartment(s) of the cells, more particularly in the endoplasmic reticulum and/or the Golgi membrane of the cells, whereby said cytoplasmic fragment exerts more efficiently its effects of stimulation and/or induction of neurogeneration, neuroregeneration and neuroprotection. Please see examples 4 and 5 below.

Hence, in addition to said pro-neurite outgrowth sequence, a polypeptide of the invention may further comprise a sequence, which anchors said polypeptide in the endoreticulum membrane and/or in the Golgi membrane of cells, more particularly of neuronal cells, more particularly of human neuronal cells, said anchoring sequence being preferably at the N-terminal end of said pro-neurite outgrowth sequence, most preferably directly linked to the first amino acid at the N-terminal end of said pro-neurite outgrowth sequence.

Hence, in addition to said pro-neurite outgrowth sequence, a polypeptide of the invention may further comprise an amino acid sequence, which anchors said polypeptide in the endoreticulum membrane and/or in the Golgi membrane (preferably in the endoreticulum membrane and in the Golgi membrane) of cells, more particularly of neuronal cells, more particularly of human neuronal cells (e.g., the human neuroblastoma cell line SH-SY5Y cell line as described in the examples below, e.g., example 4).

Said anchoring sequence preferably is at the N-terminal end of said sequence of SEQ ID NO: 6 or variant sequence A or variant sequence B. Most preferably, said anchoring sequence is directly or indirectly, preferably directly, linked to the first amino acid at the N-terminal end of said sequence of SEQ ID NO: 6 or of said variant sequence A or of said variant sequence B.

Such an anchoring sequence may e.g., be an amino acid sequence, which has the capacity of anchoring the cytoplasmic domain of SEQ ID NO: 6 in the endoreticulum membrane and/or in the Golgi membrane of cells, more particularly of neuronal cells, more particularly of human neuronal cells (e.g., the human neuroblastoma cell line SH-SY5Y cell line as described in the examples below, e.g., example 4).

Illustrative of such an anchoring sequence is the transmembrane domain sequence of the G protein of a rabies virus strain (e.g., a non-apoptotic rabies virus strain), preferably the transmembrane domain sequence of the G protein of rabies virus CVS-NIV, which is of SEQ ID NO: 23.

Hence, in addition of said sequence of SEQ ID NO: 6 or of said variant sequence A or of said variant sequence B, said polypeptide may further comprise, preferably at the N-terminal end of said sequence of SEQ ID NO: 6 or variant sequence A or variant sequence B, most preferably directly linked to the first amino acid at the N-terminal end of said sequence of SEQ ID NO: 6 or of said variant sequence A or of said variant sequence B:

the sequence of the transmembrane domain of the G protein of a rabies virus strain, more particularly of a non-apoptotic rabies virus strain, or a sequence, which differs from said sequence of rabies virus G transmembrane domain by at least one amino acid substitution and/or deletion and/or addition, preferably by amino acid substitution(s) and/or deletion(s), more preferably by amino acid substitution(s), but which has retained the capacity of anchoring said polypeptide (more particularly the capacity of anchoring the cytoplasmic domain of SEQ ID NO: 6—when said anchoring sequence is directly linked to the first amino acid at the N-terminal end of said sequence of SEQ ID NO: 6—), in the endoreticulum membrane and/or in the Golgi membrane of cells, more particularly of neuronal cells, more particularly of human neuronal cells (e.g., the human neuroblastoma cell line SH-SY5Y cell line as described in the examples below, e.g., example 4).

Hence, in addition to said pro-neurite outgrowth sequence, a polypeptide of the invention may further comprise, preferably at the N-terminal end of said sequence of SEQ ID NO: 6 or variant sequence A or variant sequence B, most preferably directly linked to the first amino acid at the N-terminal end of said sequence of SEQ ID NO: 6 or of said variant sequence A or of said variant sequence B:

the sequence of the transmembrane domain of the G protein of a rabies virus strain, more particularly of a non-apoptotic rabies virus strain, or a sequence, which differs from said sequence of rabies virus G transmembrane domain by at least one amino acid substitution and/or deletion and/or addition, preferably by amino acid substitution(s) and/or deletion(s), more preferably by amino acid substitution(s), but which has retained the capacity of anchoring the polypeptide of SEQ ID NO: 6 (when said anchoring sequence is directly linked to the first amino acid at the N-terminal of said sequence of SEQ ID NO: 6), in the endoreticulum membrane and/or in the Golgi membrane of cells, more particularly of neuronal cells, more particularly of human neuronal cells.

Preferred examples of such anchoring sequences notably comprise:

the sequence of the transmembrane domain of the G protein of a rabies virus strain, more particularly of a non-apoptotic rabies virus strain, still more particularly of the CVS-NIV strain, for example the sequence of SEQ ID NO: 23, or a variant sequence thereof, which is of 18 to 26 amino acids, preferably of 18 to 22 amino acids, more preferably of 22 amino acids, and which is at least 94% identical to said sequence of SEQ ID NO: 23 over the shortest of the two sequences (i.e., over the shortest of SEQ ID NO: 23 and of said variant sequence).

Such an anchoring sequence is particularly useful when it is linked to a pro-neurite outgrowth sequence that is the sequence of SEQ ID NO: 6 or said variant sequence A, more particularly the sequence of SEQ ID NO: 6.

Hence, according to an embodiment of the invention, the amino acid sequence of a polypeptide of the invention comprises, or consists of the sequence of SEQ ID NO: 23 followed by (from N-terminal to C-terminal end) the sequence of SEQ ID NO: 6, wherein one to four amino acids, preferably one amino acid (e.g., M) is/are optionally present between said sequence of SEQ ID NO: 23 and said sequence of SEQ ID NO: 6.

Illustrative of such a polypeptide is the polypeptide of SEQ ID NO: 25.

In addition to said pro-neurite outgrowth sequence, a polypeptide of the invention may further comprise:

a fragment of the ectodomain of the G protein of a rabies virus strain, more particularly of a non-apoptotic rabies virus strain, still more particularly of the CVS-NIV strain, and/or a signal peptide, this signal peptide being preferably the signal peptide of the G protein of a rabies virus strain, more particularly of a non-apoptotic rabies virus strain, still more particularly of the CVS-NIV strain.

Said ectodomain fragment and/or signal peptide may be present in said polypeptide of the invention in addition to said anchoring sequence.

Preferably, when a signal peptide is comprised in said polypeptide, said signal peptide is the first component at the N-terminal end of the polypeptide.

Preferably, when a signal peptide and an ectodomain fragment are comprised in said polypeptide, said ectodomain fragment is comprised in said polypeptide of the invention between said signal peptide and said pro-neurite outgrowth sequence, preferably between said signal peptide and any possibly anchoring sequence that may be comprised in said polypeptide.

According to an embodiment of the invention, a polypeptide of the invention comprises, or consists of, from its N-terminal end to its C-terminal end:

said signal peptide (e.g., SEQ ID NO: 21), said anchoring sequence (e.g., SEQ ID NO: 23) and said pro-neurite outgrowth sequence.

According to another embodiment of the invention, a polypeptide of the invention comprises, or consists of, from its N-terminal end to its C-terminal end:

said signal peptide (e.g., SEQ ID NO: 21), said ectodomain fragment (e.g., the two amino acids GK), said anchoring sequence (e.g., SEQ ID NO: 23) and said pro-neurite outgrowth sequence.

Preferably, said ectodomain fragment is one to four amino acids, more preferably of 2 amino acids.

Preferably, said ectodomain fragment is a fragment of the C-terminal end of said ectodomain, more preferably the last one to four, more particularly the last two amino acids at the C-terminal end of said ectodomain.

Hence, the amino acid sequence of a polypeptide of the invention may further comprise, (directly or indirectly, preferably directly) linked to the first amino acid at the N-terminal end of said anchoring sequence:

one to four amino acids, preferably two amino acids, more preferably one to four amino acids from the C-terminal end of the ectodomain of the G protein of a rabies virus (e.g., a non-apoptotic rabies virus strain), still more preferably the last two amino acids of the C-terminal end of the ectodomain of the G protein of a rabies virus (e.g., a non-apoptotic rabies virus strain), for example amino acids GK.

Examples of such a polypeptide notably comprise the polypeptide of SEQ ID NO: 26 and the polypeptides, which comprise the sequence of SEQ ID NO: 26.

Hence, a polypeptide of the invention may further comprise a signal peptide, preferably the signal peptide of the G protein of a rabies virus strain (e.g., a non-apoptotic rabies virus strain), said peptide sequence being preferably at the N-terminal end of said polypeptide (most preferably at the very N-terminal end of said polypeptide, i.e., in N-term from any anchoring sequence that may be comprised in said polypeptide).

Examples of such a polypeptide notably comprise the polypeptide of SEQ ID NO: 27 and the polypeptides, which comprise the sequence of SEQ ID NO: 27.

Examples Of Preferred Polypeptides

Preferred polypeptides of the invention comprise polypeptides, which are of less than 100 amino acids, more preferably of as few as amino acids as possible while still retaining a neurite outgrowth effect, more preferably of less than 90 amino acids.

Preferred polypeptides of the invention comprise polypeptides, which comprise, or consist of the cytoplasmic fragments of said G proteins, most preferably the cytoplasmic fragment of SEQ ID NO: 6, SEQ ID NO: 19 or SEQ ID NO: 20 (cf. FIG. 19).

Preferred polypeptides of the invention also comprise polypeptides, which comprise, or consist of the 11-44 sub-fragments of these cytoplasmic fragments.

Preferred polypeptides of the invention comprise polypeptides, which, in addition to said pro-neurite outgrowth sequence, comprise at least one anchoring sequence as above-defined (e.g., the anchoring sequence of SEQ ID NO: 23; please see examples 4-6 below).

Nucleic Acids, Vectors and Cells

The invention also relates to any nucleic acid, more particularly to any DNA or RNA, which codes for a polypeptide of the invention, in accordance with the universal genetic code, taking due account of its degeneracy.

As shown in FIG. 15, an illustrative nucleic acid that codes for the cytoplasmic fragment of SEQ ID NO: 6 (i.e., the cytoplasmic fragment of the CVS-NIV strain) is the nucleic acid of SEQ ID NO: 5.

As shown in FIG. 16, an illustrative nucleic acid that codes for the PDZ-BS of SEQ ID NO: 10 (i.e., the PDZ-BS of the CVS-NIV strain) is the nucleic acid of SEQ ID NO: 9.

The invention also relates to any nucleic acid vector, which comprises at least one nucleic acid coding for a polypeptide of the invention. Said vector can be a transfection and/or expression vector.

Said expression vector may further comprise at least one expression signal and/or regulatory sequence upstream and/or downstream of said nucleic acid, such as at least one promoter, or at least one enhancer and at least one promoter, upstream of said nucleic acid. Said expression vector may for example be a plasmid.

Illustrative of such vectors is the plasmid available from the CNCM under deposit number I-2758.

Interestingly, lentivirus vectors, AAV vectors, adeno-virus vectors and Herpes Simplex disabled virus vectors can be used.

Alternatively or complementarily, a nucleic acid of the invention can be coupled to, or otherwise associated with, a dendrimer such as liposomes, or a cationic polymer such as DEAE-dextrane or polyethylenimine, or an inert solid nanoparticle, such as a gold particle, or any other transfection means that the person of average skill in the art may find appropriate.

The invention also relates to any cell, which comprises at least one polypeptide of the invention, and/or at least nucleic acid of the invention and/or at least one vector of the invention.

Said cell preferably is a cell, which has been genetically engineered to comprise said polypeptide and/or nucleic acid and/or vector.

Said cell can be a eukaryotic cell, preferably a mammal cell, for example a human cell or a non-human cell, most preferably a human cell.

Said cell can be a prokaryotic cell, preferably a bacterium, for example *E. coli.*

Said cell can be a virion, provided said virion does not induce any significantly deleterious or undesirable effect to the recipient subject, more particularly to a human patient.

Preferably, said cell is not a human embryonic cell.

Uses

The invention more particularly relates to said polypeptide and/or nucleic acid and/or vector and/or cell, for use in inducing and/or stimulating neurite outgrowth, more particularly in the treatment and/or palliation and/or prevention of a disease, disorder or condition involving an insufficient or impaired neuritogenesis, more particularly an insufficient or impaired neurite outgrowth.

Said use in a non-immunogenic use.

Indeed, those rabies virus G proteins, which are appropriate to the invention, can be defined as non-apoptotic G proteins.

Therefore, the polypeptide of the invention does not induce the formation of apoptotic bodies such as those that have been described in the previously-published PCT international application WO 03/048198.

In accordance with the invention, the polypeptide of the invention is intended as an effector of neurite outgrowth (and/or of axon and/or dendrite development), e.g., for neuron differentiation from neuron progenitors or neoplastic neurons, and/or for neuron regeneration of impaired neurons (both effects being obtained through stimulation of neurite outgrowth).

Therefore, the polypeptide of the invention is not an immunogenic agent or adjuvant, or at the very least it is not used as an immunogenic agent or adjuvant and it is not used under conditions which would enable said polypeptide to act as an immunogenic agent or adjuvant.

More particularly, contrary to the G proteins of apoptotic rabies virus strains, such as the G proteins of the attenuated ERA strain and of the other attenuated rabies virus strains, the polypeptide of the invention does not raise a detectable humoral immune response when it is administered to neurons.

The polypeptide of the invention is not used in a pharmaceutical composition or drug, which would be an immunogenic composition or a vaccine.

Accordingly, the polypeptide of the invention is preferably not coupled to, not fused to and not associated with any antigen, more particularly with any antigen that would be a viral antigen, a tumor antigen, a cell antigen, the over-expression or alteration of which would lead to a pathology such as a neuropathology.

Diseases, Disorders and Conditions

The invention provides polypeptides, nucleic acids, vectors and cells. These products induce and/or stimulate neuritogenesis, more particularly neurite outgrowth, still more particularly human neurite outgrowth.

A product of the invention preferably is a nucleic acid vector of the invention, more particularly a plasmid of the invention.

More particularly, a product of the invention induces and/or stimulates neuritogenesis, more particularly neurite outgrowth from pre-mitotic neurons, neoplastic neurons, neuron progenitors, as well as from impaired neurons.

Therefore, the invention relates to said product, for use as a neurogenerative and/or neuroregenerative and/or neuroprotective agent.

A product of the invention stimulates and/or induces neurite sprouting and/or axon growth and/or dendritic tree extension.

A product of the invention stimulates the activity of the growth cone. Furthermore, it prevents growth cone from collapsing upon contact with a growth collapsing agent, such as LPA or oxidative stress (cf. example 1 below).

A product of the invention consequently stimulates and/or induces synaptogenesis and/or neurotransmission.

A product of the invention is an agent that inhibits the proliferation of neoplastic neurons, more particularly as a neuro-differentiating agent.

A product of the invention is an agent that stimulates neuronal development and/or neuronal regeneration and/or axon growth and/or dendrite development and/or dendritic tree extension and/or neuronal plasticity and/or synaptogenesis and/or neurotransmission.

A product of the invention is an agent that prevents and/or inhibits and/or blocks any kind of neurotoxicity which would lead to neurite retraction and/or growth cone collapse.

A product of the invention is an agent that stimulates and/or induces neurite outgrowth and/or growth cone activity after said neurite and/or cone has been in contact with a neurotoxic agent.

A product of the invention is an agent that prevents and/or inhibits and/or blocks growth cone collapse and/or neurite retraction and/or axodendritic damage or lesion and/or disruption of synaptic integrity and/or loss of neuron connectivity and/or damage to nerve endings and/or neurotransmission impairment.

A product of the invention is a means to induce and/or stimulate neurite outgrowth, which is notably useful:
in inducing neuron differentiation, for example in the treatment and/or palliation and/or prevention of a neoplasm of the nervous system, as well as
in regenerating impaired neurons, more particularly impaired neurites, for example in the treatment and/or palliation and/or prevention of a neurodegenerative disease, disorder or condition, in the treatment and/or palliation and/or prevention of microbial infections of the neurons, or in protecting neurons from neurotoxic agents or oxidative stress.

Therefore, the invention relates to said product, for use in the treatment and/or palliation and/or prevention of any disease, disorder or condition which involves an insufficient or impaired neuritogenesis, more particularly an insufficient or impaired neurite outgrowth.

Said disease, disorder or condition is alternatively or complementarily defined as any disease, disorder or condition involving an unbalanced neuron cell cycle, wherein said neuron cell cycle is unbalanced:
either by excessive or undesired presence of pre-mitotic neurons (more particularly, by insufficient neuron differentiation and/or by excessive or undesired re-entry of post-mitotic neurons into the neuron cell cycle, as is the case when a neoplasm develops in the nervous system),
or by excessive or undesired neuron degeneration, more particularly excessive or undesired neurite degeneration (as is the case for a neurodegenerative disease, disorder or condition, and for certain microbial infection of the neurons).

A product of the invention can be used in the treatment and/or palliation and/or prevention of a disease, disorder or condition, which alters the Central Nervous System (CNS) and/or the Peripheral Nervous System (PNS), for example as a neurorestorative therapy and/or prevention and/or palliation.

The expression "Central Nervous System" or "CNS" is herein intended as meaning the brain and (in case of a vertebrate animal) the spinal cord.

The peripheral nervous system (PNS) is the vast network of spinal and cranial nerves linking the body to the brain and spinal cord. The PNS is subdivided into the autonomic nervous system (sympathetic NS and parasympathetic NS) and the somatic nervous system. The PNS consists of sensory neurons running from stimulus receptors to the CNS and motor neurons running from the CNS to the muscle and glands.

According to an embodiment of the invention, said disease, disorder or condition is or involves a microbial infection of the nervous system, such as a bacterial and/or viral infection, more particularly a viral infection.

Said viral infection can for example be a Herpes Virus Simplex (HSV) infection, more particularly a HSV type 1 infection (which leads to viral encephalopathy).

Said microbial infection can be a viral infection, which does not induce neuron apoptosis, such as a rabies virus infection.

Preferably, said microbial infection is a microbial infection that induces neuron apoptosis, such as poliomyelitis (cf. Blondel et al., 2005).

According to another embodiment of the invention, said disease, disorder or condition is or involves a non-viral disease, disorder or condition, more preferably a non-bacterial and non-viral disease, disorder or condition, still more preferably a non-microbial disease, disorder or condition.

According to an embodiment of the invention, said disease or disorder is or involves a neurodegenerative disease or disorder (for example, a chronic neurodegenerative disease or disorder), such as non-viral encephalopathy, Alzheimer's disease, Parkinson's disease, ALS, Huntington disease, multiple sclerosis (MS) or rare genetic disease.

Preferably, said neurodegenerative disease or disorder is a non-viral disease or disorder, more preferably a non-bacterial and non-viral disease or disorder, still more preferably a non-microbial disorder.

According to an embodiment of the invention, said condition is or involves a neurodegenerative condition, such as aging.

Preferably, said neurodegenerative condition is a non-viral condition, more preferably a non-bacterial and non-viral condition, still more preferably a non-microbial condition.

According to an embodiment of the invention, said disease, disorder or condition is or involves a physical or ischemic injury of the nervous system, such as seizure, stroke, trauma, epilepsy.

Preferably, said physical or ischemic injury is a non-viral disease, disorder or condition, more preferably a non-bacterial and non-viral disease, disorder or condition, still more preferably a non-microbial disease, disorder or condition.

According to an embodiment of the invention, said disease, disorder or condition involves the presence of a chemical neurotoxic agent and/or of an oxidative stress.

Preferably, said disease, disorder or condition is a non-viral disease, disorder or condition, more preferably a non-bacterial and non-viral disease, disorder or condition, still more preferably a non-microbial disease, disorder or condition.

According to an embodiment of the invention, said disease is a neoplasm, more particularly a neoplasm which comprises neoplastic neurons.

The term "neoplasm" is herein more particularly intended as a malignant neoplasm, more particularly a cancer, still more particularly a tumor or a leukaemia, even still more particularly a tumor.

A product of the invention does not act as an immunogenic agent. More particularly, a product of the invention does not act as an immunogenic agent, which would raise a humoral response against tumor antigens.

Preferably, a product of the invention cannot, on and of its own, act as an immunogenic agent. More particularly, a product of the invention cannot, on and of its own, act as an immunogenic agent, which would raise a humoral response against tumor antigens.

A product of the invention acts as an antiproliferative agent.

A product of the invention induces and/or stimulates the neurite outgrowth from neoplastic neurons, thereby inducing and/or stimulating the differentiation of neoplastic neurons into mature neurons.

Said neoplasm can be a neoplasm of the CNS and/or PNS, preferably a ganglioglioma, a brain tumor, a central neurocytoma, a medulloblastoma, an ependymoma, a teratoma, a neuroblastoma.

Preferably, said neoplasm is a non-viral neoplasm, more preferably a non-bacterial and non-viral neoplasm, still more preferably a non-microbial neoplasm Any administration mode that the skilled person may find appropriate is encompassed by the present invention.

Depending on how the product of the invention is formulated, it can administered by parenteral or enteral (e.g., oral) administration, preferably by parenteral administration, more preferably by parenteral injection.

Pharmaceutical Composition or Drug; Method of Treatment

The invention also relates to any pharmaceutical composition or drug, which comprises at least one polypeptide of the invention and/or at least nucleic acid of the invention and/or at least one vector of the invention and/or at least one cell of the invention.

The pharmaceutical composition or drug of the invention can be used for the treatment and/or palliation and/or prevention of a disease, disorder or condition involving an insufficient or impaired neurite outgrowth as above-described in more details.

The pharmaceutical composition or drug of the invention is not an immunogenic composition and is not a vaccine.

The pharmaceutical composition or drug of the invention may further comprise at least one pharmaceutically and/or physiologically acceptable vehicle (diluent, excipient, additive, pH adjuster, emulsifier or dispersing agent, preservative, surfactant, gelling agent, as well as buffering and other stabilizing and solubilizing agent, etc.).

The pharmaceutical composition or drug of the invention does preferably not contain any immune adjuvant.

Most preferably, the pharmaceutical composition or drug of the invention does not comprise any antigen, more particularly any antigen that would be a viral antigen, a tumor antigen, a cell antigen, the over-expression or alteration of which would lead to a pathology such as a neuropathology.

The pharmaceutical composition or drug of the invention can for example be a liquid solution, suspension, emulsion, tablet, pill, capsule, sustained release formulation, or powder. Preferably, it is formulated under a form suitable for parenteral administration.

The invention also relates to a method of treatment of a subject, more particularly of a human being, in need thereof, which comprises administering to said subject or human being at least one polypeptide of the invention and/or at least nucleic acid of the invention and/or at least one vector of the invention and/or at least one cell of the invention as above-described.

In the application, the term "comprising", which is synonymous with "including" or "containing", is open-ended, and does not exclude additional, unrecited element(s), ingredient(s) or method step(s), whereas the term "consisting of" is a closed term, which excludes any additional element, step, or ingredient which is not explicitly recited.

The term "essentially consisting of" is a partially open term, which does not exclude additional, unrecited element(s), step(s), or ingredient(s), as long as these additional element(s), step(s) or ingredient(s) do not materially affect the basic and novel properties of the invention.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the present application, meant as more particularly encompassing the term "consisting of" ("consist(s) of"), and the term "essentially consisting of" ("essentially consist(s) of").

Each of the relevant disclosures of all references cited herein is specifically incorporated by reference. The following examples are offered by way of illustration, and not by way of limitation.

EXAMPLES

Example 1

The Cytoplasmic Domain of the Protein G of the Non-Apoptotic CVS-NIV Rabies Virus Strain (Cytoplasmic Domain of G-CVS-NIV or of "G-Survival") Induces Neurite Outgrowth, and the Induced Neurite Outgrowth is Highly Resistant to Growth Cone Collapsing Agent (i.e., LPA) and to Oxidative Stress ($H_2O_2$)

Figure 1:
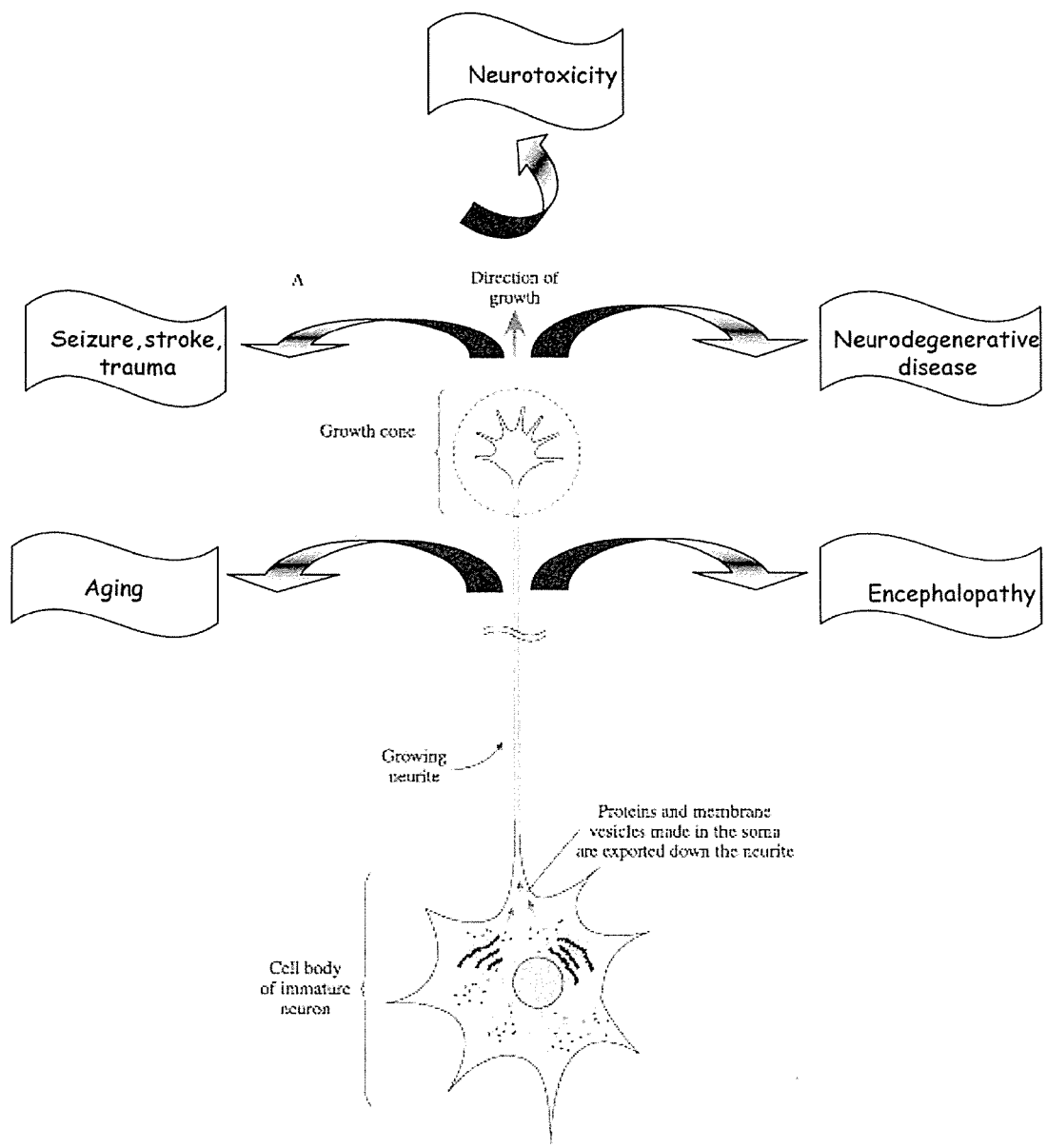
FIG. 1: neurogeneration, neuroregeneration and neuroprotection are implicated in various neuronal disorders, conditions and diseases, including neurotoxicity, seizure, stroke, trauma, aging, neurodegenerative disease, encephalopathy.

Neuroregeneration and neuroprotection are common milestones in fields as large as neurotoxicity, neurodegenerative diseases, trauma-seizure-stroke, encephalopathy or even more aging at large (cf. FIG. 1).

Immature human neurons, such as neuroblastoma cells, are able to differentiate further if treated with the appropriate signaling molecules. This is the case for the SH-SY5Y cells when they are treated with the cell permeable db-cAMP.

The inventors have developed a functional neuroprotection test, which involves the use of a human neuroblastoma cell line, such as the human neuroblastoma cell line SH-SY5Y. In this system, cells can be further differentiated and the outgrowth of the neurites can be monitored, which allows testing for growth cone activity stimulating effectors. Moreover, the ability of elongated neurites to fight against retraction processes can be evaluated after drug treatment such as lysophosphatidic acid (LPA) or hydrogen peroxide ($H_2O_2$). Data gathered with such systems have been proved to be correlated with neurotoxicity analyses made in vivo.

The example below notably demonstrates that:
the G protein of a non-apoptotic (i.e., virulent) rabies virus strain, i.e., the CVS-NIV strain, has a neurite outgrowth promoting effect, i.e., some non-apoptotic rabies virus G proteins induce and/or stimulate neuritogenesis;

this neurite outgrowth effect is sufficiently strong to protect neurons from growth cone collapsing drug (LPA) and oxidative stress ($H_2O_2$);

it is the cytoplasmic tail of the G protein of said non-apoptotic CVS-NIV rabies virus strain, which is responsible for this neurite outgrowth effect;

apoptotic rabies virus G proteins do not show this neurite outgrowth effect; more particularly the G protein of the ERA strain, which differs from the G protein of the CVS-NIV strain by only six amino acids (and by only two amino acids in the cytoplasmic tail) does not show this neurite outgrowth effect;

this is notably due to the fact that the PDZ-BS motif that is contained in the cytoplasmic tail of said non-apoptotic rabies virus G protein shows a single-point mutation compared to the one of said apoptotic rabies virus G protein: the protein G of the non-apoptotic CVS-NIV strain has amino acid Q at position 521 (position computed with respect the full length G protein of the CVS-NIV strain, corresponding to position 41 in the cytoplasmic fragment of said G protein), whereas G-ERA has E at the same position;

the amino acid, which is at position 491 in the full length G protein of the CVS-NIV strain (position 11 in the cytoplasmic fragment of said G protein), also contributes to this neurite outgrowth effect (amino acid H).

Material and Methods

Cells, Viruses and Molecular Clones

SH-SY5Y is a neuroblastoma cell line, which is available from the American Type Culture Collection (ATCC; 10801 University Blvd.; Manassas, Va. 20110-2209; U.S.A.) under deposit number CRL-2266).

The original ERA and CVS strains of rabies virus (RABV) are available from the ATCC under deposit number vr332 and vr959, respectively. The ERA and CVS strains, which have been used in this study, have been passaged in the inventors' laboratory for the last twenty years on BSR cells (a clone of Baby Hamster Kidney cells-clone 21, ATCC deposit number BHK-21). These passages strains are the ERA-NIV strain and the CVS-NIV strain, respectively.

Throughout the examples and the figures of the application, CVS means CVS-NIV and ERA means ERA-NIV (G protein CNCM I-2760; SEQ ID NO: 4), unless otherwise specified.

The CVS-NIV strain (rRABV CVS HQ) has been deposited at the Collection Nationale de Cultures de Microorganismes (CNCM) on the 1$^{st}$ of Apr., 2009 under the terms of the Budapest Treaty (CNCM; Institut Pasteur; 25, rue du Docteur Roux; F-75724 PARIS CEDEX 15; FRANCE). The CNCM deposit number is I-4140.

The obtention and characterization of the molecular clones representative of the G protein of the ERA-NIV strain, i.e., of G-ERA-NIV, and of the G protein of the CVS-NIV strain, i.e., of G-CVS-NIV, have been described in Préhaud et al. 2003.

The sequences of these G proteins are also available under accession number AF 406693 (for G-ERA-NIV) and AF 406694 (for G-CVS-NIV); cf. also FIGS. 13A and 13B.

The G protein of the CVS-NIV strain is also available from the recombinant *E. coli* strain deposited on the 30$^{th}$ of Nov., 2001 at the CNCM under the terms of the Budapest Treaty. The CNCM deposit number is I-2758. This recombinant *E. coli* comprises a plasmid (plasmid pRev-TRE-G-CVS; cf. WO 03/048198), which inducibly expresses the G protein of the CVS-NIV strain.

The G protein of the ERA strain is also available from the recombinant *E. coli* strain deposited on the 30$^{th}$ of Nov., 2001 at the CNCM under the terms of the Budapest Treaty. The CNCM deposit number is I-2760. This recombinant *E. coli* comprises a plasmid (plasmid pRev-TRE-G-ERA; cf. WO 03/048198), which inducibly expresses the G protein of the ERA strain.

Appropriate conditions for the cultivation of the recombinant *E. coli* strain containing the plasmid CNCM I-2758 coding for the G protein of the rabies virus CVS-NIV strain and for the cultivation of the recombinant *E. coli* strain containing the plasmid CNCM I-2760 coding for the G protein of the rabies virus ERA strain comprise the incubation of said recombinant *E. coli* strain at 37° C. on a standard LB-TYM growth medium (in the presence of ampicillin).

The recombinant rabies viruses (rRABV) were produced and isolated following the procedures described by Faul et al. 2008. rRABVs were constructed to harbor either the wild type "G survival" or "G death" sequences (G sequence of the CVS-NIV strain and of the ERA strain, respectively), or the cytoplasmic tail of G survival in an ERA genetic G gene background, or the cytoplasmic tail of G death in a CVS-NIV genetic G gene background (cf. FIG. 2).

Recombinant rabies viruses were also produced, which derive from the CVS-NIV strain by mutations in the G coding sequence. These recombinant rabies viruses have a G protein, which differs from the G protein of the CVS-NIV strain by one or two amino acids, namely:

by the amino acid, which in the full length G protein sequence of the CVS-NIV strain is at position 491 (position 11 in the cytoplasmic fragment thereof); and/or by the amino acid, which in the full length G protein sequence of the CVS-NIV strain is at position 521 (position 41 in the cytoplasmic fragment thereof).

More particularly, the following recombinant rabies virus strains were produced:

TABLE 2

|  | Position 491 in the full length G protein of the virus (amino acid H in the G protein of the CVS-NIV strain) | Position 521 in the full length G protein of the virus (amino acid Q in the G protein of the CVS-NIV strain) |
|---|---|---|
| rRABV CVS LE | L | E |
| rRABV CVS LQ | L | Q |
| rRABV CVS HE | H | E | rRABV CVS LE, rRABV CVS LQ and rRABV CVS HE have been deposited at the CNCM under the terms of the Budapest Treaty on the 1 Apr. 2009. The CNCM deposit numbers are I-4141, I-4142 and I-4143, respectively.

Appropriate conditions for the propagation of the virus I-4141 or I-4142 or I-4143 (recombinant rabies viruses) comprise the incubation of said virus at 37° C. under 5% $CO_2$ with BHK-21 cells (sub-clone BSR) on a DMEM growth medium containing glucose (e.g., 4.5 g/L), sodium pyruvate and glutamax (Invitrogen 31966047) and 5% FBS.

High-Throughput Neurite Outgrowth and Retraction Assays

SH-SY5Y human neuroblastoma cells are seeded on 24-well plates (Cell Bind plastic ware, Corning, USA) at a density of 40,000 cells per well in non differentiating medium [DMEMF12 (Invitrogen, U.K.) with 20% Fetal Bovine Serum plus 1% Pen:Strep and 1% Glutamine], and cultured overnight at 37° C. 24 h post seeding non differentiation medium is replaced with differentiating medium [Neurobasal medium (Invitrogen, U.K.) supplemented with B27 supplement (Invitrogen, U.K.), 1% P/S, 1% Glutamine and 1 mM db-cAMP (dibutyril c-AMP is membrane permeable, Sigma)], and the cells are incubated for 6 h. Then, cells are mock infected, infected with rRABV at a MOI 3 in differentiating medium. After 1 h of incubation, cells are washed once with differentiating medium, and after adding differentiating medium they are incubated for 24 h at 37° C.

For natural differentiation, the same procedure is used but db-cAMP is omitted.

30 h post differentiation, the cells are fixed with 3% paraformaldehyde in phosphate buffered saline (PBS) for 20 min at room temperature (RT) followed by treatment for 5 mn with 0.1% Triton-X-100 and 50% normal goat serum (NGS) in PBS for 1 h at RT. Neuronal specific anti βIII tubulin Ab (Promega, France) and anti-RABV nucleocapsid Ab are used to stain the neurite processes and to reveal RABV infection respectively. Alternatively, cells are also stained with crystal violet which preserves the neurites processes.

Retraction assay is identical to the outgrowth assay as mentioned above, except for the addition of either 10 µM-30 µM or 50 µM LPA (Sigma, USA) in differentiating medium or 75 µM $H_2O_2$ (Sigma, USA), in B27 minus anti oxidant containing differentiating medium.

Cells are imaged using a Leica DM 5000B UV microscope equipped with a DC 300FX camera (×40 or ×20 objectives) and analyzed using ImageJ 1.38X Software (Wayne Rasband, NIH, USA) and its plug-in NeuronJ (Meijering et al. 2004). The average neurite length per neuron is determined from triplicate experiments.

Detection of RABV Antigens by Flow Cytometry

SH-SY5Y cells were differentiated by treatment with db c-AMP and infected with rRABVs 6 hours post differentiation. 24 hours post infection, cells were harvested and treated for the detection by flow cytometry of either the RABV glycoprotein which reached the cytoplasmic membrane or the total amount of G protein expressed in the infected cells. The procedures followed have been described in Préhaud et al. 2003.

Results and Discussion

G-CVS-NIV Cytoplasmic Tail (i.e., the Cytoplasmic Tail of the G Protein of the CVS-NIV Strain) Contains a Molecular Signature Promoting Neurite Outgrowth In absence of infection, treatment with db-cAMP triggers elongation of neurites (FIG. 3A, the two left panels). When cells are treated with db-cAMP and infected with rRABV G-CVS-NIV, they exhibit longer neurites (191%, FIG. 3A, middle right panel). This result establishes that rRABV G-CVS-NIV promotes neurite outgrowth when the growth cone activity is stimulated by cAMP signaling.

In contrast, the length of the neurites is similar in between non infected cells and rRABV G-ERA infected cells both treated with db-cAMP (FIG. 3B), which shows that G death expressing rRABV ERA has a silent phenotype for the neurite outgrowth assay. It is worth noting that the time course of the experiment (i.e., 30 h post differentiation and 24 hours post infection) is a time point earlier than the time point where the maximum level of apoptosis is detected in rRABV ERA infected neuroblastoma cells (i.e., 48 h post infection).

By using rRABVs carrying the end swap of the G protein (cf. FIG. 2) as described on FIG. 3C, the inventors show that this phenotype is totally transferred by the cytoplasmic tail only. This result firmly establishes that G-CVS-NIV cytoplasmic tail contains a molecular signature promoting neurite outgrowth when the elongation processes are initiated by the cAMP signaling pathway.

Furthermore, neurite outgrowth assays were performed with recombinant rabies virus, which differ from the CVS-NIV strain (rRABV G-CVS-NIV) by one or two amino acids in their respective G proteins.

More particularly, assays were performed with rRABV CVS LE, rRABV CVS LQ and rRABV CVS HE, which express a G protein that differs from G-CVS-NIV by amino acid 491 and/or amino acid 521 (cf. table 2 above). The results of these assays are illustrated by FIG. 3D. In FIG. 3D, all the differences with respect to the control are statistically significant ($p<0.005$ Student's t test):

rRABV G-CVS HQ versus N.I.: $p<0.0001$;
rRABV G-CVS LQ versus N.I.: $p=0.0002$;
rRABV G-CVS HE versus N.I.: $p=0.0111$.

rRABV G-CVS-NIV has H and Q at positions 491 and 521 of its G protein, respectively (positions computed with respect to the full length G protein of CVS-NIV, these positions corresponding to positions 11 and 41 in the cytoplasmic fragment of this G protein, respectively).

rRABV CVS LQ has L and Q at these positions.
rRABV CVS HE has H and E at these positions.
rRABV CVS LE has L and E at these positions.

As illustrated by FIG. 3D, rRABV CVS LQ and rRABV CVS HE still show a positive neurite outgrowth effect, although at a significantly lower extent that CVS-NIV (rRABV G-CVS-NIV) [Student's t test analysis: rRABV CVS HQ versus rRABV CVS LQ: $p=0.0156$; rRABV CVS HQ versus rRABV CVS HE: $p=0.0009$].

Therefore, position 491 and position 521 of the G protein of the CVS strain (positions 11 and 41 in the cytoplasmic fragment) are both tightly involved in the neurite outgrowth effect and position 521 has a predominant contribution thereto.

rRABV CVS LE did not induce any significantly positive neurite outgrowth effect compared to the control (cf. FIG. 3C, where rRABV G-CVS Cyto Death=rRABV CVS LE).

G-CVS-NIV Cytoplasmic Tail is an Intrinsic Effector Promoting Neuritogenesis, which Works Synergistically with cAMP The inventors investigated whether the expression of G-CVS-NIV cytoplasmic tail could on and of its own stimulate neuritogenesis. SH-SY5Y cells were infected with the different rRABV (cf. FIG. 2) and the elongation of the neurites was monitored.

As observed in FIG. 4A, the expression of G-CVS-NIV or G-ERA-cyto survival is sufficient to promote neurites outgrowth. These data establish that the cytoplasmic domain of G-CVS-NIV contains an intrinsic molecular signature which signalized by an unknown mechanism the neurite elongation processes. When the same experiment was undertaken with or without db-cAMP, it was observed that both G-CVS-NIV and cAMP mediated neurites outgrowth work synergistically (cf. FIG. 4B).

Neuritogenesis Based Cytoplasmic Domain of G-CVS-NIV is Dependant of the Molecular Signature and not of the Amount of Expressed G Protein The amount of rabies virus glycoprotein produced was analyzed very carefully either by monitoring the total quantity of RABV antigen produced in the infected db-cAMP treated SH-SY5Y cells, or the quantity of G-protein fully processed to the cytoplasmic membrane. The two rRABVs expressing G-CVS-NIV or G-ERA have a similar amount of G-protein expressed in toto and at the cytoplasmic membrane (cf. FIG. 5). Thus, the survival phenotype, i.e., neurite outgrowth, is not linked to a phenomenon of quantity of available protein, but rather to specific determinant(s) present on the sequence of the cytoplasmic survival peptide.

Moreover, it is interesting to note that rRABV G-ERA cyto survival express slightly less glycoprotein, but this virus still exhibits a strong survival phenotype (cf. FIGS. 3C, 4A). It means that as long as the survival determinant(s) are present inside the infected cells, the amount of the peptide is not the major caveat and the neurites outgrowth is stimulated.

G-CVS-NIV Cytoplasmic Tail Confers Neuroprotection Against Growth Cone Collapsing Drug LPA is a bioactive lipid acting as growth factor-like phospholipids which has been shown to exert diverse cellular functions that influence cell growth, motility, morphology and fate. On neuronal cells, LPA mediates growth cone collapsing and neurite retraction involving Rho and Rho-kinase activation which drives the re-organization of the actomyosin cytoskeleton.

The ability of the G protein cytoplasmic tail to protect against 10 µM LPA induced neurites retraction was investigated. When db-cAMP differentiated SH-SY5Y cells are treated with LPA, retraction of the neurites is observed (cf. FIG. 6A, left). The same effect is also observed when cells are infected with rRABV G-ERA (cf. FIG. 6A, right). On the contrary, the long neurites detected on db-cAMP treated and rRABV G-CVS-NIV infected cells are totally preserved against treatment with a growth cone collapsing agent (cf. FIG. 6A, middle). This result establishes that G-CVS-NIV possess some intrinsic neuroprotective properties.

This protection is also noticed following infection with rRABV G-ERA-Cyto survival but not with rRABV G-CVS-Cyto death: cf. FIG. 6B. Therefore, the use of the end-swap mutants firmly establishes that the neuroprotection phenotype is linked to the expression of G-CVS cytoplasmic domain.

G-CVS-NIV Cytoplasmic Tail Neuroprotection to LPA is Robust

LPA physiological range is usually around 1 µM. The inventors used a high dose of LPA, i.e., 10 µM, to validate the robustness of the G-CVS-NIV cytoplasmic tail conferred neuroprotection.

Sub-lethal doses of LPA up to 50 µM were tested in order to monitor the efficiency of this neuroprotection. SH-SY5Y cells were either non infected or infected with rRABV G-CVS-NIV or rRABV G-ERA-Cyto survival. 30 hours post differentiation, cells were treated with different doses of LPA (cf. FIG. 7). Treatments of non infected cells with increasing amount of LPA drive a linear retraction of the length of the neurites (cf. FIG. 7, left). On the contrary, cells which have been infected with rRABV G-CVS-NIV do not exhibit any obvious collapsing of their neurites whatever is the dose of the LPA (cf. FIG. 7, middle). The same data are observed for the cells infected with rRABV G-ERA-Cyto survival for a dose of LPA up to 30 µM (cf. FIG. 7, right). The slight decrease observed for the highest dose of LPA (50 µM) might be relative to the lowest amount of G protein expressed by this rRABV. In this case, and for a very high concentration of growth cone collapsing drug, the relative amount of G protein might become a limiting factor. In any case, these data proved the very high efficiency of the G-CVS-NIV cytoplasmic tail conferred neuroprotection.

G-CVS-NIV Cytoplasmic Tail Confers Neuroprotection Against Oxidative Stress

Based on the observations made above on the neuroprotection conferred by G-CVS-NIV cytoplasmic domain on LPA driven neurites retraction, the inventors asked the question whether this phenotype could be generalized to other more ubiquitous agents.

Oxidative stress represents an important pathway leading to neuronal degeneration. Oxidative stress has been implicated in many neurodegenerative diseased but also in case of acute damage to the brain such as trauma, stroke and epilepsy. Therefore, the inventors undertook a study on the neurite retraction phenotypes after hydrogen peroxide treatment. When differentiated cells are subjected to 75 µM $H_2O_2$, their neurites shorten (cf. FIG. 8, first pair of bars at the left). The same observation is made when the cells have been previously infected with rRABV G-ERA (cf. FIG. 8, third pair of bars). To the contrary, no retraction of the neurites is observed when cells are infected with rRABV G-CVS-NIV (cf. FIG. 8, second pair of bars). Thus G-CVS-NIV expression confers neuroprotection against an oxidative stress.

By using end swap mutants, we also showed that this neuroprotective property is linked to the expression of G-CVS-NIV cytoplasmic tail as described on FIG. 8 (cf. fourth and fifth pairs of bars, relating to rRABV G-CVS-Cyto death and rRABV G-ERA-Cyto survival, respectively; cf. FIG. 2 for the structure of these end-swap mutants).

The COOH Terminal PDZ-BS of the Cytoplasmic Domain of the Rabies Virus G Protein is Critically Involved in the Survival Phenotype Fate of the Infected Neuronal Cells Deletion of the last 4aa residues of the G-Cyto survival (survival G-protein-delta) was sufficient to significantly reduce the survival phenotype of the rRABV, as measured by its effect on the neurite outgrowth.

See for example FIG. 20, which shows the neurite outgrowth measured at 8 hours post-infection, in the presence of db-cAMP, as induced by rRABV CVS-NIV Delta-PDZ-BS (CVS-NIV having amino acid H at position 491 and from which PDZ-BS has been deleted), compared to control (N.I.) and to G-CVS-NIV (CVS-NIV having amino acid H at position 491 and having its PDZ-BS, i.e., QTRL in positions 521-524): the neurite outgrowth effect induced by rRABV CVS-NIV Delta-PDZ-BS is significantly different from the one induced by the control (p=0.0002 Student's t test) and is significantly different from the one induced by rRABV CVS-NIV (p=0.0003 Student's t test).

The inventors notably demonstrate that:
protein G of CVS-NIV (G-CVS-NIV) is able to promote neurite outgrowth (neuritogenesis) in a system where the growth cone activity is stimulated by the c-AMP signaling pathway (delivered as an external effector);
The cytoplasmic domain of G-CVS-NIV is responsible of this phenotype;
The expression of the cytoplasmic tail of G-CVS-NIV is also responsible for the stimulation of the neurite outgrowth in the absence of c-AMP;
Both G-CVS-NIV and c-AMP work as synergistic effectors;
The phenotypes are linked to the molecular signature delivered by the cytoplasmic tail of G-CVS-NIV, more particularly by those amino acids which are at positions 491 and 521 in the full length G-CVS-NIV protein (positions 11 and 41 in the cytoplasmic fragment thereof), still more particularly by the amino acid, which is at position 521 in the full length G-CVS-NIV protein (position 41 in the cytoplasmic fragment thereof), and which is part of the PDZ-BS;
The survival phenotype conferred by the G-CVS-NIV cytoplasmic tail is highly resistant to treatments by growth cone collapsing agent (i.e., LPA);
The survival phenotype conferred by the G-CVS-NIV cytoplasmic tail is also resistant to oxidative stress ($H_2O_2$).

Example 2

The Cytoplasmic Domain of G-CVS-NIV Confers Neuroprotection Against HSV-1 Cytophatic Effect Herpes simplex virus type I encephalitis (HSVE) is the most common sporadic fatal central nervous system infection in western countries and manifest throughout the year in patients of all ages. HSVE develops when herpes simplex virus type 1 infects brain tissues in a lytic:necrotic manner.

The ability of the G protein cytoplasmic tail to protect against the cytopathic effect of HSV-1 in cellulo was investigated.

Material and Methods
Neurite Outgrowth
As described in example 1 above.
HSV-1 Cytopathic Effect Determination
rRABV were produced as described in example 1 above.
rRABV was propagated in BSR cells (cf. Faul et al. 2008)
HSV-1 strain KOS (cf. Skare et al. 1975) was propagated in U373MG cells (ATCC HTB 17).

SH-SY5Y cells were mock infected or infected with rRABV in differentiating medium minus db-c-AMP for 6 hours. Then, HSV-1 was added at a multiplicity of infection of 3 (MOI 3) and the neurites outgrowth phenotypes were determined 24 hours later. In order to establish the effect on neurite outgrowth of the sole HSV-1 infection, SH-SY5Y cells were differentiated by db-c-AMP in differentiating medium for 6 hours and the HSV-1 infection (MOI 3) was then realized.

Neurite outgrowth phenotype was determined as well 24 hours later.

Results and Discussion

SH-SY5Y neuroblastoma cells, which have been differentiated by treatment with db c-AMP, show a drastic retraction of their neurites (up to 79%, cf. FIG. 9A) after HSV-1 infection, which can eventually lead to the death of the cells.

To the contrary, when cells have been previously infected with rRABV G-CVS-NIV or rRABV G-ERA-Cyto Survival (cf. example 1 above), they exhibit neurite outgrowth (cf. FIG. 9B) and are protected against extensive neurite retraction (cf. FIG. 9C).

Example 3

The Cytoplasmic Domain of G-CVS-NIV Exhibits Anti-Proliferative Properties for Neuroblastoma Cells Neuroblastoma is the second most common solid tumor of childhood accounting for more than 13% of cancer death in children for the United States. Prognosis depends on the clinical stage of the disorder and the age of the child. Generally, most patients with neuroblastoma are treated with therapeutic approaches that include surgery, radiation and cytotoxic chemotherapy.

Since human malignant neuroblastoma is characterized by poor differentiation and uncontrolled proliferation of immature neuroblasts, pro-differentiative drugs such as all-trans-retinoic acid (ATRA) at high doses have been used. The inventors have demonstrated that RABV G-CVS-NIV cytoplasmic tail is able to promote neurite outgrowth on SH-SY5Y human neuroblastoma cells (cf. the examples above), i.e., to induce the differentiation of these cells. Therefore, the inventors wanted to answer the question of whether this differentiation property was efficient enough to control the proliferation of such cells in culture.

Material and Methods
MTT Assay

The assay is described by Sargent 2003. Briefly, cells, which have been mock infected or infected with rRABV for 48 h in differentiating medium without db c-AMP, are stained with the MTT solution for 3.5 hours at 37° C. with 5% $CO_2$. The mixture of medium and staining solution is then removed, the MTT crystals are dissolved with the dissolvent for one hour at room temperature under constant agitation. The assay is read at an OD of 550 nm. Each condition represents a n of 8. Statistical analysis was done with ANOVA tests.

Flow Cytometry

Cell counting and morphological changes were assessed by side and forward light scattering (SSC and FSC, respectively) as described in Préhaud et al. 2003. Each point represents the cells gathered during 1 minute at low speed. Flow cytometry analyses were gated on a viable population in order to exclude dead or necrotic cells which represent less than 1% of the cell population at the 48 h time point.

Neurite Outgrowth
As described in example 1 above.
ATRA Treatment

All trans retinoic acid (ATRA) treatment of the neuroblastoma cells was undertaken as already described by Préhaud et al. 2005.

Results and Discussion

In a first instance, SH-SY5Y cells were either non-treated or treated with ATRA at 5 µM or 10 µM in the culture medium. Cell proliferation was either assayed by flow cytometry for viable cells or by cell counting via an MTT assay. The data are presented on FIGS. 10A and 10B, respectively.

In each case, ATRA treatment of the cells leads to a slower growth of the neuroblasts with a decrease in proliferation varying in between 27% up to 55% depending on the test used to monitor cell growth. Thus, SH-SY5Y cells are effectively responding to the effect of anti-proliferative drugs.

Figure 11A:
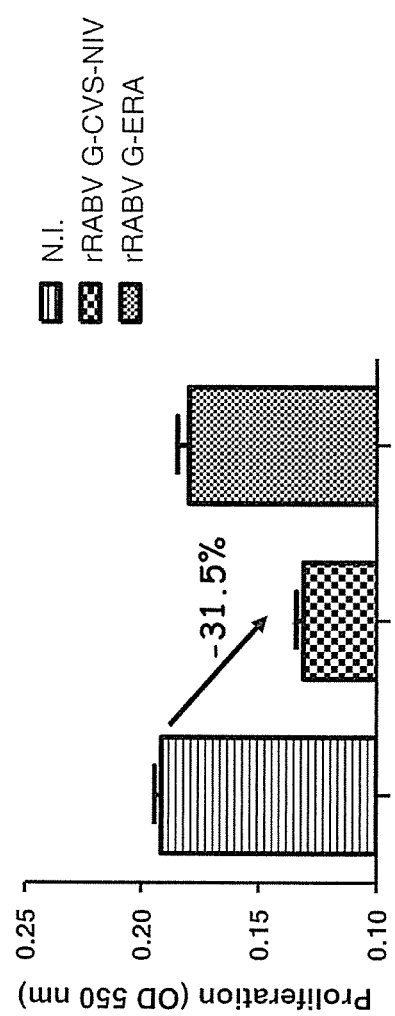
Figure 11B:
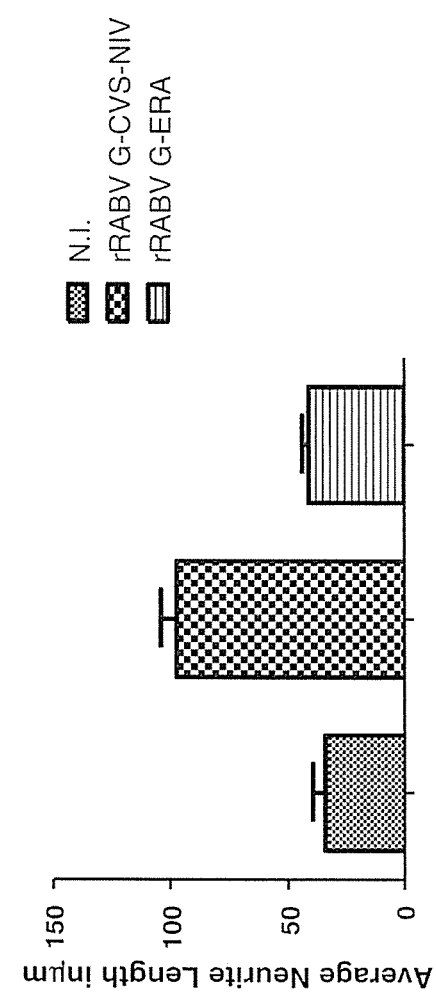

Therefore, SH-SY5Y cells were infected either with rRABV G-CVS-NIV or rRABV G-ERA and the proliferation of the cells (established by a MTT assay) as well as the outgrowth of the neurites were measured (cf. FIGS. 11A and 11B). We found that the cell growth was inversely correlated to the neurite outgrowth, establishing that the neurosurvival property of G-CVS-NIV is associated by an intrinsic anti-proliferative phenotype on neuroblasts.

Neuroblastoma cells were infected in a second series of experiments with either the parental rRABV G-CVS-NIV or rRABV G-ERA viruses as well as the end swap mutants (rRABV G-CVS-Cyto death or rRABV G-ERA-Cyto survival; cf. example 1 above and FIG. 2). Cell growth was measured by flow cytometry and MTT assay (cf. FIGS. 12A and 12B, respectively). The data showed that in each case when the cells are infected with neurites outgrowth promoting G-cyto survival tail viruses, the proliferation of the neuroblasts is affected varying from a lag in between 18.3% to 23%. Thus, G-Cyto survival possesses an intrinsic property to slow down neuroblasts cell growth.

Example 4

Experimental Demonstration that Pro-Survival Properties of Cyto-G are Conserved in the Expression Vector This example demonstrates that, when it is expressed in the cell in the absence of viral infection (polypeptides delivered at first as an expression vector), the RABV cytoplasmic domain of the G protein of a non-apoptotic rabies virus strain (Cyto-G) conserves the pro-survival properties (neuritogenesis and protection against retraction).

This example further investigates whether said survival properties depend upon the size and upon the anchorage into the cytoplasmic or endoplasmic membrane.

Mutagenesis was undertaken by using oligonucleotides-PCR based mutagenesis procedures successfully used to generate the rRABVs of example 1 (QuickChange Lightning site-directed mutagenesis kit, Agilent Technologies; Stratagene product division; Catalog number 210518-12; kit used in accordance with the manufacture's recommendations; U.S. Pat. Nos. 7,176,004; 7,132,265; 7,045,328; 6,734,293; 6,489,150; 6,444,428; 6,391,548; 6,183,997; 5,948,663; 5,932,419; 5,866,395; 5,789,166; 5,545,552, and patents pending).

The oligonucleotides were designed for introducing respectively NheI and XmaI sites at the extremities of the constructs.

The mutagenic primers were:

```
GFullATG:
                                              (SEQ ID NO: 28)
GGCCGCTAGCATGGTTCCTCAGGCTCTCCTGTTT GCytoATG:
                                              (SEQ ID NO: 29)
GGCCGCTAGCATGAGAAGAGTCAATCGATCAGAACCT GendSTOP:
                                              (SEQ ID NO: 30)
GGCCCCCGGGTCACAGTCTGGTCTGACCCCCACT mutTM.Cyto:
                                              (SEQ ID NO: 31)
CCCCTTCTGGTTTTTCCATTGTGTTTTGGGGGGAAGTATGTATTACTGA
GT
```

The mutants were screened by sequencing the inserts. By using this methodology, the following three constructs (G-Full; G-[SP-(2aa)-TM-Cyto]; G-Cyto) were notably obtained:

G-Full: Accession Number AF 406694 (G Protein of CVS-NIV)

```
                                              (SEQ ID NO: 2)
MVPQALLFVPLLVFPLCFGKFPIYTIPDKLGPWSPIDIHHLSCPNNLVV

EDEGCTNLSGFSYMELKVGYILAIKMNGFTCTGVVTEAETYTNFVGYVT

TTFKRKHFRPTPDACRAAYNWKMAGDPRYEESLHNPYPDYHWLRTVKTT

KESLVIISPSVADLDPYDRSLHSRVFPSGKCPGVAVSSTYCSTNHDYTI

WMPENPRLGMSCDIFTNSRGKRASKGSETCGFVDERGLYKSLKGACKLK

LCGVLGLRLMDGTWVAMQTSNETKWCPPDQLVNLHDFRSDEIEHLVVEE

LVRKREECLDALESIMTTKSVSFRRLSHLRKLVPGFGKAYTIFNKTLME

ADAHYKSVRTWNEILPSKGCLRVGGRCHPHVNGVFFNGIILGPDGNVLI

PEMQSSLLQQHMELLESSVIPLVHPLADPSTVFKDGDEAEDFVEVHLPD

VHNQVSGVDLGLPNWGKYVLLSAGALTALMLIIFLMTCCRRVNRSEPTQ

HNLRGTGREVSVTPQSGKIISSWESHKSGGQTRL
```

G-[SP-(2aa)-TM-Cyto]:

G-[SP-(2aa)-TM-Cyto] is a construct comprising (from N- to C-term):
- the signal peptide of a G protein (e.g., the signal peptide of CVS-NIV; SEQ ID NO: 21);
- 2 amino acids (e.g., from the ectodomain of a G protein, such as from G-CVS-NIV);
- the transmembrane domain of the G protein of a non-apoptotic rabies virus strain (e.g., the transmembrane domain of G-CVS-NIV; SEQ ID NO: 23);
- the cytoplasmic domain of the G protein of a non-apoptotic rabies virus strain (e.g., the cytoplasmic domain of G-CVS-NIV; SEQ ID NO: 6).

The sequence of G-[SP-(2aa)-TM-Cyto] that was used in the present example is:

```
                                              (SEQ ID NO: 27)
MVPQALLFVPLLVFPLCFGGKYVLLSAGALTALMLIIFLMTCCRRVNRS

EPTQHNLRGTGREVSVTPQSGKIISSWESHKSGGQTRL
```

G-Cyto:

G-Cyto is a construct comprising (from N- to C-term): an amino acid (e.g., M) and the cytoplasmic domain of the G protein of a non-apoptotic rabies virus strain (e.g., the cytoplasmic domain of G-CVS-NIV; SEQ ID NO: 6).

The sequence of the G-Cyto that was used in the present example is:

```
                                              (SEQ ID NO: 24)
    MRRVNRSEPTQHNLRGTGREVSVTPQSGKIISSWESHKSGGQTRL.
```

The sequences are shown on FIG. 22.

The sequence alignment is shown on FIG. 23.

A schematic representation of the three constructs is shown in FIG. 24.

Inserts were removed by NheI and XmaI digestion and were cloned in SAP dephosphorylated pCI-Neo derivative (Promega, France) by standard cloning procedures. *E. coli* XL1-blue cells (Stratagene, USA) were transformed with the plasmid constructs. Plasmid DNA was extensively purified on Purelink columns (Invitrogen, U.K.) and the inserts were sequenced in order to verify the integrity of the sequence inserted in the plasmid. Plasmid clones were used to nucleofect human neuroblastoma cells [SH-SY5Y cells (ATCC CRL-2266), or Ntera cl2D1 cells (ATCC CRL-1973)] using the Amaxa GmbH electroporation technology (Amaxa® nucleofector® kit V Catalog #VCA 1003 Lonza Germany following the manufacturer's recommendations). The expression of the G proteins was assayed by flow cytometry as described in example 1.

For transient expression, the biological assays were undertaken 24 h post nucleofection.

For stable expression, both nucleofected cell lines [SH-SY5Y or Ntera cl2D1] were treated with G418 at 800 µg/ml over three weeks. Cell clones resistant to G418 were isolated and frozen. The control cell line consists of cells, which have been nucleofected with pCI-Neo alone without any insert.

The neurite outgrowth assays and retraction assays were performed as described in example 1.

Illustrative results are shown in FIGS. 25-28.

FIG. 25 illustrates the expression of a polypeptide comprising the cytoplasmic domain of a non-apoptotic rabies virus strain, more particularly the expression:
- of the full length G protein of said rabies virus strain,
- of a polypeptide, which comprises the transmembrane and cytoplasmic domains of said G protein, but which does not comprise the ectodomain of said G protein, and
- of a polypeptide, which comprises the cytoplasmic domain of said G protein, but which does not comprise the ectodomain and the transmembrane domain of said G protein, compared to the expression measured with the control plasmid.

As already illustrated, the G level expression is different and the biological phenotypes are not correlated directly with the level of expression (see below and FIG. 5).

The transient expression of the cytoplasmic domain of the G protein of a non-apoptotic rabies virus strain—in the absence of viral infection—induces and/or stimulates neurite outgrowth from human neuroblastoma cells (FIG. 26). A transiently-expressed polypeptide comprising the transmembrane domain in addition to the cytoplasmic domain (but which does not comprise the ectodomain) of said G protein is more efficient in inducing and/or stimulating neurite outgrowth than the transiently-expressed full length G protein or than the transiently-expressed cytoplasmic domain of said G protein (cytoplasmic domain without the ectodomain and without the transmembrane domain) (FIG. 26).

The stable expression of the cytoplasmic domain of the G protein of a non-apoptotic rabies virus strain, or of polypeptides or proteins comprising said domain—in the absence of viral infection—is feasible in human neuroblastoma cells (FIG. 27). A stably-expressed polypeptide comprising the transmembrane domain in addition to the cytoplasmic domain (but which does not comprise the ectodomain) of said G protein is more efficient in inducing and/or stimulating neurite outgrowth than the stably-expressed full length G protein or than the stably-expressed cytoplasmic domain of said G protein (cytoplasmic domain without the ectodomain and without the transmembrane domain) (FIG. 27). The stably-expressed cytoplasmic domain of said G protein (cytoplasmic domain without the ectodomain and without the transmembrane domain) is as efficient in inducing and/or stimulating neurite outgrowth as the stably-expressed full length G protein (FIG. 27).

The expression of a polypeptide comprising the cytoplasmic domain of a non-apoptotic rabies virus strain—in the absence of viral infection—confers resistance to a neurotoxic agent (e.g., the growth cone collapsing drug LPA; cf. FIG. 28, showing results obtained with the G-(SP-[2a]-TM-Cyto) construct).

In the same experimental conditions, this batch of LPA is inducing growth cone collapsing as illustrated in FIGS. 6A, 6B, 7.

The transmembrane domain of G-(SP-[2a]-TM-Cyto) notably allows the polypeptide expressed by this construct to be anchored in the Golgi membrane and/or the endoreticulum membrane of the cells, thereby increasing the efficiency of the expressed polypeptide in inducing and/or stimulation neurogeneration, neuroregeneration and neuroprotection.

Hence, coupling the cytoplasmic domain of the G protein of a non-apoptotic rabies virus strain to such a membrane-anchoring sequence increases the neurogeneration, neuroregeneration and neuroprotection effects induced and/or stimulated by said cytoplasmic domain.

Example 5

Experimental Demonstration that the Cytoplasmic Domain of a Non-Apoptotic Rabies Virus Strain Possess Intrinsic Properties to Drive Neuronal Precursor (EC Cells) to Differentiation to Mature Neurons (Commitment)

The cytoplasmic domain of a non-apoptotic rabies virus strain, such as Cyto-G (cf. example 4 above; e.g., SEQ ID NO: 6 or 24), promotes the outgrowth of the neurites by such promoting the differentiation of the neuroblastoma cell line SH-SY5Y (cf. example 4 above).

Example 5 brings the experimental demonstration that this property reveals a wider ability of said cytoplasmic domain to promote and to orientate the commitment of the cell line toward the neuronal differentiation.

Production of pure post-mitotic human neurons from the embryonic carcinoma cell line NTera 2cl.-D1 (ATCC CRL-1973) has been described in the art, e.g., in Préhaud et al. 2005.

Constructs expressing the cytoplasmic domain of the G protein of a non-apoptotic rabies virus strain, as described in example 4 above, were used, e.g.:
- the G-Full construct containing the G protein of a non-apoptotic rabies virus strain (G protein of SEQ ID NO: 2) as an insert,
- the G-Cyto construct containing the cytoplasmic domain of a non-apoptotic rabies virus strain (cytoplasmic domain of SEQ ID NO: 6) as an insert, and
- the G-(SP)-[2aa]-TM-Cyto construct, containing the signal peptide of a non-apoptotic rabies virus strain (signal peptide of SEQ ID NO: 21), two amino acids (from the C-terminal end of the ectodomain of the G protein of a non-apoptotic rabies virus strain, e.g., GK), the transmembrane domain of the G protein of a non-apoptotic virus strain (transmembrane domain of SEQ ID NO: 23) and the cytoplasmic domain of a non-apoptotic rabies virus strain (cytoplasmic domain of SEQ ID NO: 6).

The ability of the G-expressing constructs to induce the differentiation of NTera 2-D1 cells into neurons was investigated.

Stable G-expressing NTera 2-D1 cells were processed by following the ATRA-neurosphere like protocol as described Préhaud et al. 2005.

After the last antimitotic treatment and the two replicates, cells were seeded either for accounting neurite tips (5 days post last replicate) or neuronal network architecture (50 days post last replicate).

Illustrative results are shown in FIGS. 29-31.

The expression of a polypeptide comprising the cytoplasmic domain of the G protein of a non-apoptotic rabies virus strain—in the absence of viral infection—induces and/or stimulates the production of mature post-mitotic human neurons by differentiation from neuroblastoma cells: cf. FIG. 29, illustrating the results obtained with the expression:
- of the full length G protein of a non-apoptotic rabies virus strain,
- of a polypeptide comprising the transmembrane domain and the cytoplasmic domain (but which does not comprise the ectodomain) of said G protein,
- of the cytoplasmic domain of said G protein (cytoplasmic domain without the ectodomain and without the transmembrane domain), compared to the control plasmid.

The polypeptide, which comprised the transmembrane domain in addition to the cytoplasmic domain of the G protein of a non-apoptotic rabies virus strain (but which does not comprise the ectodomain of said G protein) is more efficient in inducing and/or stimulating said differentiation of post-mitotic human neurons than the full length G protein or than the cytoplasmic domain of said G protein (cytoplasmic domain without the ectodomain and without the transmembrane domain); cf. FIG. 30.

Further to inducing and/or stimulating the production of mature post-mitotic human neurons by differentiation from neuroblastoma cells, the expression of a polypeptide comprising the cytoplasmic domain of the G protein of a non-apoptotic rabies virus strain—in the absence of viral infection—induces and/or stimulates the organisation of a network of mature post-mitotic human neurons with long axons (cf. FIG. 31).

Example 6

Experimental Demonstration that the Cytoplasmic Domain of a Non-Apoptotic Rabies Virus Strain is able to Promote Regeneration of Injured Neurons Injured neurons may have the possibility to regenerate depending on their origins and on the local environment. For example, neurons from the mammalian central nervous system have very limited regenerative capacity, even though lesion to a peripheral process results in increased regeneration of dorsal root ganglion neurons. It is clearly established that intrinsic regeneration signals influence the success of proper regeneration, some of them involving specific kinase pathway (Hammarlund et al. 2009).

The cytoplasmic domain of a non-apoptotic rabies virus strain, such as the cytoplasmic domain of SEQ ID NO: 6 contained in the Cyto-G construct (cf. example 4 above), exhibits at least two interesting properties as far as regenerative medicine is concerned.

First, it promotes neurite outgrowth, which means that said cytoplasmic domain can stimulate the neuronal growth cone.

Secondly, it preserves neurites from retraction after treatment with LPA or $H_2O_2$, which means that said cytoplasmic domain can stimulate or reinforce molecular locks avoiding the collapsing of the growth cone.

In order to bring the experimental demonstration that these properties drive the regeneration of an injured neuron, the phenomenon was investigated in a cellular model. The NT2-N cell line (human neuronal cells), stably expressing the G-[SP-(2aa)-TM-Cyto] construct of example 4 (construct containing SEQ ID NO: 27 as an insert), was chosen. The pCI-Neo-NT2-N was used as control.

The NT2-N cell line was derived from differentiated Ntera-2cl.D1 (NT2/D1; ATCC CRL-1973) cells as described in Préhaud et al. 2005, Cheung et al. 1999 and Paquet-Durand et al. 2003.

For scratch-induced assays, cells were seeded on poly-D-Lysin-laminin coated cell +(Sarstedt, Germany) 12 wells plastic ware, and were grown for two days in order to recover completely after trypsinisation. The medium was changed 10 h before scratching. Individual wounds were made with an injection needle (26GX½", 12-4.5). At least 10 scratching were made on each individual well. Cells were fixed with PFA (4%) 3 days post wounding and stained with crystal violet solution. Cells are imaged using a Leica DM 5000B microscope equipped with a DC 300FX camera (×20 objective) and analysed using ImageJ 1.38X Software (Wayne Rasband, NIH, USA) and its plug-in NeuronJ. The average percentage of neuron in regeneration is determined from 8 experiments.

Illustrative results are shown in FIGS. 32-33.

The expression of a polypeptide, which comprises the cytoplasmic domain of the G protein of a non-apoptotic rabies virus strain, induces and/or stimulates the regeneration of wounded mature post-mitotic human neurons (cf. FIG. 32, illustrating the results obtained with the expression of a polypeptide comprising the transmembrane and cytoplasmic domains of the G protein of a non-apoptotic rabies virus strain).

The neurite regeneration thus induced after wounding is drastic, more particularly when the polypeptide comprise the transmembrane and the cytoplasmic domains of said G protein, but does not comprise the ectodomain of said G protein (cf. FIG. 33, illustrating the results obtained with the expression of a polypeptide comprising the transmembrane and cytoplasmic domains of the G protein of a non-apoptotic rabies virus strain).

Example 7

An infectious rRABV cDNA was generated from the CVS-N2c rabies virus strain (Morimoto et al. 1999), a fixed pathogenic and non-apoptotic RABV.

The infectious rRABV cDNA thus generated (cN2C) is described in Schnell et al. 2010.

The gene coding for G-vir (the G protein of a non-apoptotic rabies virus strain, such as the G protein of SEQ ID NO: 2) has been integrated in this RABV cDNA. The infectious virus has been recovered as described in example 1.

The recombinant virus has been injected to groups of 8 six-week-old female C57Bl6 mice by intramuscular route with the number of virus particles of rRABV G-vir to trigger fatal encephalitis in 80% of mice. Number of mice and experiments have been carefully evaluated to minimize the animal contribution.

Disease progression has been monitored by scoring clinical signs and mortality (as described in Camelo et al. 2001). In the course of infection, groups of two or three mice have been perfused, and brains have been removed, snap frozen and stored at −80° C. before being processed for RNA extraction (half brain) and immunohistochemistry or multiplex arrays (second half brain) in order to measure the neuroinvasiveness of the virus.

This model allows to further analyze different parameters of the brain innate immune response triggered by the rRABV strain.

BIBLIOGRAPHIC REFERENCES

Blondel et al., Poliovirus, pathogenesis of poliomyelitis, and apoptosis, CTMI, 2005, 289, 25-56.

Camelo et al. 2001 "*Selective role for the p55 Kd TNF-α receptor in immune unresponsiveness induced by an acute viral encephalitis*"; J. Neuroimmunol. 113: 95-108.

Cheung et al. 1999; BioTechniques 26: 946-954.

Faul et al. 2008; Virology 382: 226-238.

Guigoni and Coulon 2002, Journal of NeuroVirology 8: 306-317.

Hammarlund et al. 2009 "*Axon regeneration requires a conserved MAP kinase pathway*" Science 323: 802-806.

Kumar et al. 2007; Nature 448: 39-43 and associated Supplementary Information ("*Methods*").

Lay et al. 2003; Ann. N. Y. Acad. Sci. 1010: 577-581.

Loh et al. 2008; Cell Death and Differentiation 15: 283-298.

Meijering et al. 2004; Cytometry Part A 58A: 167-176.

Morimoto et al. 1999, Journal of Virology 73(1): 510-518.

Paquet-Durand et al. 2003 Brain Res. Dev. Brain Res. 142: 161-167.

Préhaud et al. 1988; Journal of Virology 62(1): 1-7.

Préhaud et al. 2003; Journal of Virology 77(19): 10537-10547.

Préhaud et al. 2005; Journal of Virology 79(20): 12893-12904.

Sargent 2003; Recent Results in Cancer Research, vol. 161, Springer-Verlag Berlin Heidelberg, pages 13-25

Sarmento et al. 2005; Journal of NeuroVirology 11: 571-581.

Schnell et al. 2010; Nature Reviews Microbiology 8(1): 51-65.

Skare et al. 1975; J. Virol. 15:726-732 (Structure and function of herpesvirus genomes. I. Comparison of five HSV-1 and two HSV-2 strains by cleavage of their DNA with Eco RI restriction endonuclease).

Ugolini 1995; The Journal of Comparative Neurology 356: 457-480.

Ugolini 2008; Dodet B, Fooks A R, Müller T, Tordo N, and the Scientific & Technical Department of the OIE (eds): Towards the Elimination of Rabies in Eurasia. Dev. Biol. Basel, Karger, vol. 131, pp. 493-506.

WO 03/048198; PCT international application in the name of Institut Pasteur, Inv. Lafon et al., published on 12 Jun. 2003; as well as its national/regional counterpart applications.

Each of the relevant disclosures of all references cited herein is specifically incorporated by reference.

SEQUENCE LISTING

```
<160> NUMBER OF SEQ ID NOS: 31

<210> SEQ ID NO 1
<211> LENGTH: 1575
<212> TYPE: DNA
<213> ORGANISM: Rabies virus

<400> SEQUENCE: 1
atggttcctc aggctctcct gtttgtaccc cttctggttt ttccattgtg ttttgggaaa      60
ttccctattt acacgatacc agacaagctt ggtccctgga gcccgattga catacatcac    120
ctcagctgcc caaacaattt ggtagtggag gacgaaggat gcaccaacct gtcagggttc    180
tcctacatgg aacttaaagt tggatacatc ttagccataa aaatgaacgg gttcacttgc    240
acaggcgttg tgacggaggc tgaaacctac actaacttcg ttggttatgt cacaaccacg    300
ttcaaaagaa agcatttccg cccaacacca gatgcatgta gagccgcgta caactggaag    360
atggccggtg accccagata tgaagagtct ctacacaatc cgtaccctga ctaccactgg    420
cttcgaactg taaaaaccac caaggagtct ctcgttatca tatctccaag tgtggcagat    480
ttggacccat atgacagatc ccttcactcg agggtcttcc ctagcgggaa gtgcccagga    540
gtagcggtgt cttctaccta ctgctccact aaccacgatt acaccatttg gatgcccgag    600
aatccgagac tagggatgtc ttgtgacatt tttaccaata gtagagggaa gagagcatcc    660
aaagggagtg agacttgcgg cttttgtaga tgaaagaggcc tatataagtc tttaaaagga    720
gcatgcaaac tcaagttatg tggagttcta ggacttagac ttatggatgg aacatgggtc    780
gcgatgcaaa catcaaatga aaccaaatgg tgccctcccg atcagttggt gaacctgcac    840
gactttcgct cagacgaaat tgagcacctt gttgtagagg agttggtcag gaagagagag    900
gagtgtctgg atgcactaga gtccatcatg acaaccaagt cagtgagttt cagacgtctc    960
agtcatttaa gaaaacttgt ccctgggttt ggaaaagcat ataccatatt caacaagacc  1020
ttgatggaag ccgatgctca ctacaagtca gtcagaactt ggaatgagat cctcccttca  1080
aaagggtgtt taagagttgg ggggaggtgt catcctcatg tgaacggggt gtttttcaat  1140
ggtataatat taggacctga cggcaatgtc ttaatcccag agatgcaatc atccctcctc  1200
cagcaacata tggagttgtt ggaatcctcg gttatccccc ttgtgcaccc cctggcagac  1260
ccgtctaccg ttttcaagga cggtgacgag gctgaggatt ttgttgaagt tcaccttccc  1320
gatgtgcaca atcaggtctc aggagttgac ttgggtctcc cgaactgggg gaagtatgta  1380
ttactgagtg caggggccct gactgccttg atgttgataa ttttcctgat gacatgttgt  1440
agaagagtca atcgatcaga acctacgcaa cacaatctca gagggacagg gagggaggtg  1500
tcagtcactc cccaaagcgg gaagatcata tcttcatggg aatcacacaa gagtgggggt  1560
cagaccagac tgtga                                                   1575

<210> SEQ ID NO 2
```

<211> LENGTH: 524
<212> TYPE: PRT
<213> ORGANISM: Rabies virus

<400> SEQUENCE: 2

```
Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
50                  55                  60

Leu Lys Val Gly Tyr Ile Leu Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Pro Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Ala Ser Lys Gly Ser Glu
210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Arg Lys Arg Glu Glu Cys Leu Asp
290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Leu Pro Ser Lys Gly Cys Leu Arg Val Gly Gly
        355                 360                 365

Arg Cys His Pro His Val Asn Gly Val Phe Phe Asn Gly Ile Ile Leu
370                 375                 380

Gly Pro Asp Gly Asn Val Leu Ile Pro Glu Met Gln Ser Ser Leu Leu
```

-continued

```
385                 390                 395                 400

Gln Gln His Met Glu Leu Leu Glu Ser Ser Val Ile Pro Leu Val His
                405                 410                 415

Pro Leu Ala Asp Pro Ser Thr Val Phe Lys Asp Gly Asp Glu Ala Glu
            420                 425                 430

Asp Phe Val Glu Val His Leu Pro Asp Val His Asn Gln Val Ser Gly
        435                 440                 445

Val Asp Leu Gly Leu Pro Asn Trp Gly Lys Tyr Val Leu Leu Ser Ala
    450                 455                 460

Gly Ala Leu Thr Ala Leu Met Leu Ile Ile Phe Leu Met Thr Cys Cys
465                 470                 475                 480

Arg Arg Val Asn Arg Ser Glu Pro Thr Gln His Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser His Lys Ser Gly Gly Gln Thr Arg Leu
        515                 520
```

<210> SEQ ID NO 3
<211> LENGTH: 1575
<212> TYPE: DNA
<213> ORGANISM: Rabies virus

<400> SEQUENCE: 3
```
atggttcctc aggctctcct gtttgtaccc cttctggttt ttccattgtg ttttgggaaa     60
ttccctattt acacgatacc agacaagctt ggtccctgga gcccgattga catacatcac    120
ctcagctgcc caaacaattt gatagtggag gacgaaggat gcaccaacct gtcagggttc    180
tcctacatgg aacttaaagt tggatacatc ttagccataa aaatgaacgg gttcacttgc    240
acaggcgttg tgacggaggc tgaaacctac actaacttcg ttggttatgt cacaaccacg    300
ttcaaaagaa agcatttccg cccaacacca gatgcatgta gagccgcgta caactggaag    360
atggccggtg accccagata tgaagagtct ctacacaatc cgtaccctga ctaccgctgg    420
cttcgaactg taaaaaccac caaggagtct ctcgttatca tatctccaag tgtggcagat    480
ttggacccat atgacagatc ccttcactcg agggtcttcc ctagcgggaa gtgctcagga    540
gtagcggtgt cttctaccta ctgctccact aaccacgatt acaccatttg gatgcccgag    600
aatccgagac tagggatgtc ttgtgacatt tttaccaata gtagagggaa gagagtatcc    660
aaagggagtg agacttgcgg ctttgtagat gaaagaggcc tatataagtc tttaaaagga    720
gcatgcaaac tcaagttatg tggagttcta ggacttagac ttatggatgg aacatgggtc    780
gcgatgcaaa catcaaatga aaccaaatgg tgccctcccg atcagttggt gaacctgcac    840
gactttcgct cagacgaaat tgagcacctt gttgtagagg agttggtcag gaagagagag    900
gagtgtctgg atgcactaga gtccatcatg acaaccaagt cagtgagttt cagacgtctc    960
agtcatttaa gaaaacttgt ccctgggttt ggaaaagcat ataccatatt caacaagacc   1020
ttgatggaag ccgatgctca ctacaagtca gtcagaactt ggaatgagat cctcccttca   1080
aaagggtgtt taagagttgg ggggaggtgt catcctcatg tgaacggggt gtttttcaat   1140
ggtataatat taggacctga cggcaatgtc ttaatcccag agatgcaatc atccctcctc   1200
cagcaacata tggagttgtt ggaatcctcg gttatccccc ttgtgcaccc cctggcagac   1260
ccgtctaccg ttttcaagga cggtgacgag gctgaggatt ttgttgaagt tcaccttccc   1320
gatgtgcaca atcaggtctc aggagttgac ttgggtctcc cgaactgggg gaagtatgta   1380
```

```
ttactgagtg cagggcccct gactgccttg atgttgataa ttttcctgat gacatgttgt   1440
agaagagtca atcgatcaga acctacgcaa ctcaatctca gagggacagg gagggaggtg   1500
tcagtcactc cccaaagcgg gaagatcata tcttcatggg aatcacacaa gagtgggggt   1560
gagaccagac tgtga                                                    1575

<210> SEQ ID NO 4
<211> LENGTH: 524
<212> TYPE: PRT
<213> ORGANISM: Rabies virus

<400> SEQUENCE: 4

Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
                20                  25                  30

Trp Ser Pro Ile Asp Ile His His Leu Ser Cys Pro Asn Asn Leu Ile
            35                  40                  45

Val Glu Asp Glu Gly Cys Thr Asn Leu Ser Gly Phe Ser Tyr Met Glu
        50                  55                  60

Leu Lys Val Gly Tyr Ile Leu Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
                100                 105                 110

Cys Arg Ala Ala Tyr Asn Trp Lys Met Ala Gly Asp Pro Arg Tyr Glu
            115                 120                 125

Glu Ser Leu His Asn Pro Tyr Pro Asp Tyr Arg Trp Leu Arg Thr Val
        130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Val Ser Lys Gly Ser Glu
210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Arg Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335
```

```
Phe Asn Lys Thr Leu Met Glu Ala Asp Ala His Tyr Lys Ser Val Arg
            340                 345                 350

Thr Trp Asn Glu Ile Leu Pro Ser Lys Gly Cys Leu Arg Val Gly Gly
        355                 360                 365

Arg Cys His Pro His Val Asn Gly Val Phe Phe Asn Gly Ile Ile Leu
    370                 375                 380

Gly Pro Asp Gly Asn Val Leu Ile Pro Glu Met Gln Ser Ser Leu Leu
385                 390                 395                 400

Gln Gln His Met Glu Leu Leu Glu Ser Ser Val Ile Pro Leu Val His
                405                 410                 415

Pro Leu Ala Asp Pro Ser Thr Val Phe Lys Asp Gly Asp Glu Ala Glu
            420                 425                 430

Asp Phe Val Glu Val His Leu Pro Asp Val His Asn Gln Val Ser Gly
        435                 440                 445

Val Asp Leu Gly Leu Pro Asn Trp Gly Lys Tyr Val Leu Leu Ser Ala
    450                 455                 460

Gly Ala Leu Thr Ala Leu Met Leu Ile Ile Phe Leu Met Thr Cys Cys
465                 470                 475                 480

Arg Arg Val Asn Arg Ser Glu Pro Thr Gln Leu Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser His Lys Ser Gly Gly Glu Thr Arg Leu
        515                 520

<210> SEQ ID NO 5
<211> LENGTH: 132
<212> TYPE: DNA
<213> ORGANISM: Rabies virus

<400> SEQUENCE: 5
agaagagtca atcgatcaga acctacgcaa cacaatctca gagggacagg gagggaggtg      60
tcagtcactc cccaaagcgg gaagatcata tcttcatggg aatcacacaa gagtgggggt     120
cagaccagac tg                                                        132

<210> SEQ ID NO 6
<211> LENGTH: 44
<212> TYPE: PRT
<213> ORGANISM: Rabies virus

<400> SEQUENCE: 6

Arg Arg Val Asn Arg Ser Glu Pro Thr Gln His Asn Leu Arg Gly Thr
1               5                   10                  15

Gly Arg Glu Val Ser Val Thr Pro Gln Ser Gly Lys Ile Ile Ser Ser
            20                  25                  30

Trp Glu Ser His Lys Ser Gly Gly Gln Thr Arg Leu
        35                  40

<210> SEQ ID NO 7
<211> LENGTH: 132
<212> TYPE: DNA
<213> ORGANISM: Rabies virus

<400> SEQUENCE: 7
agaagagtca atcgatcaga acctacgcaa ctcaatctca gagggacagg gagggaggtg      60
tcagtcactc cccaaagcgg gaagatcata tcttcatggg aatcacacaa gagtgggggt     120
```

-continued gagaccagac tg                                                    132

<210> SEQ ID NO 8
<211> LENGTH: 44
<212> TYPE: PRT
<213> ORGANISM: Rabies virus

<400> SEQUENCE: 8

Arg Arg Val Asn Arg Ser Glu Pro Thr Gln Leu Asn Leu Arg Gly Thr
1               5                   10                  15

Gly Arg Glu Val Ser Val Thr Pro Gln Ser Gly Lys Ile Ile Ser Ser
            20                  25                  30

Trp Glu Ser His Lys Ser Gly Gly Glu Thr Arg Leu
        35                  40

<210> SEQ ID NO 9
<211> LENGTH: 12
<212> TYPE: DNA
<213> ORGANISM: Rabies virus

<400> SEQUENCE: 9
cagaccagac tg                                                    12

<210> SEQ ID NO 10
<211> LENGTH: 4
<212> TYPE: PRT
<213> ORGANISM: Rabies virus

<400> SEQUENCE: 10

Gln Thr Arg Leu
1

<210> SEQ ID NO 11
<211> LENGTH: 12
<212> TYPE: DNA
<213> ORGANISM: Rabies virus

<400> SEQUENCE: 11
gagaccagac tg                                                    12

<210> SEQ ID NO 12
<211> LENGTH: 4
<212> TYPE: PRT
<213> ORGANISM: Rabies virus

<400> SEQUENCE: 12

Glu Thr Arg Leu
1

<210> SEQ ID NO 13
<211> LENGTH: 4
<212> TYPE: PRT
<213> ORGANISM: Rabies virus
<220> FEATURE:
<221> NAME/KEY: MISC_FEATURE
<222> LOCATION: (1)..(1)
<223> OTHER INFORMATION: Xaa = any amino acid
<220> FEATURE:
<221> NAME/KEY: MISC_FEATURE
<222> LOCATION: (2)..(2)
<223> OTHER INFORMATION: Xaa = T or S or I
<220> FEATURE:
<221> NAME/KEY: MISC_FEATURE
<222> LOCATION: (3)..(3)
<223> OTHER INFORMATION: Xaa = any amino acid

```
<220> FEATURE:
<221> NAME/KEY: MISC_FEATURE
<222> LOCATION: (4)..(4)
<223> OTHER INFORMATION: Xaa = L or V

<400> SEQUENCE: 13

Xaa Xaa Xaa Xaa
1

<210> SEQ ID NO 14
<211> LENGTH: 4
<212> TYPE: PRT
<213> ORGANISM: Rabies virus
<220> FEATURE:
<221> NAME/KEY: MISC_FEATURE
<222> LOCATION: (1)..(1)
<223> OTHER INFORMATION: Xaa = any amino acid except E
<220> FEATURE:
<221> NAME/KEY: MISC_FEATURE
<222> LOCATION: (2)..(2)
<223> OTHER INFORMATION: Xaa = T or S or I
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = L or V

<400> SEQUENCE: 14

Xaa Xaa Xaa Xaa
1

<210> SEQ ID NO 15
<211> LENGTH: 524
<212> TYPE: PRT
<213> ORGANISM: Rabies virus

<400> SEQUENCE: 15

Met Val Pro Gln Val Leu Leu Phe Val Leu Leu Leu Gly Phe Ser Leu
1               5                   10                  15

Cys Phe Gly Lys Phe Pro Ile Tyr Thr Ile Pro Asp Lys Leu Gly Pro
                20                  25                  30

Trp Ser Pro Ile Asp Ile His His Leu Arg Cys Pro Asn Asn Leu Val
            35                  40                  45

Val Glu Asp Glu Gly Cys Ile Asn Leu Ser Gly Phe Ser Tyr Met Glu
    50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
                100                 105                 110

Cys Arg Ala Ala Tyr Asn Trp Lys Met Ala Gly Asp Pro Arg Tyr Glu
            115                 120                 125

Glu Ser Leu Gln Asn Pro Tyr Pro Asp Tyr His Trp Leu Arg Thr Val
    130                 135                 140

Arg Thr Thr Lys Glu Ser Leu Ile Ile Ile Ser Pro Ser Val Thr Asp
145                 150                 155                 160

Leu Asp Pro Tyr Asp Lys Ser Leu His Ser Arg Val Phe Pro Gly Gly
                165                 170                 175

Lys Cys Ser Gly Ile Thr Val Ser Ser Thr Tyr Cys Ser Thr Asn His
```

```
                180                 185                 190
Asp Tyr Thr Ile Trp Met Pro Glu Asn Pro Arg Pro Gly Thr Pro Cys
            195                 200                 205

Asp Ile Phe Thr Asn Ser Arg Gly Lys Arg Ala Ser Asn Gly Asn Lys
        210                 215                 220

Thr Cys Gly Phe Val Asp Glu Arg Gly Leu Tyr Lys Ser Leu Lys Gly
225                 230                 235                 240

Ala Cys Arg Leu Lys Leu Cys Gly Val Leu Gly Leu Arg Leu Met Asp
                245                 250                 255

Gly Thr Trp Val Ala Met Gln Thr Ser Asp Glu Thr Lys Trp Cys Ser
            260                 265                 270

Pro Asp Gln Leu Val Asn Leu His Asp Phe Arg Ser Asp Glu Ile Glu
        275                 280                 285

His Leu Val Val Glu Glu Leu Val Lys Lys Arg Glu Glu Cys Leu Asp
    290                 295                 300

Thr Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Ile Pro Ser Lys Gly Cys Leu Lys Val Gly Gly
        355                 360                 365

Arg Cys His Pro His Val Asn Gly Val Phe Phe Asn Gly Ile Ile Leu
    370                 375                 380

Gly Pro Asp Asp Arg Val Leu Ile Pro Glu Met Gln Ser Ser Leu Leu
385                 390                 395                 400

Arg Gln His Met Glu Leu Leu Glu Ser Ser Val Ile Pro Leu Met His
                405                 410                 415

Pro Leu Ala Asp Pro Ser Thr Val Phe Lys Glu Gly Asp Glu Ala Glu
            420                 425                 430

Asp Phe Val Glu Val His Leu Pro Asp Val Tyr Lys Gln Ile Ser Gly
        435                 440                 445

Val Asp Leu Gly Leu Pro Asn Trp Gly Lys Tyr Val Leu Met Thr Ala
    450                 455                 460

Gly Ala Met Ile Gly Leu Val Leu Ile Phe Ser Leu Met Thr Trp Cys
465                 470                 475                 480

Arg Arg Ala Asn Arg Pro Glu Ser Lys Gln Arg Ser Phe Gly Gly Thr
                485                 490                 495

Gly Gly Asn Val Ser Val Thr Ser Gln Ser Gly Lys Val Ile Pro Ser
            500                 505                 510

Trp Glu Ser Tyr Lys Ser Gly Gly Glu Ile Arg Leu
        515                 520

<210> SEQ ID NO 16
<211> LENGTH: 524
<212> TYPE: PRT
<213> ORGANISM: Rabies virus

<400> SEQUENCE: 16

Met Val Pro Gln Val Leu Leu Phe Val Pro Leu Leu Gly Phe Ser Leu
1               5                   10                  15

Cys Phe Gly Lys Phe Pro Ile Tyr Thr Ile Pro Asp Glu Leu Gly Pro
            20                  25                  30
```

```
Trp Ser Pro Ile Asp Ile His His Leu Ser Cys Pro Asn Asn Leu Val
         35                  40                  45

Val Glu Asp Glu Gly Cys Thr Asn Leu Ser Glu Phe Ser Tyr Met Glu
 50                  55                  60

Leu Lys Val Gly Tyr Ile Ser Ala Ile Lys Val Asn Gly Phe Thr Cys
 65                  70                  75                  80

Thr Gly Val Val Thr Glu Ala Glu Thr Tyr Thr Asn Phe Val Gly Tyr
                 85                  90                  95

Val Thr Thr Thr Phe Lys Arg Lys His Phe Arg Pro Thr Pro Asp Ala
             100                 105                 110

Cys Arg Ala Ala Tyr Asn Trp Lys Met Ala Gly Asp Pro Arg Tyr Glu
         115                 120                 125

Glu Ser Leu His Asn Pro Tyr Pro Asp Tyr His Trp Leu Arg Thr Val
 130                 135                 140

Arg Thr Thr Lys Glu Ser Leu Ile Ile Ile Ser Pro Ser Val Thr Asp
 145                 150                 155                 160

Leu Asp Pro Tyr Asp Lys Ser Leu His Ser Arg Val Phe Pro Gly Gly
                 165                 170                 175

Lys Cys Ser Gly Ile Thr Val Ser Ser Thr Tyr Cys Ser Thr Asn His
             180                 185                 190

Asp Tyr Thr Ile Trp Met Pro Glu Asp Pro Arg Pro Arg Thr Pro Cys
         195                 200                 205

Asn Ile Phe Thr Asn Ser Arg Gly Lys Arg Ala Ser Lys Gly Asn Lys
 210                 215                 220

Thr Cys Gly Phe Val Asp Glu Arg Gly Leu Tyr Lys Ser Leu Lys Gly
 225                 230                 235                 240

Ala Cys Arg Leu Lys Leu Cys Gly Val Leu Gly Leu Arg Leu Met Asp
                 245                 250                 255

Gly Thr Trp Val Ala Met Gln Thr Ser Asp Glu Thr Lys Trp Cys Pro
             260                 265                 270

Pro Asp Gln Leu Val Asn Leu His Asp Phe His Ser Asp Glu Ile Glu
         275                 280                 285

His Leu Val Val Glu Glu Leu Val Lys Lys Arg Glu Glu Cys Leu Asp
 290                 295                 300

Ala Leu Glu Ser Ile Met Thr Thr Lys Ser Val Ser Phe Arg Arg Leu
 305                 310                 315                 320

Ser His Leu Arg Lys Leu Val Pro Gly Phe Gly Lys Ala Tyr Thr Ile
                 325                 330                 335

Phe Asn Lys Thr Leu Met Glu Ala Asp Ala His Tyr Lys Ser Val Arg
             340                 345                 350

Thr Trp Asn Glu Ile Ile Pro Ser Lys Gly Cys Leu Lys Val Gly Gly
         355                 360                 365

Arg Cys His Pro His Val Asn Gly Val Phe Phe Asn Gly Ile Ile Leu
 370                 375                 380

Gly Pro Asp Gly His Val Leu Ile Pro Glu Met Gln Ser Ser Leu Leu
 385                 390                 395                 400

Gln Gln His Met Glu Leu Leu Lys Ser Ser Val Ile Pro Leu Met His
                 405                 410                 415

Pro Leu Ala Asp Pro Ser Thr Val Phe Lys Glu Gly Asp Glu Ala Glu
             420                 425                 430

Asp Phe Val Glu Val His Leu Pro Asp Val Tyr Lys Arg Ile Ser Gly
         435                 440                 445

Val Asp Leu Gly Leu Pro Asn Trp Gly Lys Tyr Val Leu Met Thr Ala
```

```
            450             455             460
Gly Ala Met Ile Gly Leu Val Leu Ile Phe Ser Leu Met Thr Trp Cys
465                 470                 475                 480

Arg Arg Ala Asn Arg Pro Glu Ser Lys Gln Arg Ser Phe Gly Gly Thr
                485                 490                 495

Gly Arg Asn Val Ser Val Thr Ser Gln Ser Gly Lys Val Ile Pro Ser
                500                 505                 510

Trp Glu Ser Tyr Lys Ser Gly Gly Glu Ile Arg Leu
                515                 520
```

<210> SEQ ID NO 17
<211> LENGTH: 524
<212> TYPE: PRT
<213> ORGANISM: Rabies virus

<400> SEQUENCE: 17

```
Met Val Pro Gln Val Leu Leu Phe Val Pro Leu Leu Gly Phe Ser Leu
1               5                   10                  15

Cys Phe Gly Lys Phe Pro Ile Tyr Thr Ile Pro Asp Lys Leu Gly Pro
                20                  25                  30

Trp Ser Pro Ile Asp Ile His His Leu Ser Cys Pro Asn Asn Leu Val
            35                  40                  45

Val Glu Asp Glu Gly Cys Thr Asn Leu Ser Glu Phe Ser Tyr Met Glu
50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
                100                 105                 110

Cys Arg Ala Ala Tyr Asn Trp Lys Met Ala Gly Asp Pro Arg Tyr Glu
            115                 120                 125

Glu Ser Leu His Asn Pro Tyr Pro Asp Tyr His Trp Leu Arg Thr Val
130                 135                 140

Arg Thr Thr Lys Glu Ser Leu Ile Ile Ile Ser Pro Ser Val Thr Asp
145                 150                 155                 160

Leu Asp Pro Tyr Asp Lys Ser Leu His Ser Arg Val Phe Pro Gly Gly
                165                 170                 175

Lys Cys Ser Gly Ile Thr Val Ser Ser Thr Tyr Cys Ser Thr Asn His
            180                 185                 190

Asp Tyr Thr Ile Trp Met Pro Glu Asn Pro Arg Pro Arg Thr Pro Cys
            195                 200                 205

Asp Ile Phe Thr Asn Ser Arg Gly Lys Arg Ala Ser Lys Gly Asn Lys
210                 215                 220

Thr Cys Gly Phe Val Asp Glu Arg Gly Leu Tyr Lys Ser Leu Lys Gly
225                 230                 235                 240

Ala Cys Arg Leu Lys Leu Cys Gly Val Leu Gly Leu Arg Leu Met Asp
                245                 250                 255

Gly Thr Trp Val Ala Met Gln Thr Ser Asp Glu Thr Lys Trp Cys Pro
                260                 265                 270

Pro Asp Gln Leu Val Asn Leu His Asp Phe Arg Ser Asp Glu Ile Glu
            275                 280                 285

His Leu Val Val Glu Glu Leu Val Lys Lys Arg Glu Glu Cys Leu Asp
            290                 295                 300
```

```
Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Ile Pro Ser Lys Gly Cys Leu Lys Val Gly Gly
        355                 360                 365

Arg Cys His Pro His Val Asn Gly Val Phe Phe Asn Gly Ile Ile Leu
    370                 375                 380

Gly Pro Asp Gly His Val Leu Ile Pro Glu Met Gln Ser Ser Leu Leu
385                 390                 395                 400

Gln Gln His Met Glu Leu Leu Lys Ser Ser Val Ile Pro Leu Met His
                405                 410                 415

Pro Leu Ala Asp Pro Ser Thr Val Phe Lys Glu Gly Asp Glu Ala Glu
            420                 425                 430

Asp Phe Val Glu Val His Leu Pro Asp Val Tyr Lys Gln Ile Ser Gly
        435                 440                 445

Val Asp Leu Gly Leu Pro Asn Trp Gly Lys Tyr Val Leu Met Thr Ala
450                 455                 460

Gly Ala Met Ile Gly Leu Val Leu Ile Phe Ser Leu Met Thr Trp Cys
465                 470                 475                 480

Arg Arg Ala Asn Arg Pro Glu Ser Lys Gln Arg Ser Phe Gly Gly Thr
                485                 490                 495

Gly Arg Asn Val Ser Val Thr Ser Gln Ser Gly Lys Val Ile Pro Ser
            500                 505                 510

Trp Glu Ser Tyr Lys Ser Gly Gly Glu Ile Arg Leu
        515                 520

<210> SEQ ID NO 18
<211> LENGTH: 523
<212> TYPE: PRT
<213> ORGANISM: Rabies virus

<400> SEQUENCE: 18

Met Val Pro Gln Val Leu Leu Phe Val Leu Leu Leu Gly Phe Ser Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Arg Cys Pro Asn Asn Leu Val
        35                  40                  45

Val Glu Asp Glu Gly Cys Thr Asn Leu Ser Gly Phe Ser Tyr Met Glu
50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu Gln Asn Pro Tyr Pro Asp Tyr His Trp Leu Arg Thr Val
    130                 135                 140

Arg Thr Thr Lys Glu Ser Leu Ile Ile Ile Ser Pro Ser Val Thr Asp
145                 150                 155                 160
```

Leu Asp Pro Tyr Asp Lys Ser Leu His Ser Arg Val Phe Pro Gly Gly
                165                 170                 175

Lys Cys Ser Gly Ile Thr Val Ser Thr Tyr Cys Ser Thr Asn His Asp
            180                 185                 190

Tyr Thr Ile Trp Met Pro Glu Asp Pro Arg Pro Gly Thr Pro Cys Asp
        195                 200                 205

Ile Phe Thr Asn Ser Arg Gly Lys Arg Ala Ser Asn Gly Asn Lys Thr
    210                 215                 220

Cys Gly Phe Val Asp Glu Arg Gly Leu Tyr Lys Ser Leu Lys Gly Ala
225                 230                 235                 240

Cys Arg Leu Lys Leu Cys Gly Val Leu Gly Leu Arg Leu Met Asp Gly
                245                 250                 255

Thr Trp Val Ala Met Gln Thr Ser Asp Glu Thr Lys Trp Cys Ser Pro
            260                 265                 270

Asp Gln Leu Val Asn Leu His Asp Phe Arg Ser Asn Glu Ile Glu His
        275                 280                 285

Leu Val Val Glu Asp Leu Val Lys Lys Arg Glu Glu Cys Leu Asp Thr
    290                 295                 300

Leu Glu Ser Ile Met Thr Thr Lys Ser Val Ser Phe Arg Arg Leu Ser
305                 310                 315                 320

His Leu Arg Lys Leu Val Pro Gly Phe Gly Lys Ala Tyr Thr Ile Phe
                325                 330                 335

Asn Lys Thr Leu Met Glu Ala Asp Val His Tyr Lys Ser Val Arg Thr
            340                 345                 350

Trp Asn Glu Ile Ile Pro Ser Lys Gly Cys Leu Lys Val Gly Gly Arg
        355                 360                 365

Cys His Pro His Val Asn Gly Val Phe Phe Asn Gly Ile Ile Leu Gly
370                 375                 380

Pro Asp Asp Arg Val Leu Ile Pro Glu Met Gln Ser Ser Leu Leu Arg
385                 390                 395                 400

Gln His Met Glu Leu Leu Glu Ser Ser Val Ile Pro Leu Met His Pro
                405                 410                 415

Leu Ala Asp Pro Ser Thr Val Phe Lys Glu Gly Asp Glu Ala Glu Asp
            420                 425                 430

Phe Val Glu Val His Leu Pro Asp Val Tyr Lys Lys Ile Ser Gly Val
        435                 440                 445

Asp Leu Gly Leu Pro Asn Trp Gly Lys Tyr Val Leu Met Thr Ala Gly
450                 455                 460

Ala Met Ile Gly Leu Val Leu Ile Phe Ser Leu Met Thr Trp Cys Arg
465                 470                 475                 480

Arg Ala Asn Arg Pro Glu Ser Lys Gln Arg Ser Phe Gly Gly Thr Gly
                485                 490                 495

Gly Asn Val Ser Val Thr Ser Gln Ser Gly Lys Val Ile Pro Ser Trp
            500                 505                 510

Glu Ser Tyr Lys Ser Gly Gly Glu Ile Arg Leu
        515                 520

<210> SEQ ID NO 19
<211> LENGTH: 44
<212> TYPE: PRT
<213> ORGANISM: Rabies virus

<400> SEQUENCE: 19

Arg Arg Val Asn Arg Ser Glu Pro Thr Gln Leu Asn Leu Arg Gly Thr

```
1               5                   10                  15
Gly Arg Glu Val Ser Val Thr Pro Gln Ser Gly Lys Ile Ile Ser Ser
            20                  25                  30

Trp Glu Ser His Lys Ser Gly Gly Gln Thr Arg Leu
        35                  40
```

<210> SEQ ID NO 20
<211> LENGTH: 44
<212> TYPE: PRT
<213> ORGANISM: Rabies virus

<400> SEQUENCE: 20

```
Arg Arg Val Asn Arg Ser Glu Pro Thr Gln His Asn Leu Arg Gly Thr
1               5                   10                  15

Gly Arg Glu Val Ser Val Thr Pro Gln Ser Gly Lys Ile Ile Ser Ser
            20                  25                  30

Trp Glu Ser His Lys Ser Gly Gly Glu Thr Arg Leu
        35                  40
```

<210> SEQ ID NO 21
<211> LENGTH: 19
<212> TYPE: PRT
<213> ORGANISM: Rabies virus

<400> SEQUENCE: 21

```
Met Val Pro Gln Ala Leu Leu Phe Val Pro Leu Leu Val Phe Pro Leu
1               5                   10                  15

Cys Phe Gly
```

<210> SEQ ID NO 22
<211> LENGTH: 439
<212> TYPE: PRT
<213> ORGANISM: Rabies virus

<400> SEQUENCE: 22

```
Lys Phe Pro Ile Tyr Thr Ile Pro Asp Lys Leu Gly Pro Trp Ser Pro
1               5                   10                  15

Ile Asp Ile His His Leu Ser Cys Pro Asn Asn Leu Val Val Glu Asp
            20                  25                  30

Glu Gly Cys Thr Asn Leu Ser Gly Phe Ser Tyr Met Glu Leu Lys Val
        35                  40                  45

Gly Tyr Ile Leu Ala Ile Lys Met Asn Gly Phe Thr Cys Thr Gly Val
    50                  55                  60

Val Thr Glu Ala Glu Thr Tyr Thr Asn Phe Val Gly Tyr Val Thr Thr
65                  70                  75                  80

Thr Phe Lys Arg Lys His Phe Arg Pro Thr Pro Asp Ala Cys Arg Ala
                85                  90                  95

Ala Tyr Asn Trp Lys Met Ala Gly Asp Pro Arg Tyr Glu Glu Ser Leu
            100                 105                 110

His Asn Pro Tyr Pro Asp Tyr His Trp Leu Arg Thr Val Lys Thr Thr
        115                 120                 125

Lys Glu Ser Leu Val Ile Ile Ser Pro Ser Val Ala Asp Leu Asp Pro
    130                 135                 140

Tyr Asp Arg Ser Leu His Ser Arg Val Phe Pro Ser Gly Lys Cys Pro
145                 150                 155                 160

Gly Val Ala Val Ser Ser Thr Tyr Cys Ser Thr Asn His Asp Tyr Thr
                165                 170                 175
```

```
Ile Trp Met Pro Glu Asn Pro Arg Leu Gly Met Ser Cys Asp Ile Phe
        180                 185                 190

Thr Asn Ser Arg Gly Lys Arg Ala Ser Lys Gly Ser Glu Thr Cys Gly
        195                 200                 205

Phe Val Asp Glu Arg Gly Leu Tyr Lys Ser Leu Lys Gly Ala Cys Lys
        210                 215                 220

Leu Lys Leu Cys Gly Val Leu Gly Leu Arg Leu Met Asp Gly Thr Trp
225                 230                 235                 240

Val Ala Met Gln Thr Ser Asn Glu Thr Lys Trp Cys Pro Pro Asp Gln
        245                 250                 255

Leu Val Asn Leu His Asp Phe Arg Ser Asp Glu Ile Glu His Leu Val
        260                 265                 270

Val Glu Glu Leu Val Arg Lys Arg Glu Glu Cys Leu Asp Ala Leu Glu
        275                 280                 285

Ser Ile Met Thr Thr Lys Ser Val Ser Phe Arg Arg Leu Ser His Leu
        290                 295                 300

Arg Lys Leu Val Pro Gly Phe Gly Lys Ala Tyr Thr Ile Phe Asn Lys
305                 310                 315                 320

Thr Leu Met Glu Ala Asp Ala His Tyr Lys Ser Val Arg Thr Trp Asn
        325                 330                 335

Glu Ile Leu Pro Ser Lys Gly Cys Leu Arg Val Gly Gly Arg Cys His
        340                 345                 350

Pro His Val Asn Gly Val Phe Phe Asn Gly Ile Ile Leu Gly Pro Asp
        355                 360                 365

Gly Asn Val Leu Ile Pro Glu Met Gln Ser Ser Leu Leu Gln Gln His
        370                 375                 380

Met Glu Leu Leu Glu Ser Ser Val Ile Pro Leu Val His Pro Leu Ala
385                 390                 395                 400

Asp Pro Ser Thr Val Phe Lys Asp Gly Asp Glu Ala Glu Asp Phe Val
        405                 410                 415

Glu Val His Leu Pro Asp Val His Asn Gln Val Ser Gly Val Asp Leu
        420                 425                 430

Gly Leu Pro Asn Trp Gly Lys
        435

<210> SEQ ID NO 23
<211> LENGTH: 22
<212> TYPE: PRT
<213> ORGANISM: Rabies virus

<400> SEQUENCE: 23

Tyr Val Leu Leu Ser Ala Gly Ala Leu Thr Ala Leu Met Leu Ile Ile
1               5                   10                  15

Phe Leu Met Thr Cys Cys
            20

<210> SEQ ID NO 24
<211> LENGTH: 45
<212> TYPE: PRT
<213> ORGANISM: Artificial Sequence
<220> FEATURE:
<223> OTHER INFORMATION: M + cytoplasmic domain of non-apoptotic rabies
      virus G protein
```

```
<400> SEQUENCE: 24

Met Arg Arg Val Asn Arg Ser Glu Pro Thr Gln His Asn Leu Arg Gly
1               5                   10                  15

Thr Gly Arg Glu Val Ser Val Thr Pro Gln Ser Gly Lys Ile Ile Ser
            20                  25                  30

Ser Trp Glu Ser His Lys Ser Gly Gly Gln Thr Arg Leu
        35                  40                  45

<210> SEQ ID NO 25
<211> LENGTH: 66
<212> TYPE: PRT
<213> ORGANISM: Rabies virus

<400> SEQUENCE: 25

Tyr Val Leu Leu Ser Ala Gly Ala Leu Thr Ala Leu Met Leu Ile Ile
1               5                   10                  15

Phe Leu Met Thr Cys Cys Arg Arg Val Asn Arg Ser Glu Pro Thr Gln
            20                  25                  30

His Asn Leu Arg Gly Thr Gly Arg Glu Val Ser Val Thr Pro Gln Ser
        35                  40                  45

Gly Lys Ile Ile Ser Ser Trp Glu Ser His Lys Ser Gly Gly Gln Thr
    50                  55                  60

Arg Leu
65

<210> SEQ ID NO 26
<211> LENGTH: 68
<212> TYPE: PRT
<213> ORGANISM: Artificial Sequence
<220> FEATURE:
<223> OTHER INFORMATION: GK + transmembrane and cytoplasmic domains of
      non-apoptotic rabies virus G protein

<400> SEQUENCE: 26

Gly Lys Tyr Val Leu Leu Ser Ala Gly Ala Leu Thr Ala Leu Met Leu
1               5                   10                  15

Ile Ile Phe Leu Met Thr Cys Cys Arg Arg Val Asn Arg Ser Glu Pro
            20                  25                  30

Thr Gln His Asn Leu Arg Gly Thr Gly Arg Glu Val Ser Val Thr Pro
        35                  40                  45

Gln Ser Gly Lys Ile Ile Ser Ser Trp Glu Ser His Lys Ser Gly Gly
    50                  55                  60

Gln Thr Arg Leu
65

<210> SEQ ID NO 27
<211> LENGTH: 87
<212> TYPE: PRT
<213> ORGANISM: Artificial Sequence
<220> FEATURE:
<223> OTHER INFORMATION: Signal peptide of non-apoptotic rabies virus G
      protein + SEQ ID NO: 26

<400> SEQUENCE: 27

Met Val Pro Gln Ala Leu Leu Phe Val Pro Leu Leu Val Phe Pro Leu
1               5                   10                  15

Cys Phe Gly Gly Lys Tyr Val Leu Leu Ser Ala Gly Ala Leu Thr Ala
            20                  25                  30

Leu Met Leu Ile Ile Phe Leu Met Thr Cys Cys Arg Arg Val Asn Arg
```

```
                35                  40                  45
Ser Glu Pro Thr Gln His Asn Leu Arg Gly Thr Gly Arg Glu Val Ser
    50                  55                  60

Val Thr Pro Gln Ser Gly Lys Ile Ile Ser Ser Trp Glu Ser His Lys
65                  70                  75                  80

Ser Gly Gly Gln Thr Arg Leu
                85

<210> SEQ ID NO 28
<211> LENGTH: 34
<212> TYPE: DNA
<213> ORGANISM: Artificial Sequence
<220> FEATURE:
<223> OTHER INFORMATION: primer

<400> SEQUENCE: 28
ggccgctagc atggttcctc aggctctcct gttt                              34

<210> SEQ ID NO 29
<211> LENGTH: 37
<212> TYPE: DNA
<213> ORGANISM: Artificial Sequence
<220> FEATURE:
<223> OTHER INFORMATION: primer

<400> SEQUENCE: 29
ggccgctagc atgagaagag tcaatcgatc agaacct                           37

<210> SEQ ID NO 30
<211> LENGTH: 34
<212> TYPE: DNA
<213> ORGANISM: Artificial Sequence
<220> FEATURE:
<223> OTHER INFORMATION: primer

<400> SEQUENCE: 30
ggcccccggg tcacagtctg gtctgacccc cact                              34

<210> SEQ ID NO 31
<211> LENGTH: 51
<212> TYPE: DNA
<213> ORGANISM: Artificial Sequence
<220> FEATURE:
<223> OTHER INFORMATION: primer

<400> SEQUENCE: 31 cccttctgg tttttccatt gtgttttggg gggaagtatg tattactgag t            51
```

The invention claimed is:

1. A product, which is:
a nucleic acid coding for a polypeptide, the sequence of which consists of less than 100 amino acids, wherein the sequence of said polypeptide comprises a sequence consisting of, in N- to C-terminal orientation,
the sequence of the signal peptide of the G protein of a non-apoptotic rabies virus strain,
the sequence of a fragment of the ectodomain of said G protein, wherein said ectodomain fragment is a C-terminal fragment of said ectodomain consisting of one to four amino acids, and
the sequence of the transmembrane domain of said G protein,
wherein the sequence of said polypeptide further comprises:

i. the sequence of SEQ ID NO: 6,
or
ii. a sequence, which:
is of 34 to 54 amino acids,
is at least 94% identical to said sequence of SEQ ID NO: 6 over the entire length of the shortest of the two sequences,
comprises a PDZ-BS sequence, wherein said PDZ-BS sequence is QTRL (SEQ ID NO: 10),
said sequence being referred to as variant sequence A,
or
iii. a fragment of said sequence of SEQ ID NO: 6 or of said variant sequence A, wherein said fragment is of at least 34 amino acids and has retained the PDZ-BS sequence of said sequence of SEQ ID NO: 6 or of said variant sequence A, respectively, or a vector comprising said nucleic acid, or a cell comprising said nucleic acid and/or said vector, or a pharmaceutical composition or drug, comprising at least one of said nucleic acid, vector and cell.

2. The product of claim 1, wherein said variant sequence A is of 44 amino acids and has the amino acid H or L, at position 11.

3. The product of claim 1, wherein said fragment of claim 1 iii. is the fragment 11-44 from the sequence of SEQ ID NO: 6.

4. The product of claim 1, wherein said polypeptide is or comprises the cytoplasmic fragment of the G protein of a rabies virus strain, or a sub-fragment of such a cytoplasmic fragment.

5. The product of claim 4, wherein said rabies virus strain is the strain deposited at the CNCM under I-4140 or I-4142.

6. The product of claim 1, wherein said transmembrane domain is at the N-terminal end of said sequence of claim 1 i., claim 1 ii. or claim 1 iii.

7. The product of claim 1, wherein said transmembrane domain is directly linked to the first amino acid at the N-terminal end of said sequence of claim 1 i., claim 1 ii. or claim 1 iii.

8. The product of claim 1, wherein said transmembrane domain is:

the sequence of SEQ ID NO: 23, or a variant sequence thereof, which is of 18 to 26 amino acids, and which is at least 94% identical to said sequence of SEQ ID NO: 23 over the shortest of the two sequences, which is the shorter of either SEQ ID NO: 23 or said variant sequence.

9. The product of claim 1, wherein said polypeptide comprises said sequence of SEQ ID NO: 6.

10. The product of claim 1, wherein the amino acid sequence of said polypeptide comprises the sequence of SEQ ID NO: 23 directly followed, in N- to C-terminal orientation, by the sequence of SEQ ID NO: 6, or by one to four amino acids and the sequence of SEQ ID NO: 6.

11. The product of claim 1, wherein said polypeptide comprises the sequence of SEQ ID NO: 25.

12. The product of claim 1, wherein said ectodomain fragment consists of the last two amino acids of the C-terminal end of said ectodomain, or consists of the amino acids GK.

13. The product of claim 1, wherein said polypeptide comprises the sequence of SEQ ID NO: 26.

14. The product of claim 1, wherein said signal peptide is at the N-terminal end of said polypeptide.

15. The product of claim 1, wherein said polypeptide is or comprises the sequence of SEQ ID NO: 27.

16. The product of claim 1, wherein said variant sequence A is the sequence of SEQ ID NO: 19.

* * * * *